US011531207B2

(12) United States Patent
Nikolenko et al.

(10) Patent No.: US 11,531,207 B2
(45) Date of Patent: *Dec. 20, 2022

(54) DEVICES, APPARATUS AND METHOD FOR PROVIDING PHOTOSTIMULATION AND IMAGING OF STRUCTURES

(71) Applicant: The Trustees of Columbia University in the City of New York, New York, NY (US)

(72) Inventors: Volodymyr Nikolenko, New York, NY (US); Rafael Yuste, New York, NY (US); Brendon O. Watson, New York, NY (US); Darcy Peterka, Hoboken, NJ (US)

(73) Assignee: The Trustees of Columbia University in the City of New York, New York, NY (US)

( * ) Notice: Subject to any disclaimer, the term of this patent is extended or adjusted under 35 U.S.C. 154(b) by 992 days.

This patent is subject to a terminal disclaimer.

(21) Appl. No.: 15/845,861

(22) Filed: Dec. 18, 2017

(65) Prior Publication Data
US 2018/0173004 A1  Jun. 21, 2018

Related U.S. Application Data

(63) Continuation of application No. 13/121,084, filed as application No. PCT/US2009/058490 on Sep. 25, 2009, now Pat. No. 9,846,313.
(Continued)

(51) Int. Cl.
*G02B 27/46* (2006.01)
*G01N 21/64* (2006.01)
(Continued)

(52) U.S. Cl.
CPC ......... *G02B 27/46* (2013.01); *G01N 21/6458* (2013.01); *A61N 5/0622* (2013.01);
(Continued)

(58) Field of Classification Search
CPC ................ G02B 27/46; G02B 21/0004; G02B 21/0032; G02B 26/06; G02B 21/06;
(Continued)

(56) References Cited

U.S. PATENT DOCUMENTS 5,587,832 A    12/1996  Krause et al.
6,248,988 B1   6/2001   Krantz et al.
(Continued)

FOREIGN PATENT DOCUMENTS

CN    101171553       4/2008
EP    1788379 A1      2/2005
(Continued)

OTHER PUBLICATIONS

Lutz et al, "Holographic photolysis of caged neurotransmitters," Nature Methods | vol. 5 No. 9 | Sep. 2008 | 821 (Year: 2008).*
(Continued)

*Primary Examiner* — Xiuyu Tai
(74) *Attorney, Agent, or Firm* — Hunton Andrews Kurth LLP

(57) ABSTRACT

According to exemplary embodiments of the present disclosure, it is possible to provide method, system, arrangement, computer-accessible medium and device to stimulate individual neurons in brain slices in any arbitrary spatio-temporal pattern, using two-photon uncaging of photo-sensitive compounds such as MNI-glutamate and/or RuBi-Glutamate with beam multiplexing. Such exemplary method and device can have single-cell and three-dimensional precision. For example, by sequentially stimulating up to a thousand potential presynaptic neurons, it is possible to generate detailed
(Continued)

functional maps of inputs to a cell. In addition, it is possible to combine this exemplary approach with two-photon calcium imaging in an all-optical method to image and manipulate circuit activity. Further exemplary embodiments of the present disclosure can include a light-weight, compact portable device providing for uses in a wide variety of applications.

25 Claims, 30 Drawing Sheets

Related U.S. Application Data

(60) Provisional application No. 61/177,239, filed on May 11, 2009, provisional application No. 61/212,924, filed on Apr. 17, 2009, provisional application No. 61/194,145, filed on Sep. 25, 2008.

(51) Int. Cl.
    *A61N 5/06* (2006.01)
    *G01N 21/65* (2006.01)
    *G02B 21/00* (2006.01)

(52) U.S. Cl.
    CPC ............... *G01N 2021/653* (2013.01); *G01N 2201/0221* (2013.01); *G02B 21/0004* (2013.01)

(58) Field of Classification Search
    CPC ....... G01N 21/6458; G01N 2201/0221; G01N 2021/653; G01N 21/00; G01N 21/65; G01N 2021/656; A61N 5/0622; A61N 1/00; A61N 2/00; A61B 5/0066; A61B 5/6852; A61B 18/203; A61B 2018/00452; A61B 2018/2023; A61B 2018/00005; A61B 2018/00476; A61B 2018/20355; A61B 2017/00765; A61B 2018/0047; A61H 39/002; A61H 2201/10; H01J 49/164; G01J 11/00; G01J 3/00
    See application file for complete search history.

(56) References Cited

U.S. PATENT DOCUMENTS

| | | | |
|---|---|---|---|
| 6,399,935 | B1 | 6/2002 | Thomas et al. |
| 7,311,723 | B2 | 12/2007 | Seibel et al. |
| 7,339,148 | B2 | 3/2008 | Kawano et al. |
| 7,399,647 | B2 | 7/2008 | Reinhorn et al. |
| 7,400,446 | B2 | 7/2008 | Mikuriya et al. |
| 7,737,088 | B1 | 6/2010 | Stähler et al. |
| 2001/0012099 | A1 | 8/2001 | Kumagai |
| 2002/0095075 | A1 | 7/2002 | Madarasz et al. |
| 2002/0154398 | A1 | 10/2002 | Ralf et al. |
| 2003/0099264 | A1 | 5/2003 | Dantus et al. |
| 2004/0089798 | A1 | 5/2004 | Lewis et al. |
| 2004/0113059 | A1 | 6/2004 | Kawano et al. |
| 2004/0254474 | A1 | 12/2004 | Seibel et al. |
| 2004/0263841 | A1 | 12/2004 | Caracci et al. |
| 2005/0017160 | A1 | 1/2005 | Wolleschensky |
| 2005/0072913 | A1 | 4/2005 | Lange et al. |
| 2005/0082491 | A1 | 4/2005 | Motomura |
| 2005/0082494 | A1 | 4/2005 | Motomura |
| 2005/0224695 | A1 | 10/2005 | Mushika |
| 2006/0004306 | A1* | 1/2006 | Altshuler ............. A61H 39/002 601/3 |
| 2006/0043184 | A1 | 3/2006 | Fukuchi et al. |
| 2006/0184043 | A1 | 8/2006 | Tromberg et al. |
| 2006/0187974 | A1 | 8/2006 | Dantus |
| 2006/0209399 | A1 | 9/2006 | Mikuriya et al. |
| 2007/0016078 | A1 | 1/2007 | Hoyt et al. |
| 2007/0088219 | A1* | 4/2007 | Xie ..................... A61B 5/0066 600/473 |
| 2007/0132998 | A1 | 6/2007 | Tang et al. |
| 2007/0229946 | A1 | 10/2007 | Okada et al. |
| 2007/0261127 | A1 | 11/2007 | Boyden et al. |
| 2007/0262264 | A1 | 11/2007 | Hasegawa |
| 2008/0151366 | A1 | 6/2008 | Arya et al. |
| 2008/0156999 | A1 | 7/2008 | Nishiwaki |
| 2008/0192231 | A1 | 8/2008 | Jureller |
| 2010/0214404 | A1 | 8/2010 | Chen et al. |
| 2013/0181143 | A1* | 7/2013 | Betzig ................ G02B 21/0032 250/459.1 |

FOREIGN PATENT DOCUMENTS

| | | |
|---|---|---|
| JP | H09329750 | 12/1997 |
| JP | H10293256 | 11/1998 |
| JP | 2001-176789 A | 6/2001 |
| JP | 2008523781 | 7/2002 |
| JP | 2003195174 | 7/2003 |
| JP | 2004503832 | 2/2004 |
| JP | 2004199063 | 7/2004 |
| JP | 2004199063 A | 7/2004 |
| JP | 2004219537 | 8/2004 |
| JP | 2005128086 A | 5/2005 |
| JP | 2006-888 A | 1/2006 |
| JP | 2006133499 | 5/2006 |
| JP | 2003195174 A | 7/2006 |
| JP | 2006516730 | 7/2006 |
| JP | 2006235420 | 9/2006 |
| JP | 2007521482 | 8/2007 |
| JP | 2007263730 | 10/2007 |
| JP | 2007264664 | 10/2007 |
| JP | 2008504557 | 2/2008 |
| JP | 2008122629 A | 5/2008 |
| JP | 2003043363 A | 2/2013 |
| WO | 2000055882 A1 | 9/2000 |
| WO | 2006004743 | 1/2006 |
| WO | 2006091714 A2 | 8/2006 |
| WO | 2007024391 A2 | 3/2007 |
| WO | 2008034102 | 3/2008 |
| WO | 2008092107 | 7/2008 |
| WO | 2011023593 | 3/2011 |

OTHER PUBLICATIONS

Notice of Reasons for Rejection for Japanese Patent Application No. 2017-131352 dated May 22, 2019.
The First Office action for Chinese Patent Application No. 201710224537.x dated Apr. 23, 2019.
Z.A. Peterlin, et al., "Optical probing of neuronal circuits with calcium indicators" Proc. Natl. Acad. Sci. USA 97 (7), 3619-3624 (2000).
The First Japanese Office Action Application No. 2015-165385 dated Aug. 4, 2015.
The First Chinese Office Action Application No. 200980143446.7 dated Oct. 29, 2015.
The Canadian Office Action Application No. 2,738,652 dated Nov. 9, 2015.
Shoham, S., et al "Rapid neurotransmitter uncaging in spatially defined patterns" Nature Methods, 2: 837-843 (2005).
Volodymyr Nikolenko, et al. "A two-photon and second-harmonic microscope" Methods, 30: 3-15 (2003).
A. Nimmerjahn, et al., "Sulforhodamine 101 as a specific marker of astroglia in the neocortex in vivo" Nat Methods 1(1), 31-37 (2004).
Canepari, M.,et al "Photochemical & pharmacological evaluation of 7-nitroindolinyl- and 4-methoxy-7-nitroindolinyl . . . neurotransmitters." J Neurosci Methods 20;112,29-42(2001).
E. S. Boyden, et al., "Millisecond-timescale, genetically targeted optical control of neural activity" Nature neuroscience 8(9), 1263-1268 (2005).
FH. Crick, "Thinking about the brain" Sci. Am. 241 (3), 219-232 (1979).
Sacconi L, et al. "Multiphoton multifocal microscopy exploiting a diffractive optical element" Opt Lett. 28 (20), 1918-1920 (2003).
H. U. Dodt, et al. "Circuitry of rat barrel cortex investigated by infrared-guided laser stimulation" Neuroreport 14 (4), 623-627, (2003).

(56) References Cited

OTHER PUBLICATIONS

I. C. Farber and A. Grinvald, "Identification of presynaptic neurons by laser photostimulation" Science 222, 1025-1027 (1983).
M. B. Dalva and L. C. Katz, "Rearrangements of synaptic connections in visual cortex revealed by laser photostimulation" Science 265 (5169) 255-258 (1994).
Kotter R., et al. "Optical release of caged glutamate for stimulation of neurons in the in vitro slice preparation." J Biomed Opt. Jan.-Feb. 2005;10(1):11003.
Yuste, R. and Katz, L. C. "Control of postsynaptic calcium influx in developing neocortex by excitatory and inhibitory neurotransmitters." Neuron 6: 333-344. (1991).
Communication pursuant to Article 94(3) EPC dated Jul. 18, 2017 for European Patent Application No. 09816957.6.
Canadian Examination Report dated Nov. 30, 2016 for Canadian Patent Application No. 2,738,652.
Supplementary Partial European Search Report dated Oct. 16, 2014 for EP 09816957.
Canadian Examination Report dated Nov. 9, 2015 for Canadian No. 2,738,652.
Australian Patent Examination Report dated Mar. 26, 2015 for Australian Patent application No. 2014206165.
The Notification of Reexamination of the Chinese Application No. 200980143446.7 dated Jun. 21, 2016.
The Japanese Office Action Application No. 2014-165385 dated Jun. 7, 2016.
Nikolenko, V., et al., "Simultaneous Optical Stimulation and Two-Photon Imaging of Neocortical Circuits." Society for Neuroscience, New Orleans, May 2003.
The 1st Decision of Refusal for Japanese Patent Application No. 2011-529287 dated Sep. 10, 2013.
The 2nd Decision of Refusal for Japanese Patent Application No. 2011-529287 dated Apr. 15, 2014.
The First Examination Report for Australian Patent Application No. 2009296405 dated Oct. 24, 2012.
The Second Examination Report for Australian Patent Application No. 2009296405 dated Apr. 11, 2013.
The Third Examination Report for Australian Patent Application No. 2009296405 dated Nov. 18, 2013.
The Second Office Action for Chinese Patent Application No. 200980143446.7 dated Dec. 16, 2013.
The Third Office Action for Chinese Patent Application No. 200980143446.7 dated Sep. 7, 2014.
The First Office Action for European Patent Application No. 09816957.6 dated Jul. 3, 2014.
Papagiokoumou et al. (Dec. 10, 2008) "Patterned two-photon illumination by Spatiotemporal shaping of ultrashort pulses," Optics Express 16(26):22039-22047.
Emiliani et al. (2006) "Wavefront engineering microscopy to study 3D mechotransduction in living cells," Nanphotonics I Proc ofSPIE 6195:61950JI-61950J8.
Pre-trial Reexamination Report for Japanese Patent Application No. 201-529287 dated Nov. 21, 2014.
The Fourth Chinese Office Action Application No. 200980143446.7 dated Apr. 15, 2015.
A. A. Oliva, Jr. et al., "Novel Hippocampal Interneuronal Subtypes Identified Using . . . Fluorescent Protein in GABAergic Interneurons" JNeurosci 20 (9), 3354 (2000).
A. J. Trevelyan, et al, "Modular Propagation of Epileptiform . . . Neocortex" J. of neurosci: the official journal of the Society for Neuroscience 26 (48), 12447 (2006).
Araya; R., et al. "The spine neck filters membrane potentials." Proc. Natl. Acad. Sci. USA 103, 17961-17966 (2006).
C. Boucsein, et al., "Controlling Synaptic Input Patterns In Vitro by Dynamic Photo Stimulation" Journal of neurophysiology 94 (4), 2948-2958 (2005).
E.M. Callaway and L.C. Katz, "Photostimulation using caged glutamate reveals functional circuitry in living brain slices." Proc. Natl. Acad. Sci. U.S.A. 90, 7661 (1993).

F. Zhang, et al., "Multimodal fast optical interrogation of neural circuitry" Nature 446 (7136), 633-641 (2007).
Fino, et al., "RuBi-Glutamate: two-photon and visible-light photoactivation of neurons and dendritic spines;" Frontiers in Neural Circuits, 3, (2009).
G.M. Shepherd et al. "Circuit Analysis of Experience-Dependent Plasticity in the Developing Rat Barrel Cortex" Neuron, 38 (2), 277-289 (2003).
J. J. Hopfield, "Neural networks and physical systems with emegent collective computational abilities" Proc. Natl. Acad. Sci. USA 79, 2554 (1982).
JV. Le Be and H. Markram "Spontaneous and evoked synaptic rewiring in the neonatal neocortex" Proc Natl Acad Sci U S A. 103, 13214-131419 (2006).
A. Majewska, et al. "A custom-made two-photon microscope and deconvolution system" Pflugers Archiv—Eur. J. Physiol. 441, 398-408 (2000).
Matsuzaki, M., et al. Dendritic spine geometry is critical for AMPA receptor expression in hippocampal CAI pyramidal neurons. Nat Neurosci 4, 1086-1092. (2001).
R. Cossart, et al. "Attractor dynamics of network UP states in the neocortex" Nature 423, 283-288 (2003).
Rial Verde EM, et al. "Photoretease of GABA with Visible Light Using an Inorganic Caging Group" Frontiers in Neural Circuits;2:2. 2008.
T. Badea, et al., "Calcium Imaging of Epileptiform Events with Signle-Cell Resolution" J. Neurobiol. 48, 215 (2001).
Watson, et al. "Two-photon imaging with diffractive optical elements" Frontiers in Neural Circuits, 3, 1 (2009).
Y Wang, et al., "Anatomical, physiological and molecular properties of Martinotti cells in the somatosensory cortex of the juvenile rat" J. Physiol 561, 65-90 (2004).
Y. Yoshimura, et al. "Excitatory cortical neurons form fine-scale functional networks" Nature 433 (7028), 868-873 (2005).
International Search Report for the International Application No. PCT/US2009/058490 [Cited in priority U.S. Pat. No. 9,846,313].
Written Opinion for the International Application No. PCT/US2009/058490 [Cited in priority U.S. Pat. No. 9,846,313].
First Office Action for Chinese Patent Application No. 200980143446.7 dated Feb. 22, 2013 [Cited in priority U.S. Pat. No. 9,846,313].
C. Lutz et al., "Holographic photolysis of caged neurotransmitters" Nature Methods, vol. 5, No. 9, pp. 821-827, Sep. 2008 [Cited in priority U.S. Pat. No. 9,846,313].
Bingelyte, V. et al., "Optically Controlled Three-Dimensional Rotation of Microscopic Objects", Applied Physics Letters, vol. 82, No. 5, Feb. 3, 2003, 829-831 [Cited in priority U.S. Pat. No. 9,846,313].
Two-photon Photostimulation and Imaging of NeuralCircuits, Volodymyr Nikolenko, Gordon Research Conference "Neural Circuits & Plasticity", Jul. 4, 2007 [Cited in priority U.S. Pat. No. 9,846,313].
Multifocal Multiphoton Microscopy, Opt. Lett. vol. 23, No. 9, pp. 655-657 (May 1, 1998) [Cited in priority U.S. Pat. No. 9,846,313].
Second-harmonic-generation Microscope with a Microlens Array Scanner, opt. Lett. vol. 27, No. 15, (Aug. 1, 2002) [Cited in priority U.S. Pat. No. 9,846,313].
Multiphoton multifocal micrscopy Exploiting a Diffractive Optical Element, Opt. Lett. vol. 28, No. 20 (Oct. 15, 2003) [Cited in priority U.S. Pat. No. 9,846,313].
Sinclair, Gavin et al., "Interactive Application in Holographic Optical Tweezers of a Multi-plane Gerchberg-Saxton Algorithm for Three-Dimensional Light Shaping," Optic Express, vol. 12, No. 8, pp. 1665-1670, Apr. 19, 2004.
Nikolenko, Volodymyr et al., "SLM Microscopy: Scanless Two-Photon Imaging and Photostimulation using Spatial Light Modulators," Frontiers in Neural Circuits, vol. 2, pp. 1-15, Dec. 2008.
Nikolenko, Volodymyr et al., "Two-Photon Photostimulation and Imaging of Neural Circuits," nature Methods, vol. 4, No. 11, pp. 943-950, Nov. 30, 2007.
Canadian Examiner's Report dated Nov. 20, 2017 for Canadian Patent Application No. 2738652.
Canadian Examiner's Report dated Nov. 30, 2016 for Canadian Patent Application No. 2738652.

(56) References Cited

OTHER PUBLICATIONS

Majewska, Ania et al., A Custom-Made Two-Photon Microscope and Deconvolution System, Eur J Physiol, vol. 441, pp. 398-408, 2000.

Matsuzaki, Masanori et al., "Dendritic Spine Geometry is Critical for AMPA Receptor Expression in Hippocampal CA1 Pyramidal Neurons," Nature Neuroscience, vol. 4, No. 11, pp. 1086-1092, Nov. 2001.

Rial Verde, Emiliano M. et al., Photorelease of GABA with Visible Light Using an Inorganic Caging Group, Frontiers, vol. 2, Article 2, pp. 1-8, Aug. 2008.

Oliva, Anthony A. et al., "Novel Hippocampal Interneuronal Subtypes Identified Using Transgenic mice That Express Green Flurescent Proteinin GABAergic Interneurons," The Journal of Neuroscience, vol. 20, No. 9, pp. 3354-3368, May 1, 2000.

Yuste, Rafael et al., "Imaging in Neuroscience and Development," Cold Spring Harbor Press, Cold Spring Harbor, 2005.

Hopfield, J.J. et al., "Neural Networks and Physical Systems with Emergent Collective Computational Abilities," Proc. Natl. Acad. Sci., vol. 79, pp. 2554-2558, Apr. 1982.

English translation of First Notice of Reasons for Rejection dated Jul. 25, 2018 for Japanese Patent Application No. 2017-131352.

\* cited by examiner

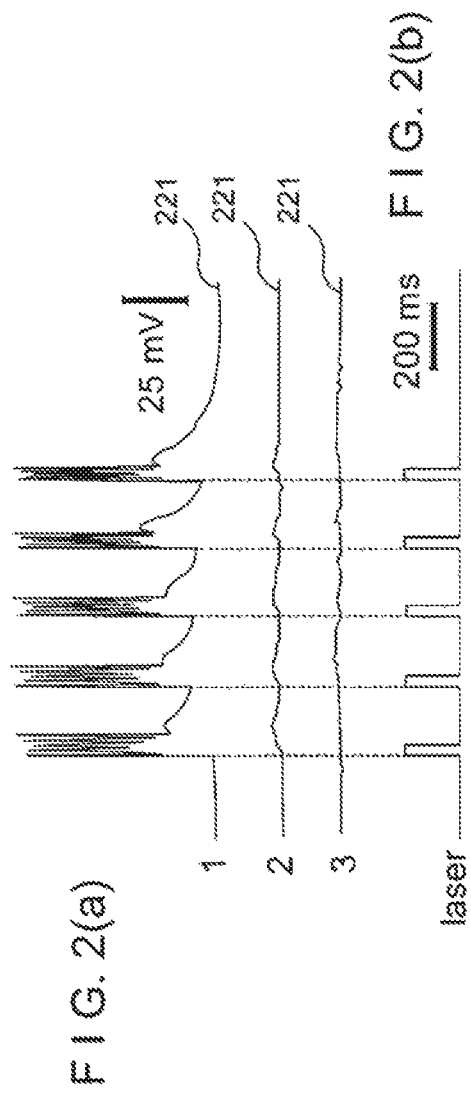
FIG. 2(a)
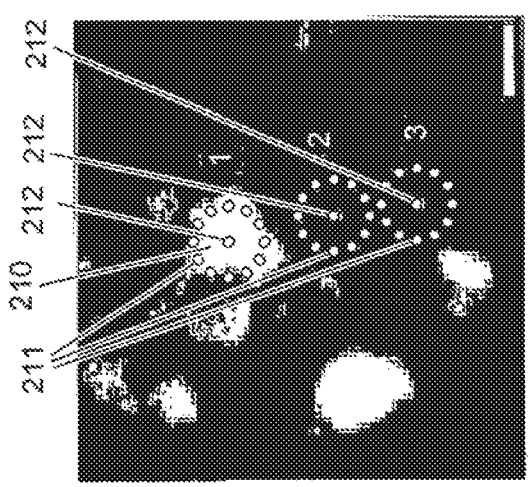
FIG. 2(b)
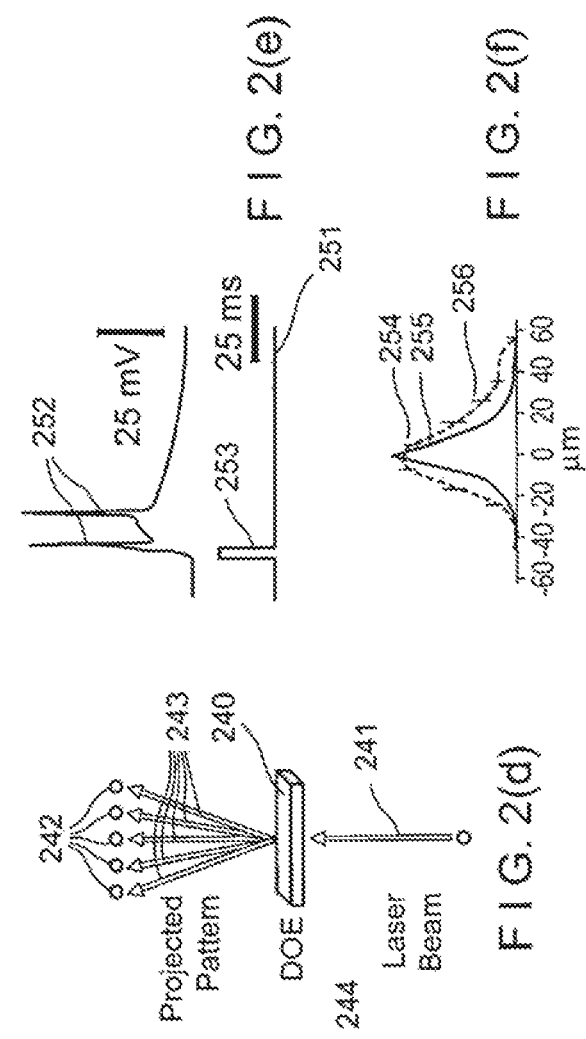
FIG. 2(c)
FIG. 2(d)
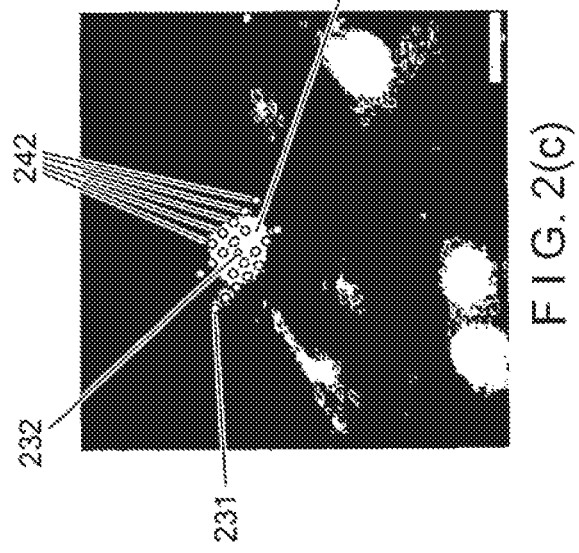
FIG. 2(e)
FIG. 2(f)

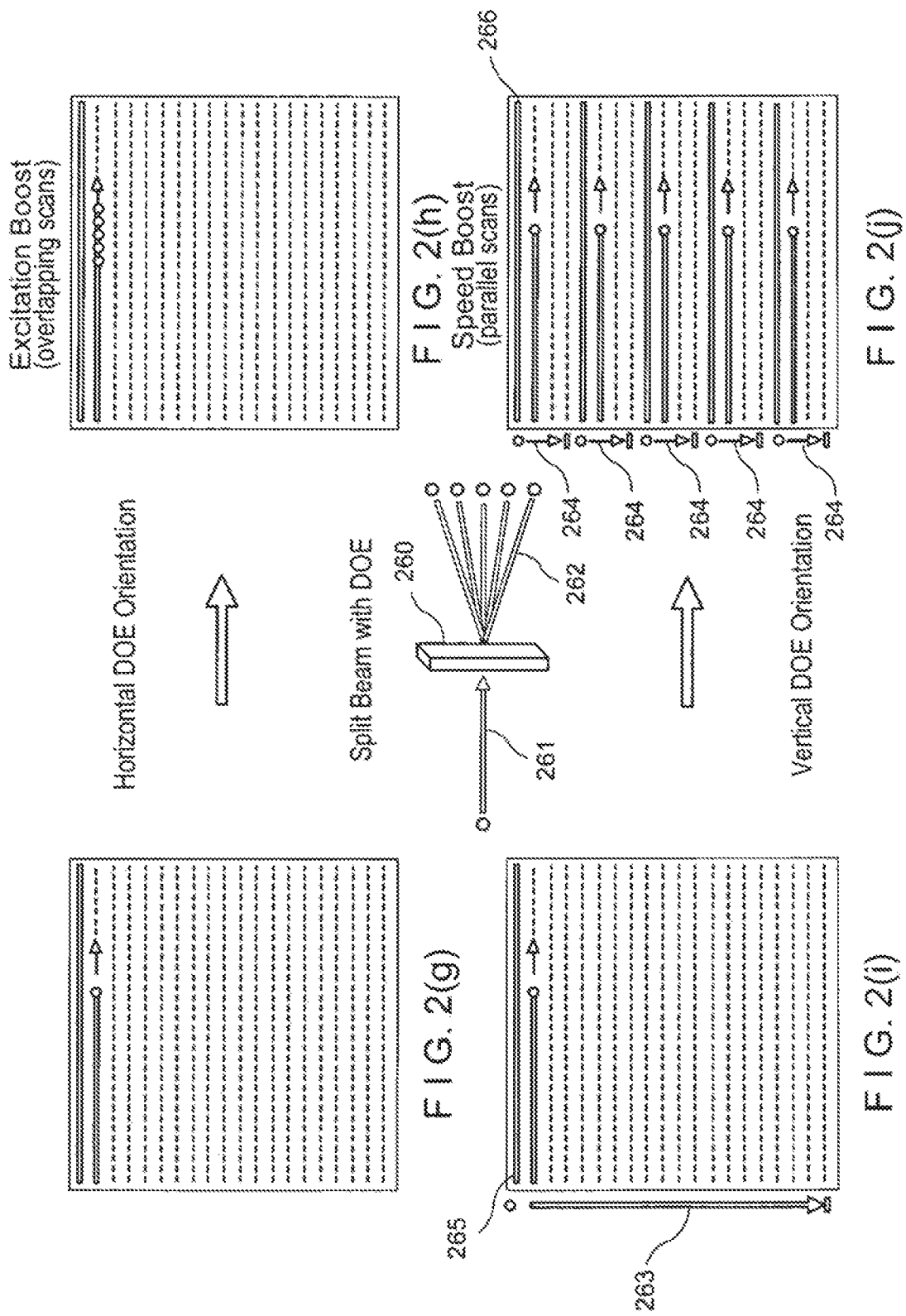

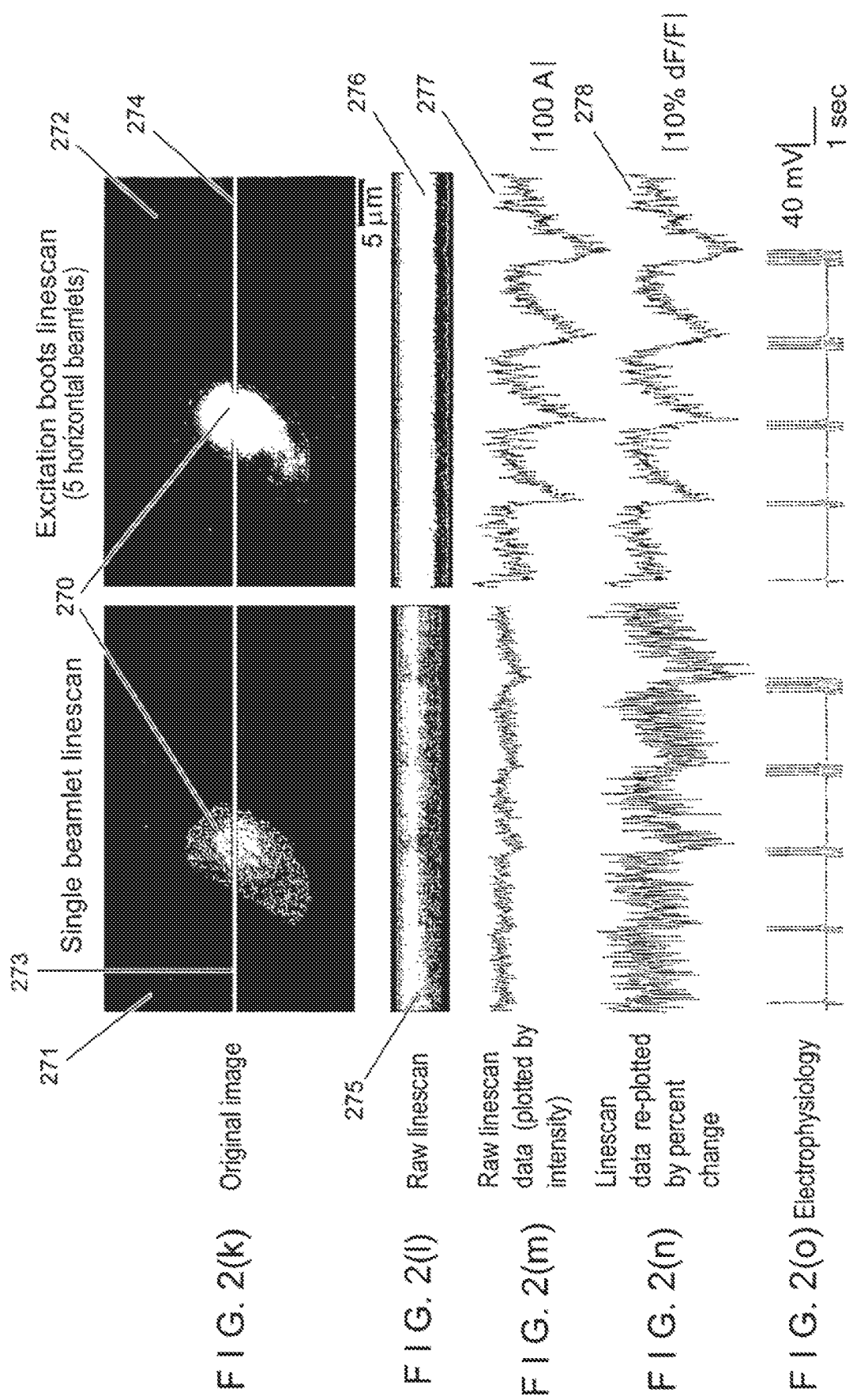

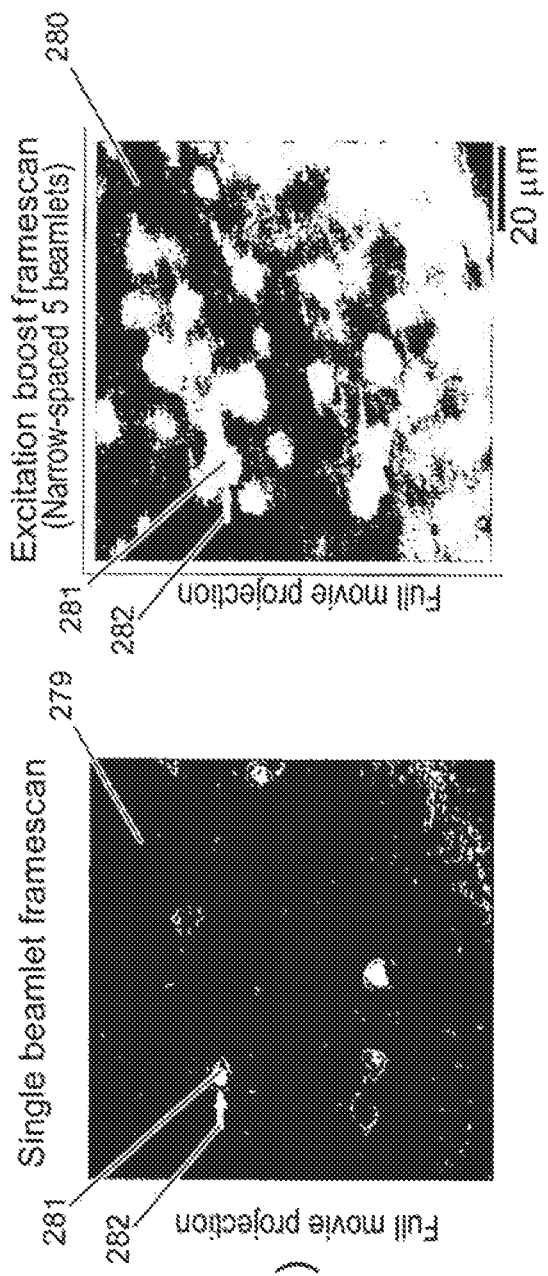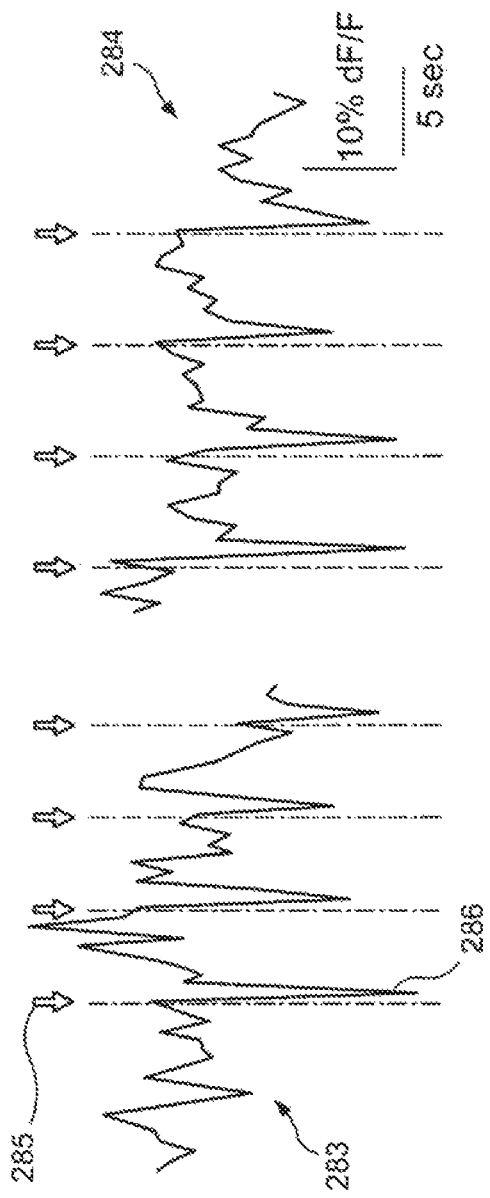
FIG. 2(p)
FIG. 2(q)

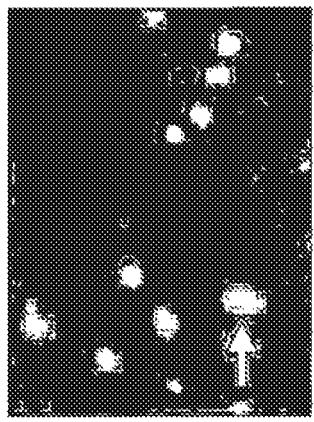
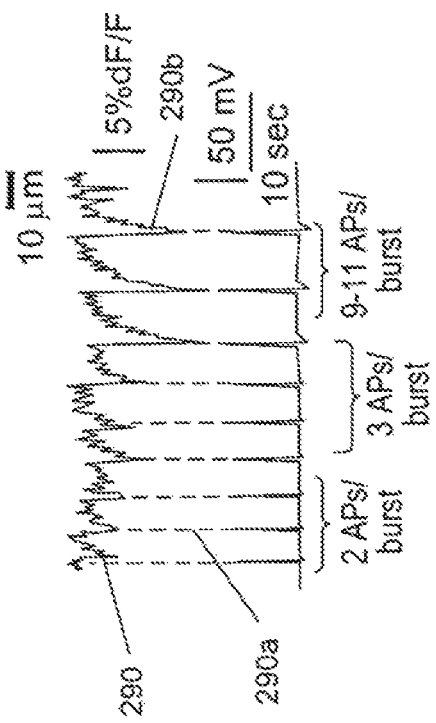
FIG. 2(s)
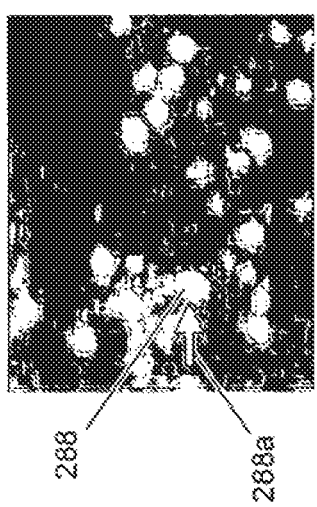
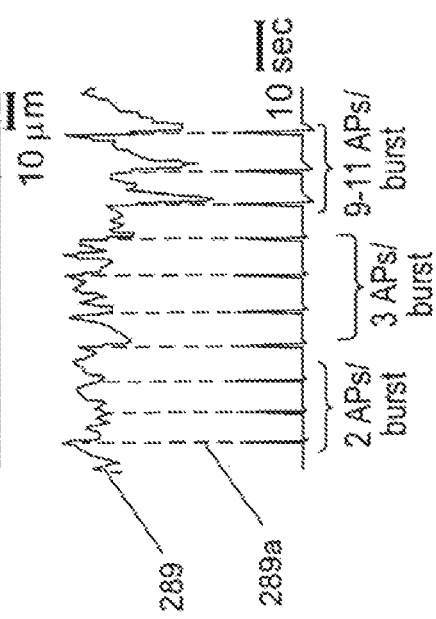
FIG. 2(t)

Exemplary Analysis of True and False Positive Responses

| | True positives | | | | False positives | | | |
|---|---|---|---|---|---|---|---|---|
| | Amplitude first EPSP, mV | Peak amplitude, mV | Latency after laser pulse, ms | Rise speed, mV/ms | Amplitude first EPSP, mV | Peak amplitude, mV | Latency after laser pulse, ms | Rise speed, mV/ms |
| Mean | 1.04 | 3.21 | 57.85 | 0.066 | 5.69 | 5.76 | 30.00 | 0.056 |
| Standard Deviation | 0.26 | 1.16 | 6.46 | 0.021 | 2.00 | 1.83 | 9.35 | 0.016 |
| Standard Error | 0.11 | 0.52 | 2.89 | 0.009 | 0.89 | 0.82 | 4.18 | 0.007 |
| Two-tail p-value | $1.77 \times 10^{-13}$ | $2.84 \times 10^{-5}$ | $9.89 \times 10^{-20}$ | 0.0365 | | | | |

FIG. 3(g)

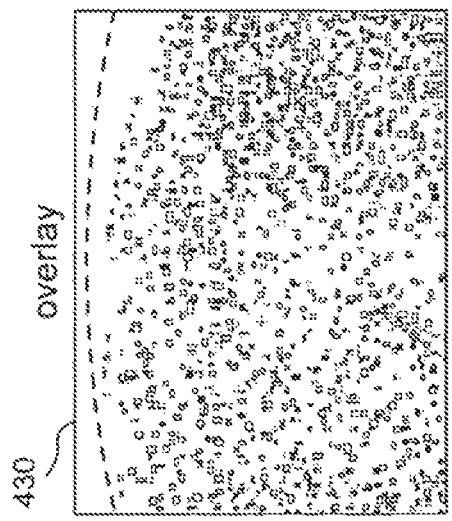
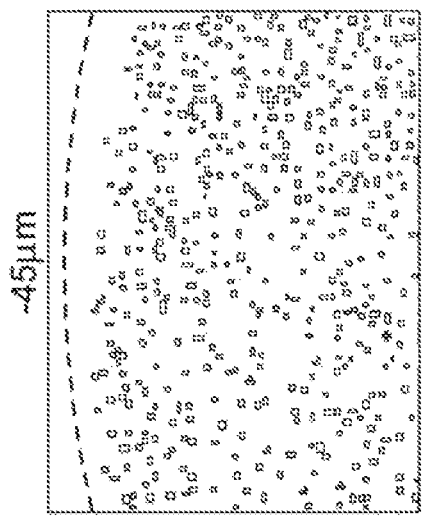
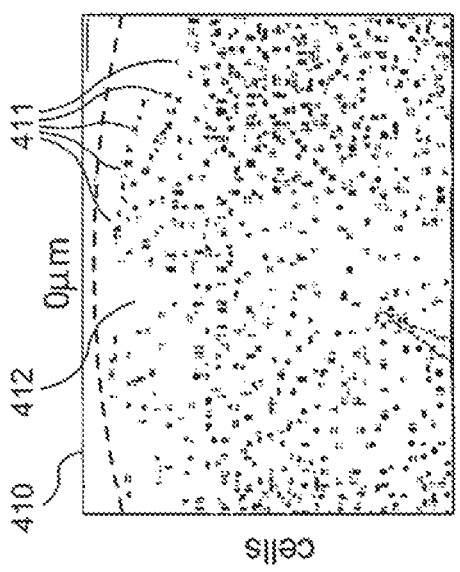
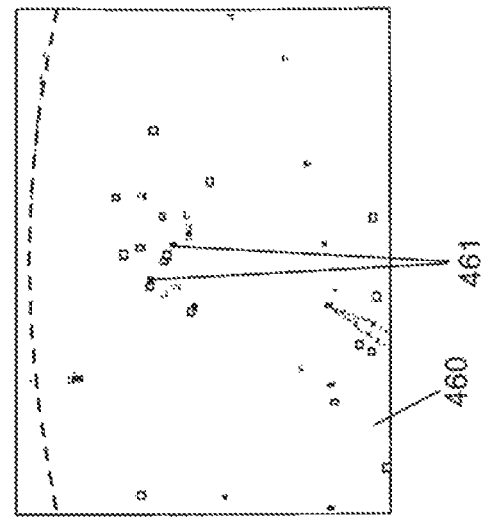
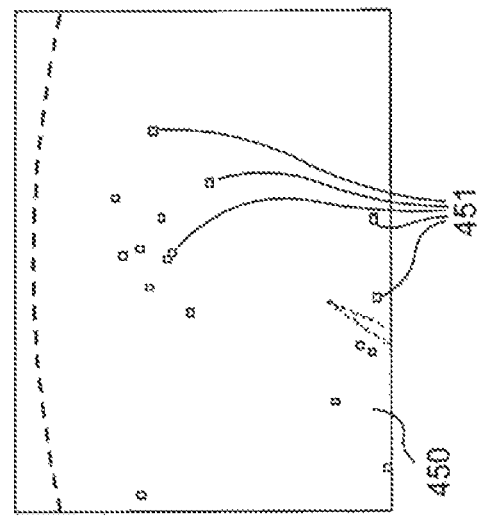
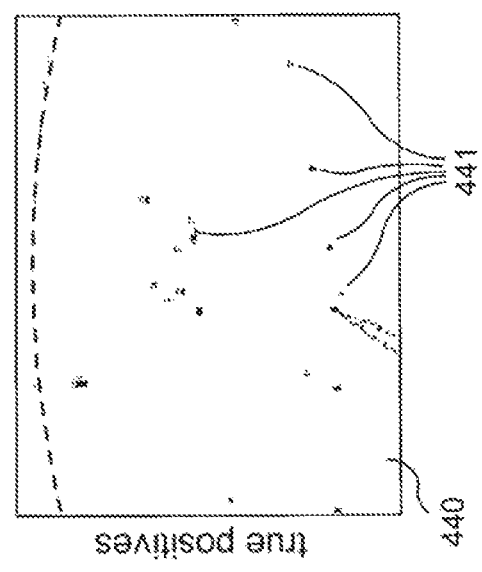

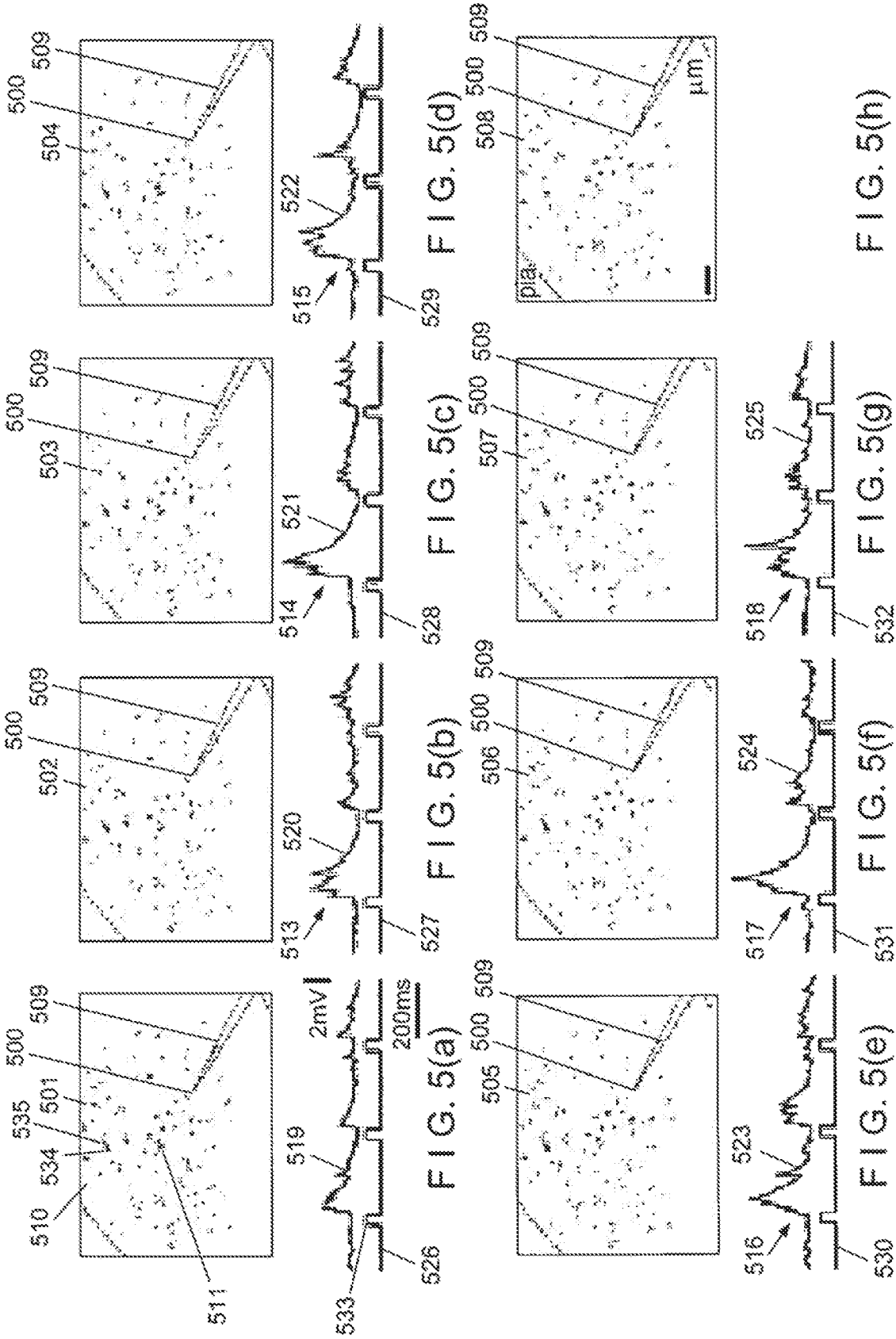

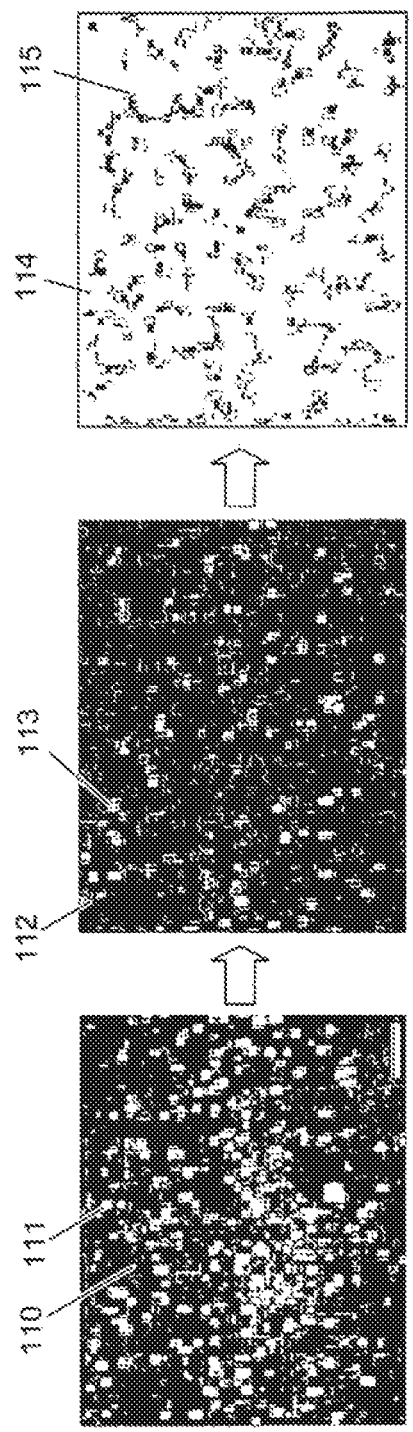
FIG. 7(a)
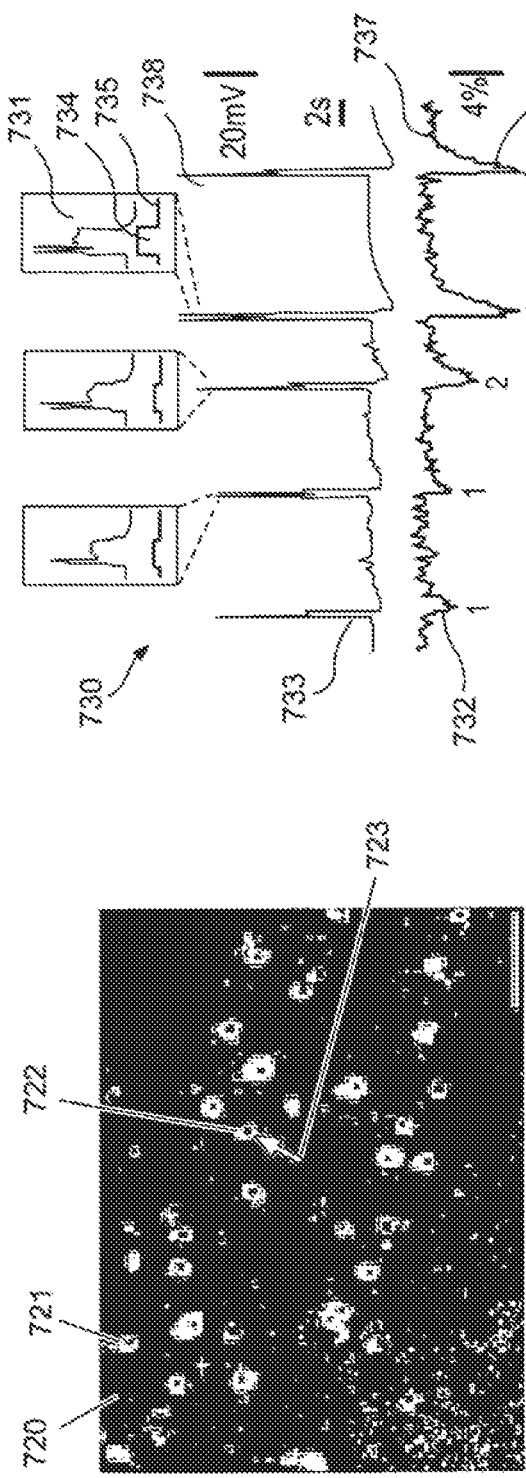
FIG. 7(b)
FIG. 7(c)

DEVICES, APPARATUS AND METHOD FOR PROVIDING PHOTOSTIMULATION AND IMAGING OF STRUCTURES

CROSS-REFERENCE TO RELATED APPLICATIONS

The present application is a continuation of U.S. patent application Ser. No. 13/121,084 filed Jun. 8, 2011, and being issued as U.S. Pat. No. 9,846,313 on Dec. 19, 2017, and claims priority from International Patent Application No. PCT/US2009/058490 filed Sep. 25, 2009, U.S. Provisional Patent Application Ser. No. 61/194,145 filed Sep. 25, 2008, U.S. Provisional Patent Application Ser. No. 61/212,924 filed Apr. 17, 2009, and U.S. Provisional Patent Application Ser. No. 61/177,239 filed May 11, 2009, the entire disclosures of which are hereby incorporated herein by reference.

STATEMENT REGARDING FEDERALLY-SPONSORED RESEARCH OR DEVELOPMENT

This invention was made with government support under grant EY011787 awarded by the National Institutes of Health. The government has certain rights in this invention.

FIELD OF THE DISCLOSURE

Exemplary embodiments of the present disclosure relate to devices, apparatus and methods for providing photo-activation and imaging of structures, and more particularly to photo-stimulation and imaging of neuronal circuits.

BACKGROUND INFORMATION

Neuronal circuits are composed of a great diversity of cell types and it is likely that each cell type carries out a specialized function. (See P. Sterling, "The Synaptic Organization of the Brain," edited by G. M. Shepherd, Oxford University Press, Oxford, 1990). Therefore, as a prerequisite to understanding the function of a circuit, it appears necessary to map synaptic connections among different types of neurons, or, as proposed in the Crick publication, to map all connections made onto a given cell. (See F H. Crick, Sci. Am. 241 (3), 219 (1979)).

Following the knowledge which describes the use of fluorescent membrane probes (see I. C. Farber and A. Grinvald, Science 222, 1025 (1983)), photostimulation of neurons using caged glutamate (see E. M. Callaway and L. C. Katz, Proc. Natl. Acad. Sci. U.S.A. 90, 7661 (1993)) has greatly advanced this research program, generating high-resolution input maps of neurons in brain slices. (See id.; M. B. Dalva and L. C. Katz, Science 265 (5169) 255 (1994); G. M. Shepherd, T. A. Pologruto, and K. Svoboda, Neuron 38 (2), 277 (2003); C. Boucscin, M. Nawrot, S. Rotter et al., Journal of neurophysiology 94 (4), 2948 (2005); R. Kotter, D. Schubert, J. Dyhrfield-Johnsen et al., J Biomed Opt 10 (1), 11003 (2005); H. U. Dodt, A. Schierloh, M. Eder et al., Neuroreport 14 (4), 623 (2003); and S. Shoham, D. H. O'Connor, D. V. Sarkisov et al., Nature methods 2 (11), 837 (2005)). In this method, glutamate uncaging is achieved by focusing ultraviolet light at a particular position in the slice, while simultaneously recording intracellular responses from a neuron at a different location. By moving the uncaging beam systematically across the slice, one can map the territories that generate excitatory or inhibitory responses in the recorded cell. While being useful, this method likely suffers from the problem that, due to the inherent scattering of light in living tissue and the large uncaging area generated by one-photon excitation, the stimulated area contains more than one neuron. Thus, one-photon photostimulation has not revealed synaptic connections between cells, but instead connections between a particular territory and a recorded neuron.

Accordingly, there may be a need to address at least some of the deficiencies described herein.

SUMMARY OF EXEMPLARY EMBODIMENTS

To overcome at least such limitation, it is possible to provide exemplary embodiments of two-photon photo-stimulation methods, systems and devices.

According to one exemplary embodiment of the present disclosure, device and method can be provided for effecting at least one radiation. For example, at least one particular arrangement can be provided which is structured or configured to effect the radiation(s) to trigger a photo activation, a photo-inactivation and/or a photo-chemical effect of at least one portion of at least one sample. The radiation(s) can include at least one beam, and the particular arrangement(s) can be further structured or configured to split the at least one beam into multiple beamlets so that at least some of which impact the sample(s). The sample can be a biological sample, a chemical composition, a semiconductor arrangement and/or a drug-delivery arrangement.

According to one exemplary embodiment, the particular arrangement(s) can include at least one diffractive optical arrangement. The particular arrangement(s) and/or the diffractive optical arrangement(s) can include at least one spatial light modulation (SLM) arrangement. In addition, the particular arrangement(s) can effect the at least one radiation by exciting the at least one radiation in a non-linear manner. A signal-to-noise ratio of the at least one radiation can be greater than about 1.94 fold over a signal from a single radiation system.

According to another exemplary embodiment of the present disclosure at least one further arrangement can be provided which can be configured to receive data associated with the at least one effected radiation and generate at least one image of the portion(s) of the sample(s) as a function of the data, and the image(s) can be generated at a duration of the imaging cycle that is less than about 100 ms. Further, the particular arrangement(s) can be configured or structured to provide the at least one effected radiation to a biological sample to provide a photodynamic effect thereto. The effected radiation(s) can have an average power that is higher than 100 milliwatts net on the at least one sample. For example, at least a portion of the particular arrangement(s) can be provided in an endoscopic arrangement.

In still another exemplary embodiment of the present disclosure, the particular arrangement(s) can be further configured or structured to illuminate microscopic structures within the sample(s) using the radiation(s) and/or to adjust a phase of the radiation(s) to impact the sample(s) and obtain at least one depth information therefor. The SLM arrangement can be configured or structured to illuminate microscopic structures within the sample(s) using the radiation(s) and/or to impact the sample(s) and obtain at least one depth information therefor. The particular arrangement(s) can be included in at least one scanless spatial light modulation (SLM)-based microscope arrangement. The scanless SLM-based microscope arrangement(s) can effect a coherent light of the radiation(s), and the coherent light can include a laser.

According to a further exemplary embodiment of the present disclosure, the SLM arrangement(s) can be configured or structured to correct for at least one aberration associated with the at least one sample for the at least one image. The radiation(s) can include at least one light radiation, and the SLM arrangement(s) can be configured or structured to provide the light radiation to the portion(s) of the sample(s) at a depth that is greater than about 1 mm at a particular effective intensity. The light radiation(s) can be provided at the depth within the portion(s) that is/are based on at least one wavelength of the light radiation(s). The further arrangement(s) can generate the image(s) based on at least one multi-mode procedure. The SLM arrangement can be further structured or configured to generate a set of angled intersecting beamlets from the radiation(s). The SLM arrangement(s) is structured or configured to effect the radiation(s) to effectuate (i) a two- or three-photon absorption within the at least one sample, (ii) a Second Harmonics Generation (SHG) associated with the radiation(s), (iii) a coherent anti-Stokes Raman spectroscopic imaging (CARS) procedure so that the further arrangement(s) can generate the image(s), and/or (iv) a Four-wave mixing imaging (FWM) procedure so that the further arrangement(s) can generate the image(s).

According to yet another exemplary embodiment, the SLM arrangement(s) can be structured or configured to modify at least one of a shape, a size or a flow direction of beams of the radiation(s) to effectuate a two- and/or three-photon absorption within the at least one sample. Further, the SLM arrangement(s) can include a phase-only SLM arrangement, e.g., which can prevent a substantial reduction of intensity of the radiation(s). For example, the SLM arrangement(s) can include a single optical component which can be solely configured or structured to (i) transmit or reflect and further modify the radiation(s), (ii) reduce an intensity of the radiation(s), and (iii) at least partially block the at least one radiation(s).

In yet a further exemplary embodiment of the present disclosure, the further arrangement can be configured to generate at least one three-dimensional image of the portion(s) of the sample(s) and to store further data associated with the three-dimensional image as three-dimensional data. In addition, the SLM arrangement(s) can be configured or structured to control a delivery of the radiation(s) in a targeted manner, e.g., by controlling an intensity of the radiation(s) to a particular location on or in the sample(s). Further, the particular arrangement can be configured or structured to trigger the photo activation of the portion(s) concurrently at multiple specified locations. The SLM arrangement(s) can provide a specified spatial profile of the radiation on an image plane of the sample(s).

According still another exemplary embodiment of the present disclosure, a device and a method can be provided for effecting at least one radiation. For example, at least one spatial light modulation (SLM) arrangement can be structured or configured to illuminate microscopic structures within at least one sample using the radiation(s), and/or to adjust a phase of the radiation(s) to impact the sample(s) and obtain at least one depth information therefor. Further, the SLM arrangement(s) can be included in at least one scanless spatial light modulation (SLM)-based microscope arrangement.

According to yet another exemplary embodiment of the present disclosure, a spatio-temporal beam-multiplexed two-photon laser can be moved from neuron to neuron to uncage glutamate and sequentially make each neuron fire, while the resulting synaptic potential in a particular cell is simultaneously recorded. This exemplary configuration can facilitate for a detection of monosynaptically connected cells and for input maps to be generated using a single-cell resolution. Such exemplary method/procedure is also combined with two-photon calcium imaging to manipulate and simultaneously record circuit activity.

These and other objects, features and advantages of the exemplary embodiment of the present disclosure will become apparent upon reading the following detailed description of the exemplary embodiments of the present disclosure, when taken in conjunction with the appended numbered paragraphs.

BRIEF DESCRIPTION OF THE DRAWING(S)

Further objects, features and advantages of the present invention will become apparent from the following detailed description taken in conjunction with the accompanying figures showing illustrative embodiments of the present invention, in which.

Figures 1, 1A, 2:
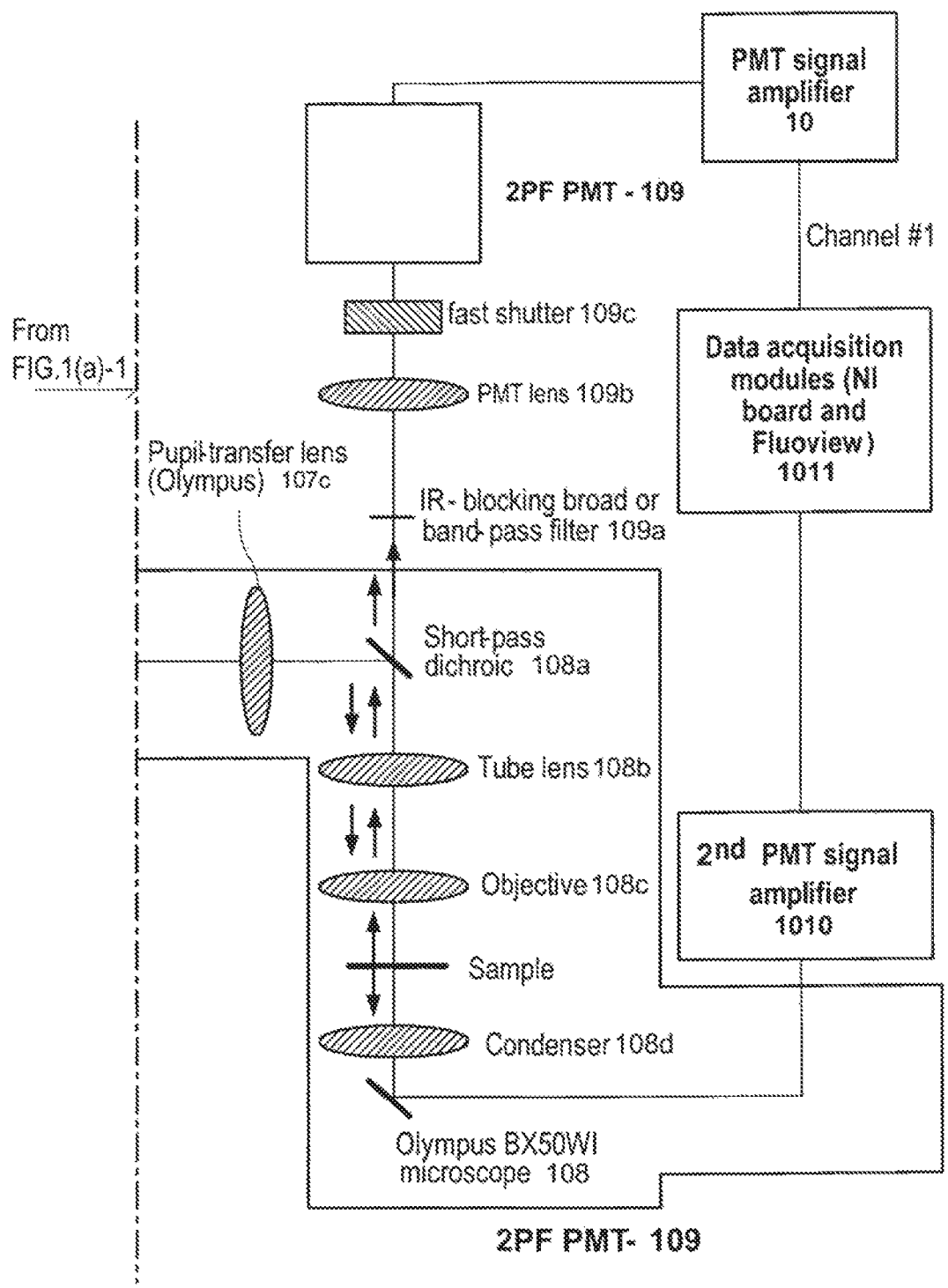
Figure 2R:
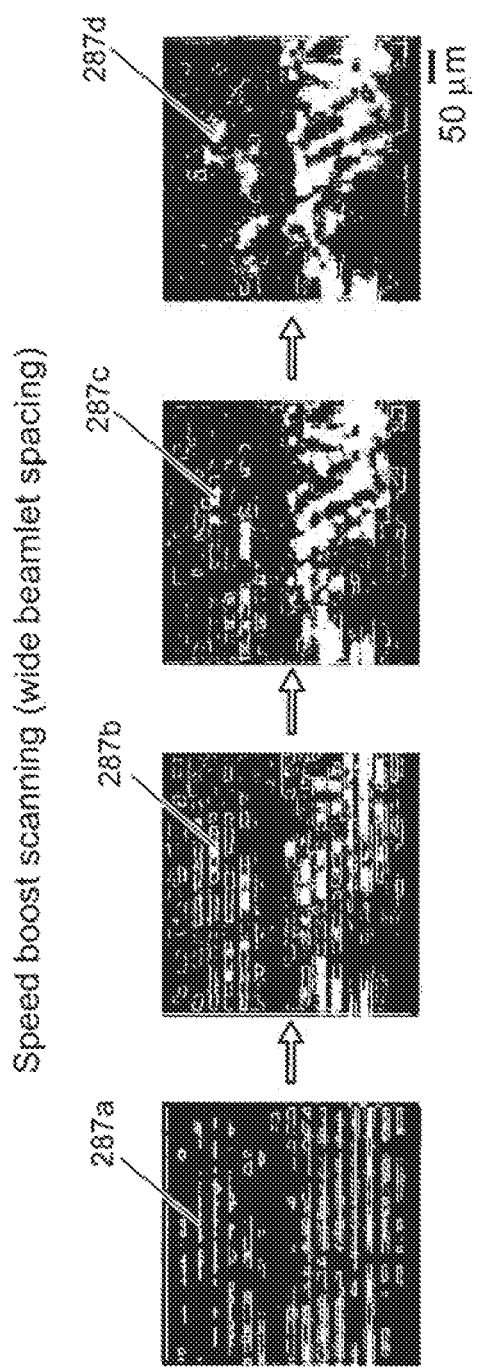
FIG. 2(a) is exemplary illustrations and results for uncaging with temporal beam multiplexing which is associated with exemplary Two-photon photostimulation of MNI-glutamate with beam multiplexing.
FIG. 2(b) is exemplary illustrations and results for a spatial resolution of uncaging which is associated with exemplary Two-photon photostimulation of MNI-glutamate with beam multiplexing.
Figure 2V:
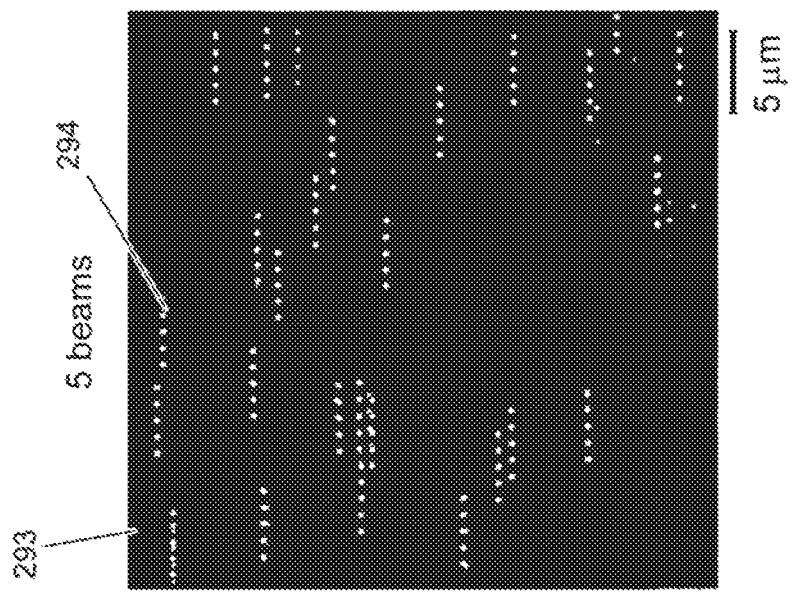
Figure 2U:
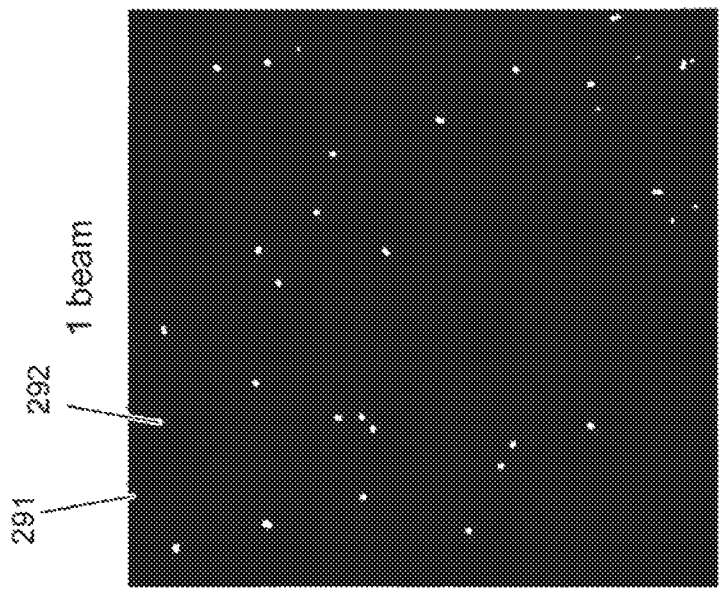
Figure 2W:
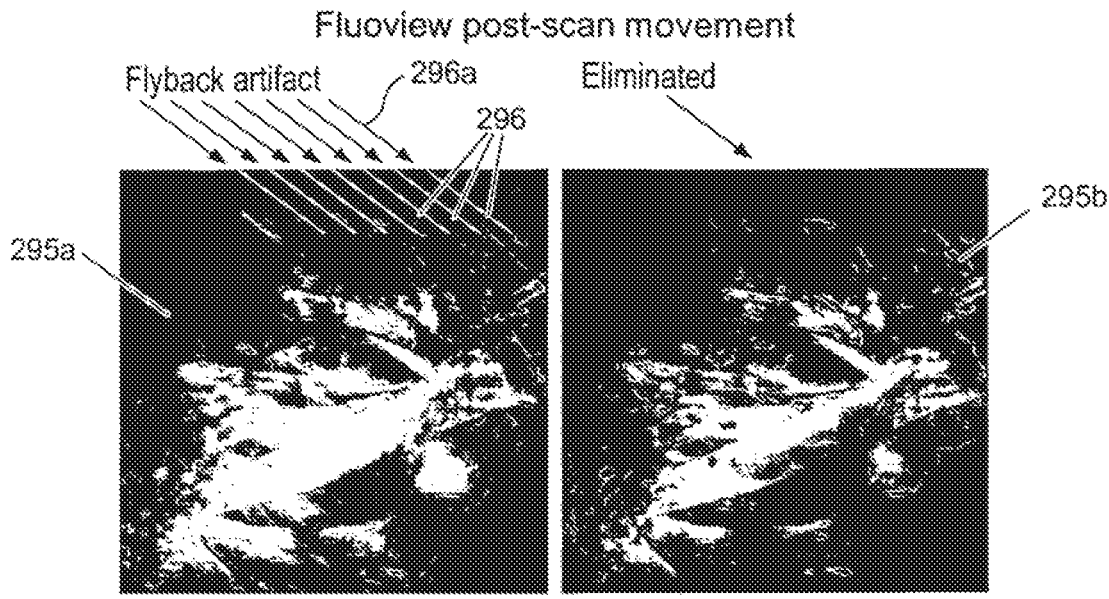
Figure 3A:
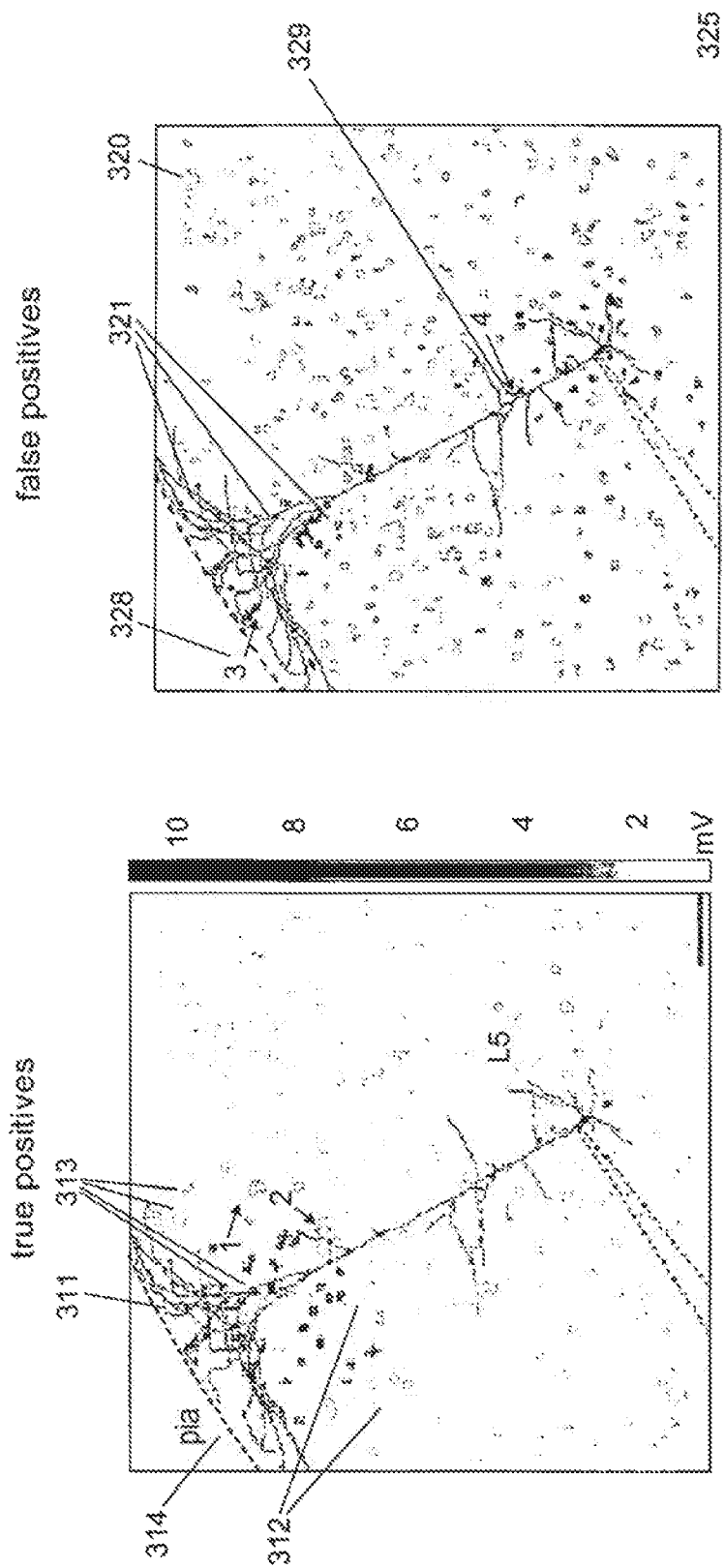
Figure 3B:
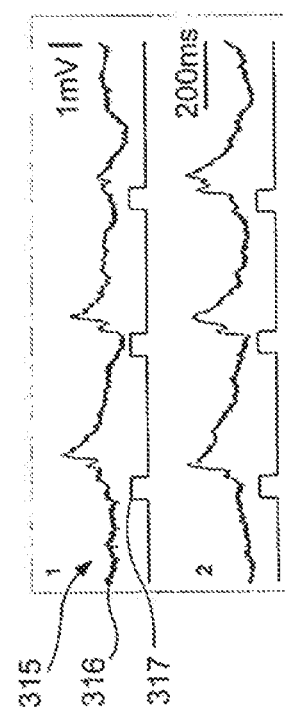
Figure 3D:
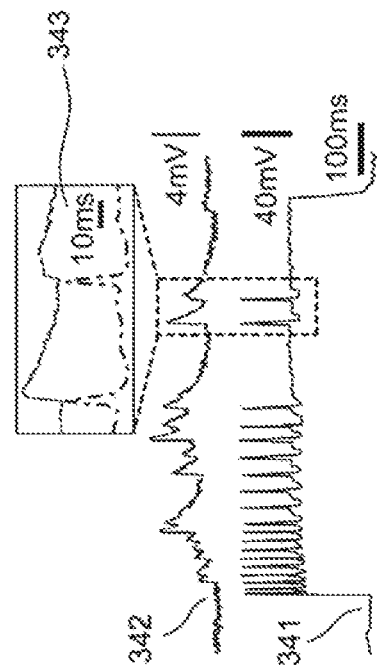
Figure 3F:
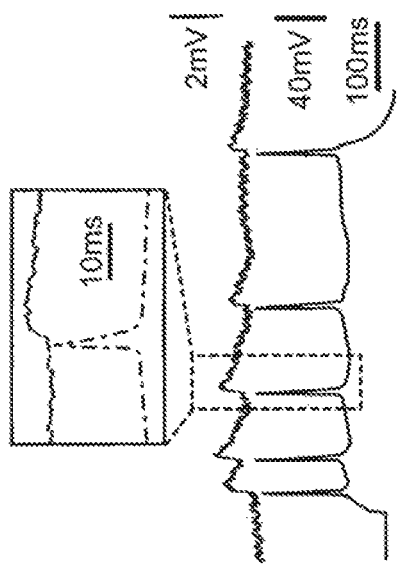
Figure 3C:
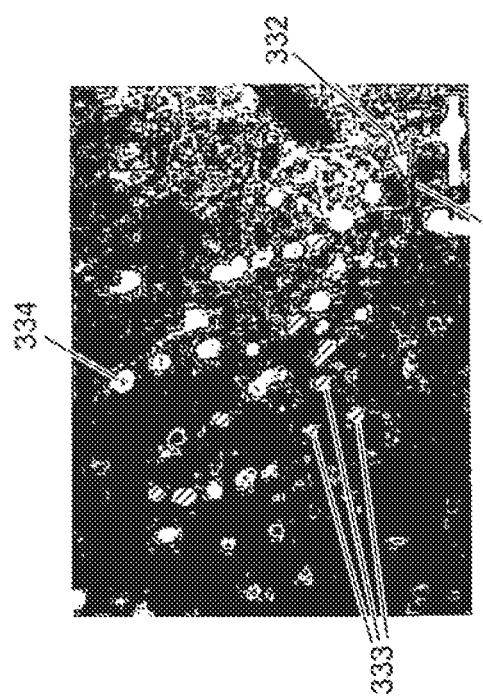
Figure 3E:
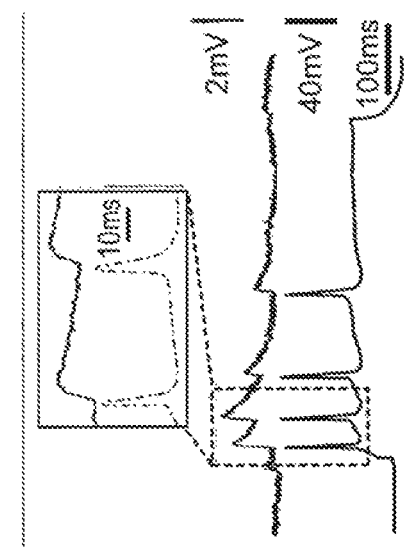
Figure 6A:
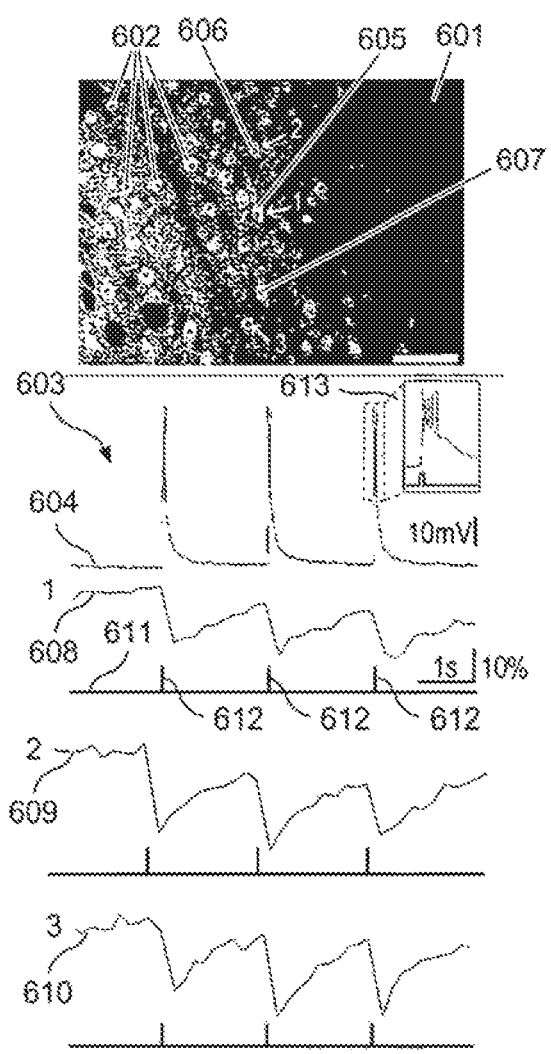
Figure 6B:
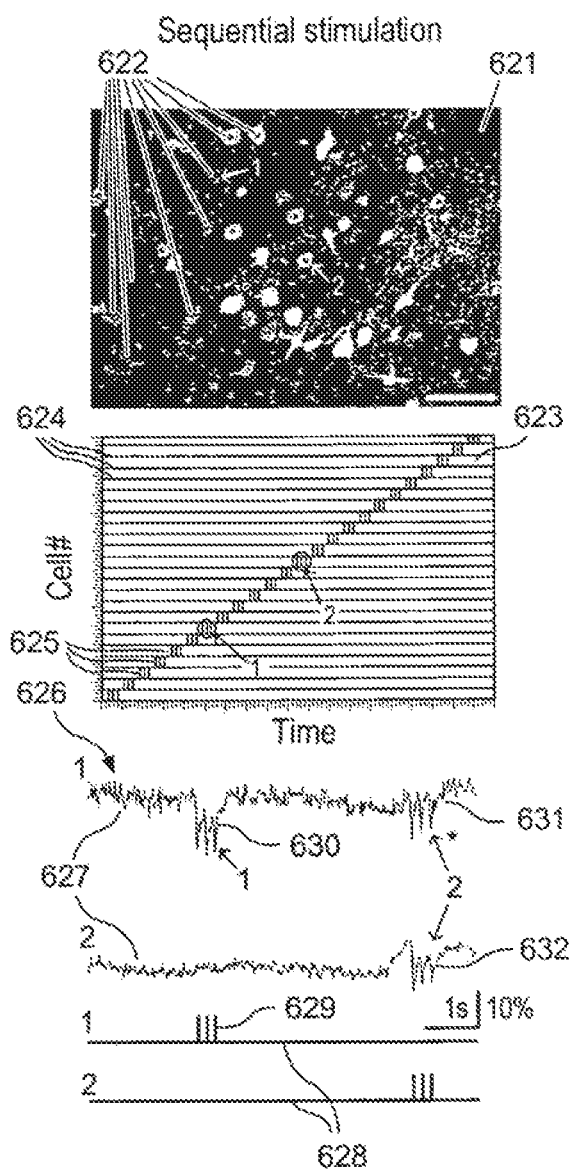
Figure 6C:
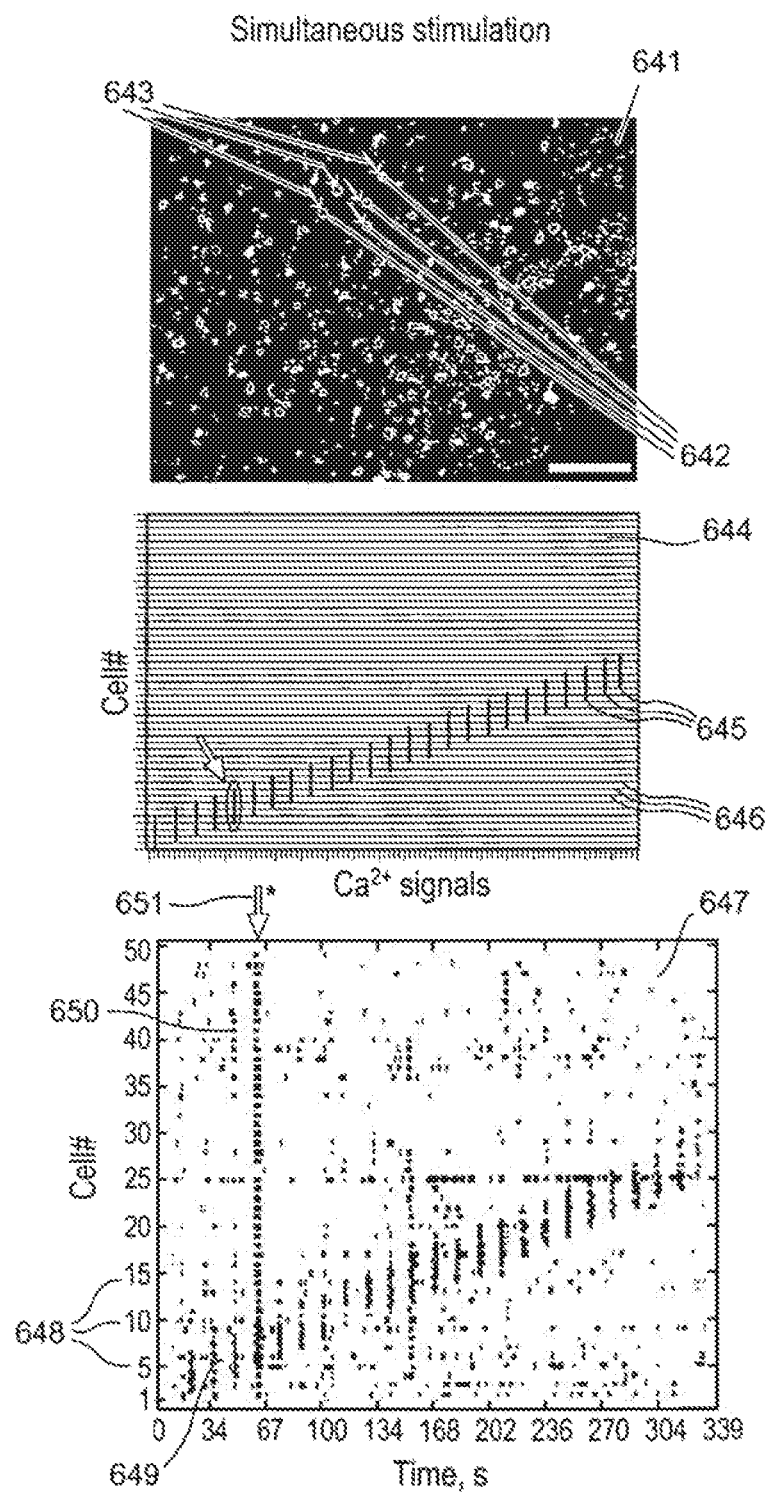
Figure 8:
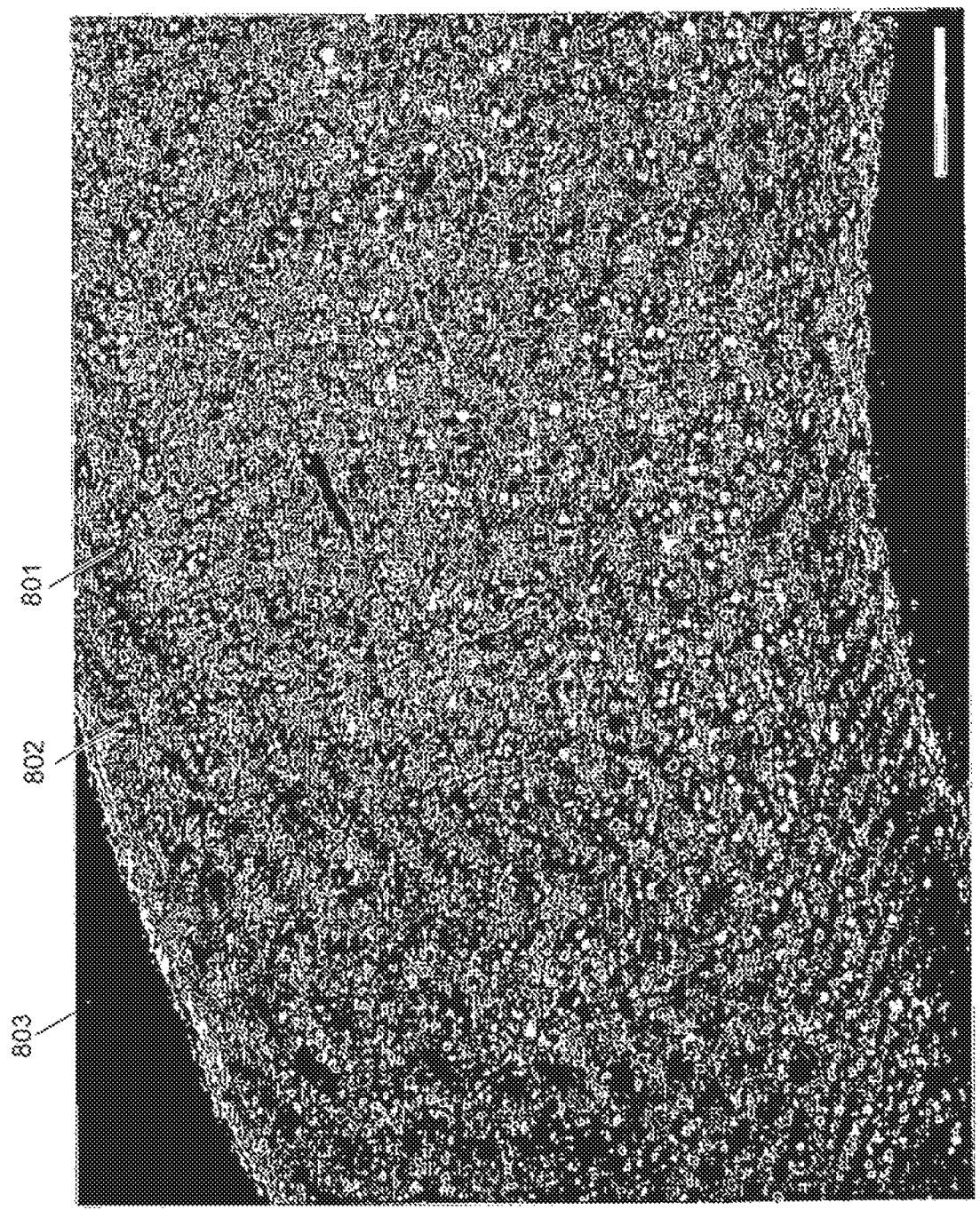
Figure 10:
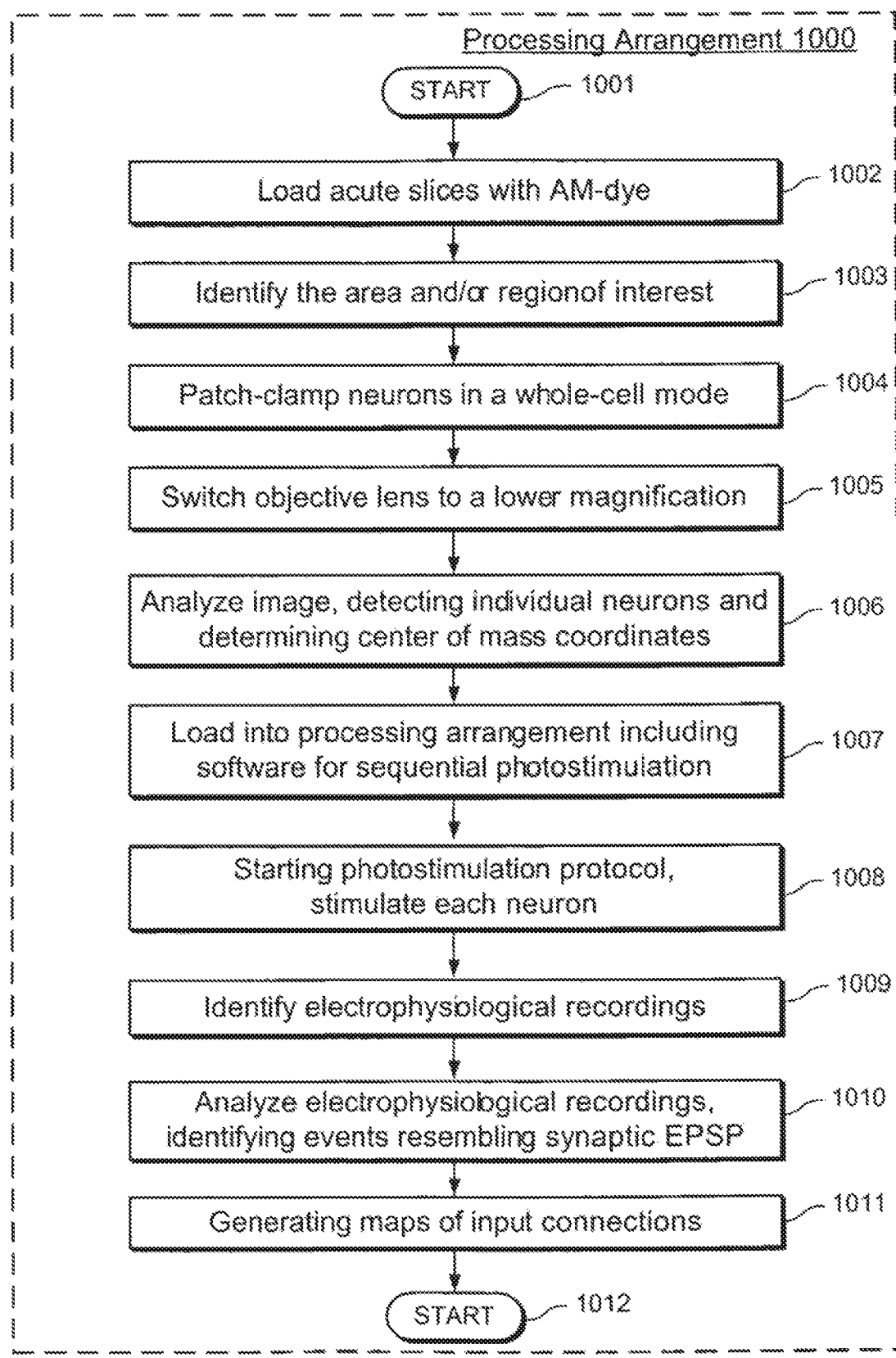
Figure 11:
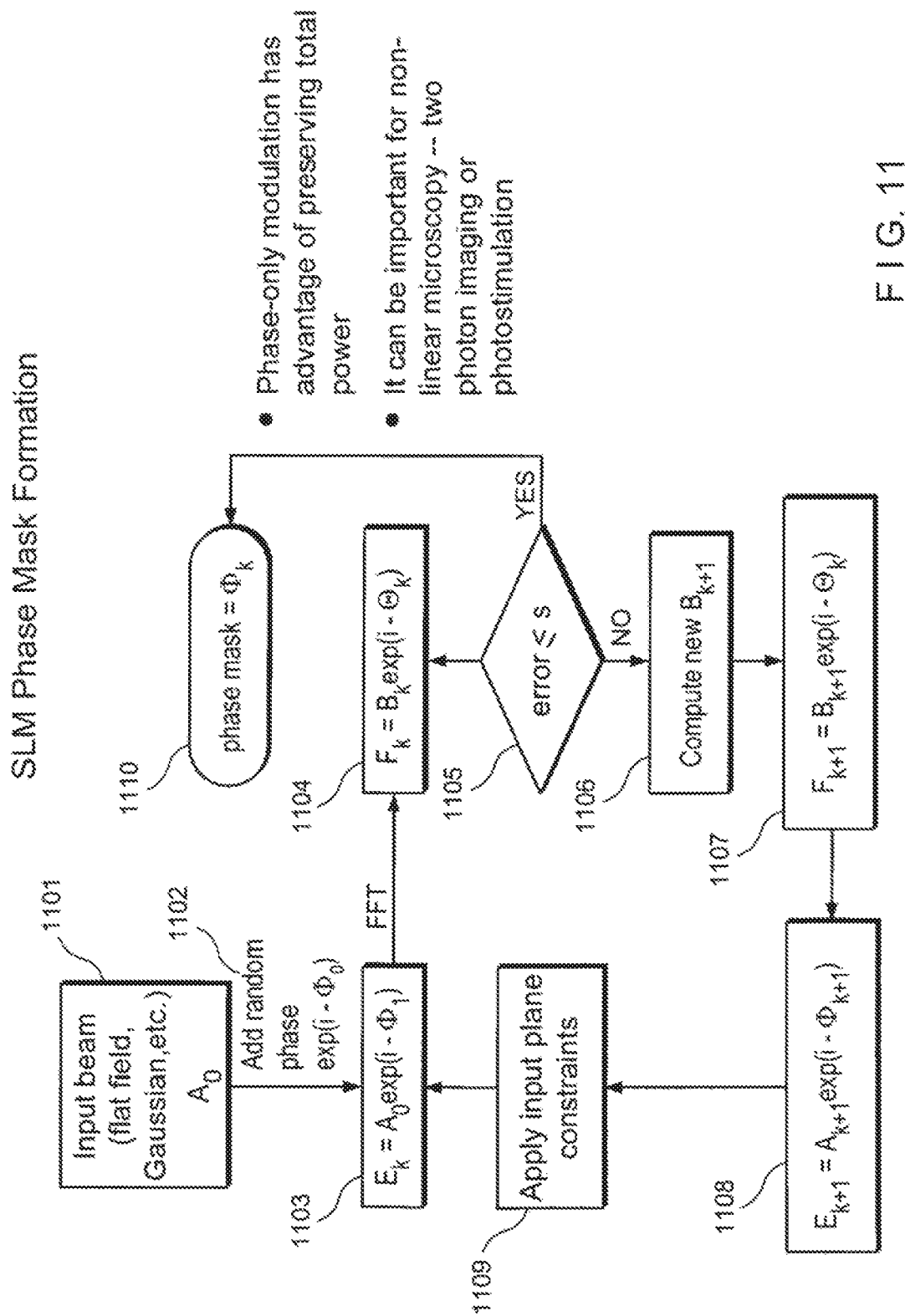
Figure 12A:
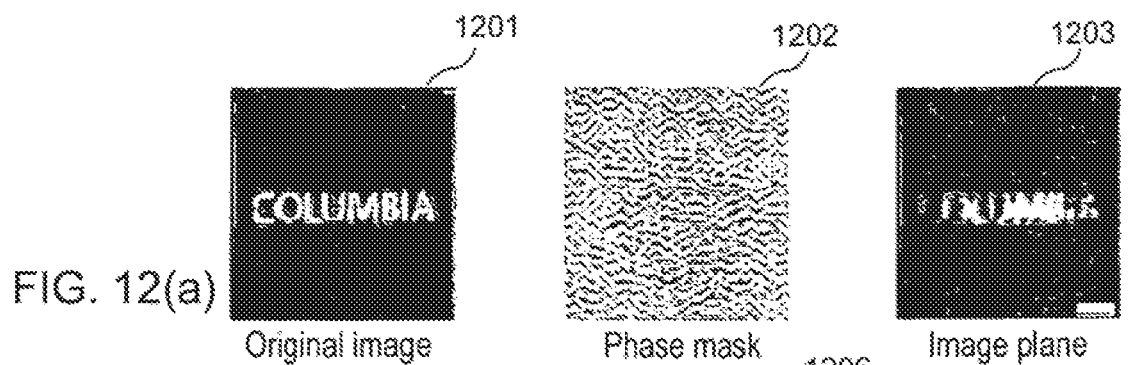
Figure 12B:
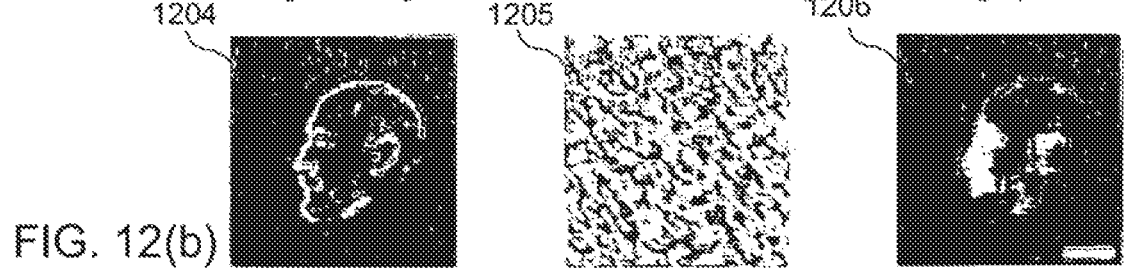
Figure 12C:
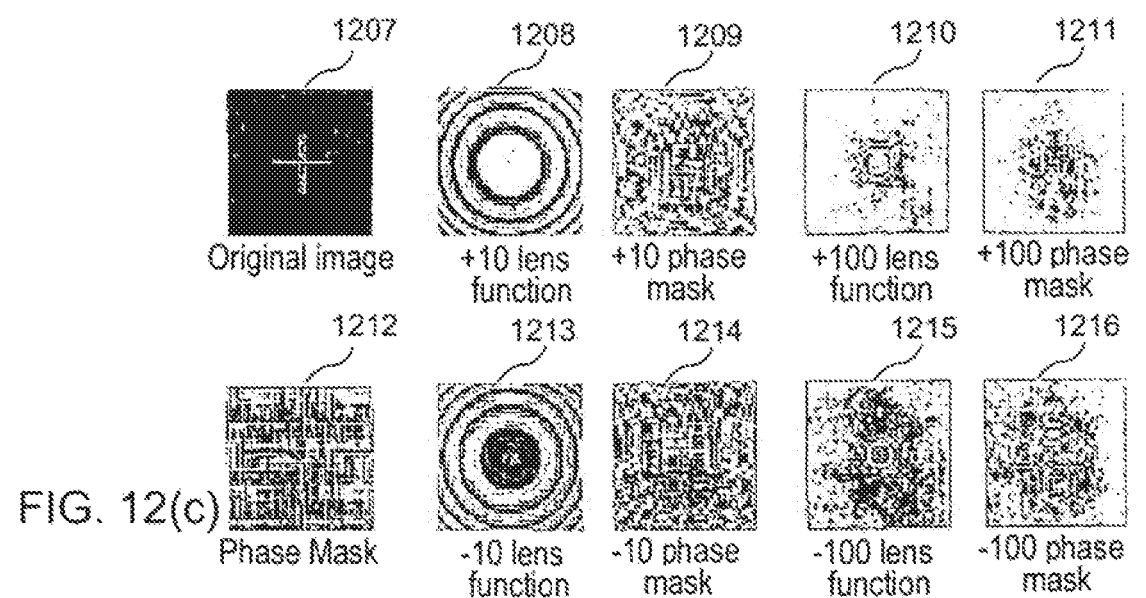
Figure 12D:
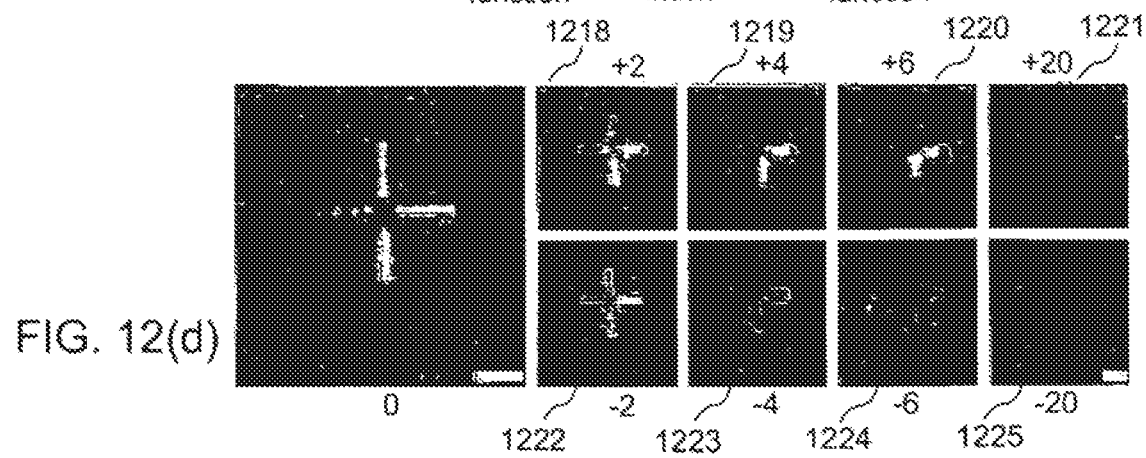
Figure 13:
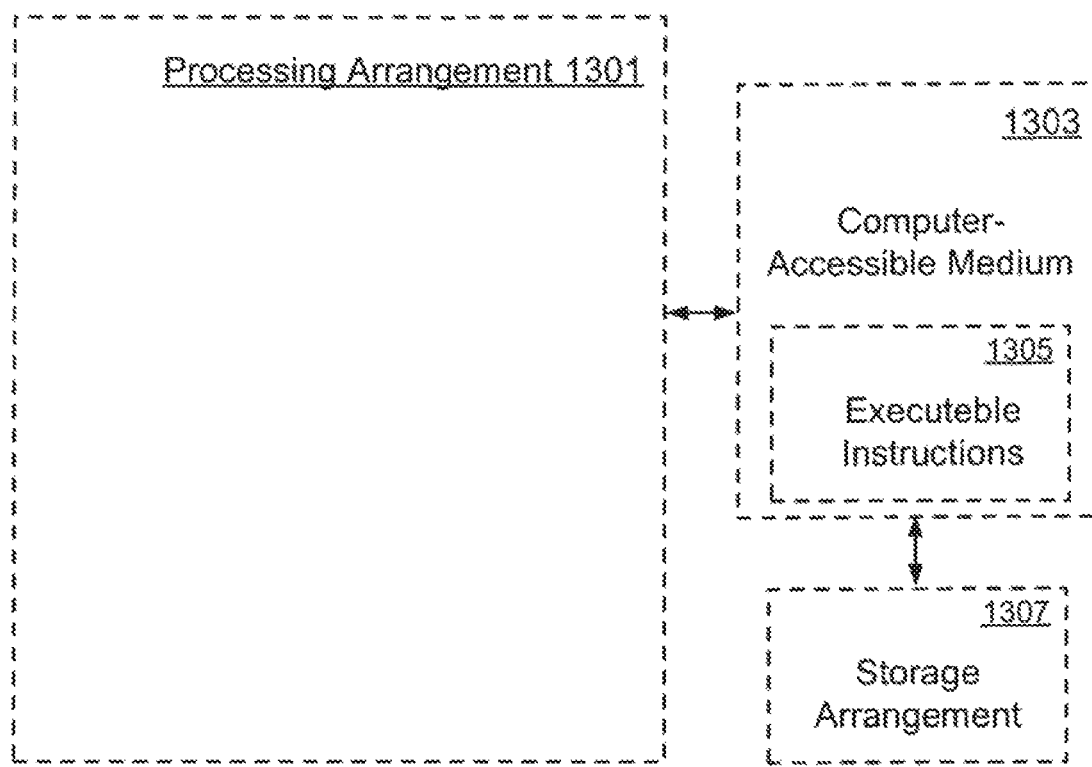

FIGS. 2(c)-(e) are exemplary results for uncaging with diffractive optical element (DOE) spatial beam multiplexing, whereas the illustration of FIG. 2(c) is associated with exemplary Two-photon photostimulation of MNI-glutamate with beam multiplexing;

FIG. 2(f) is exemplary results of a depth resolution of beam multiplexing two-photon uncaging;

FIGS. 2(g) and (h) are schematic representations for utilizing a diffractive optical element (DOE) to enhance two-photon imaging in a horizontal DOE mode according to certain exemplary embodiments of the present disclosure;

FIGS. 2(i) and (j) are schematic representations for utilizing the DOE to enhance two-photon imaging in a vertical DOE mode according to certain exemplary embodiments of the present disclosure;

FIGS. 2(k)-(o) are exemplary results for line scanning with a horizontal DOE mode according to certain exemplary embodiments of the present disclosure;

FIGS. 2(p) and (q) are exemplary results for an enhanced frame scan with the DOE according to certain exemplary embodiments of the present disclosure;

FIGS. 2(r)-(t) are exemplary results for scanning with a vertical DOE mode according to certain exemplary embodiments of the present disclosure;

FIGS. 2(u) and (v) are exemplary results for imaging of sub-micron beads using the DOE according to certain exemplary embodiments of the present disclosure;

FIGS. 2(w) and (x) are exemplary results for scanning in a speed boost vertical DOE scanning mode according to certain exemplary embodiments of the present disclosure;

FIG. 3(a) is an exemplary two-photon input map with a single cell resolution for a layer 5 pyramidal neuron and super-imposed morphological reconstruction of its dendritic tree;

FIG. 3(b) is an exemplary two-photon map with a single cell resolution of false positive signals for the same neuron of FIG. 3(a);

FIG. 3(c) is exemplary graphical results providing that true-positive signals are monosynaptic connections:

FIG. 3(d) is exemplary dual recording from the two exemplary neurons reveals monosynaptic connection;

FIGS. 3(e) and (f) are graphs of exemplary monosynaptically connected true-positive cells from two further experiments;

FIG. 3(g) is an exemplary table illustrating an exemplary analysis of true and false positive responses in accordance with the exemplary embodiment of the present disclosure:

FIG. 4(a) is an exemplary simultaneously acquired graphical input map of all mag-Indo-1AM loaded cells (n=635) detected at a superficial focal plane of the slice (labeled 0 μm);

FIG. 4(b) is an exemplary simultaneously acquired graphical input map of loaded cells (n=546) 45 μm below the exemplary map of FIG. 4(a);

FIG. 4(c) is a graphical illustration of the difference between cell positions at the two exemplary focal planes by the overlay of the exemplary maps of FIGS. 4(a) and 4(b);

FIG. 4(d) is a graphical illustration of an exemplary simultaneously acquired input map in which positions (n=20) that produced true-positive responses in the patched cell while stimulated at focal plane of the exemplary map of FIG. 4(a);

FIG. 4(e) is an exemplary simultaneously acquired input map in which positions (n=17) that generated true-positive responses at focal plane of the exemplary map of FIG. 4(b), using 300 identical coordinates to those used in FIG. 4(d);

FIG. 4(f) is a graphical illustration of an exemplary simultaneously acquired input map in utilizing overlay of inputs maps, which overlap at only two positions, demonstrating the ability of selectively mapping inputs at two adjacent focal planes;

FIGS. 4(g)-(l) are exemplary graphical illustrations of simultaneously acquired input maps from, e.g., four neurons;

FIGS. 5(a)-(g) are consecutive exemplary input maps from the same neuron, obtained sequentially over approximately one hour;

FIG. 5(h) is a graphical illustration of exemplary locations that produced a true-positive response in every map;

FIG. 6(a) is an illustration of an exemplary embodiment of an optical detection of uncaging responses using all-optical stimulation and imaging of network activity;

FIG. 6(b) is an illustration of an exemplary embodiment of a sequential stimulation with a simultaneous imaging;

FIG. 6(c) is an illustration of an exemplary embodiment of another simultaneous stimulation and imaging;

FIG. 7(a) is illustrations of exemplary results for cell detection procedure and scanning path optimization for exemplary targeted imaging of neuronal populations:

FIG. 7(b) is illustrations of exemplary results for calcium imaging of targeted neurons for exemplary targeted imaging of neuronal populations;

FIG. 7(c) is exemplary schematics and exemplary graph results for a single action potential sensitivity of calcium imaging for exemplary targeted imaging of neuronal populations;

FIG. 8 is an exemplary image of loading of cortical slices with mag-Indo-1AM;

FIGS. 9(a)-9(d) are exemplary images mag-Indo-1-AM loads mostly neurons in which slices are simultaneously loaded with mag-Indo1-AM and Sulforhodamine 101 (e.g., SR101, 20 μM) and imaged at their respective exemplary wavelengths;

FIG. 10 is a flow diagram of an exemplary Photostimulation procedure in accordance with certain embodiments of the present disclosure which can be executed by a processing arrangement;

FIG. 11 is a flow diagram of an exemplary embodiment of a method for a SLM phase mask formation in accordance with the present disclosure;

FIGS. 12(a)-12(d) are exemplary SLM light patterning and depth focusing images and sequences for obtaining thereof result from exemplary experiments in accordance with the exemplary embodiment of the present disclosure; and FIG. 13 is a block diagram of a system or an arrangement configured in accordance with certain exemplary embodiments of the present disclosure.

Throughout the figures, the same reference numerals and characters, unless otherwise stated, are used to denote like features, elements, components or portions of the illustrated embodiments. Moreover, while the subject disclosure will now be described in detail with reference to the figures, it is done so in connection with the illustrative embodiments. It is intended that changes and modifications can be made to the described exemplary embodiments without departing from the true scope and spirit of the subject disclosure as defined by the appended claims.

DESCRIPTION OF EXEMPLARY
EMBODIMENTS OF THE DISCLOSURE

System, device and method to perform according to exemplary embodiments of the present invention can be provided which facilitate photostimulation and imaging of the activity of large neuronal populations, using a single two-photon laser in accordance with some exemplary embodiments of the present disclosure.

Exemplary Optical Design and Embodiments of Two-Photon Microscope

Exemplary software executed by a processing arrangement (e.g., a processor) in accordance with an exemplary embodiment of the present disclosure can facilitate a positioning of a laser beam in any point in the field of view and fast switching between, e.g., two-photon calcium imaging of Indo-1AM and two-photon uncaging of MNI-caged glutamate (see M. Canepari, supra; G. C. R. Ellis-Davies, supra) on individual neurons, causing them to fire action potentials. An electrooptical modulator can be used for switching between two levels of laser light intensity; a lower intensity for imaging and a higher level for photostimulation/uncaging. Thus, a laser beam (e.g., at about 725 nm) can be used to trigger and monitor circuit activity with three-dimensional precision.

For example, exemplary embodiments of the system and device according to the present disclosure can modify a two-photon fluorescence (2PF) and second harmonic generation (SHG) microscope. (See V. Nikolenko, supra; A. Majewska, G. Yiu, and R. Yuste, Pflügers Archiv—Eur. J. Physiol. 441 (2-3), 398 (2000)).

Figures 1, 1A:
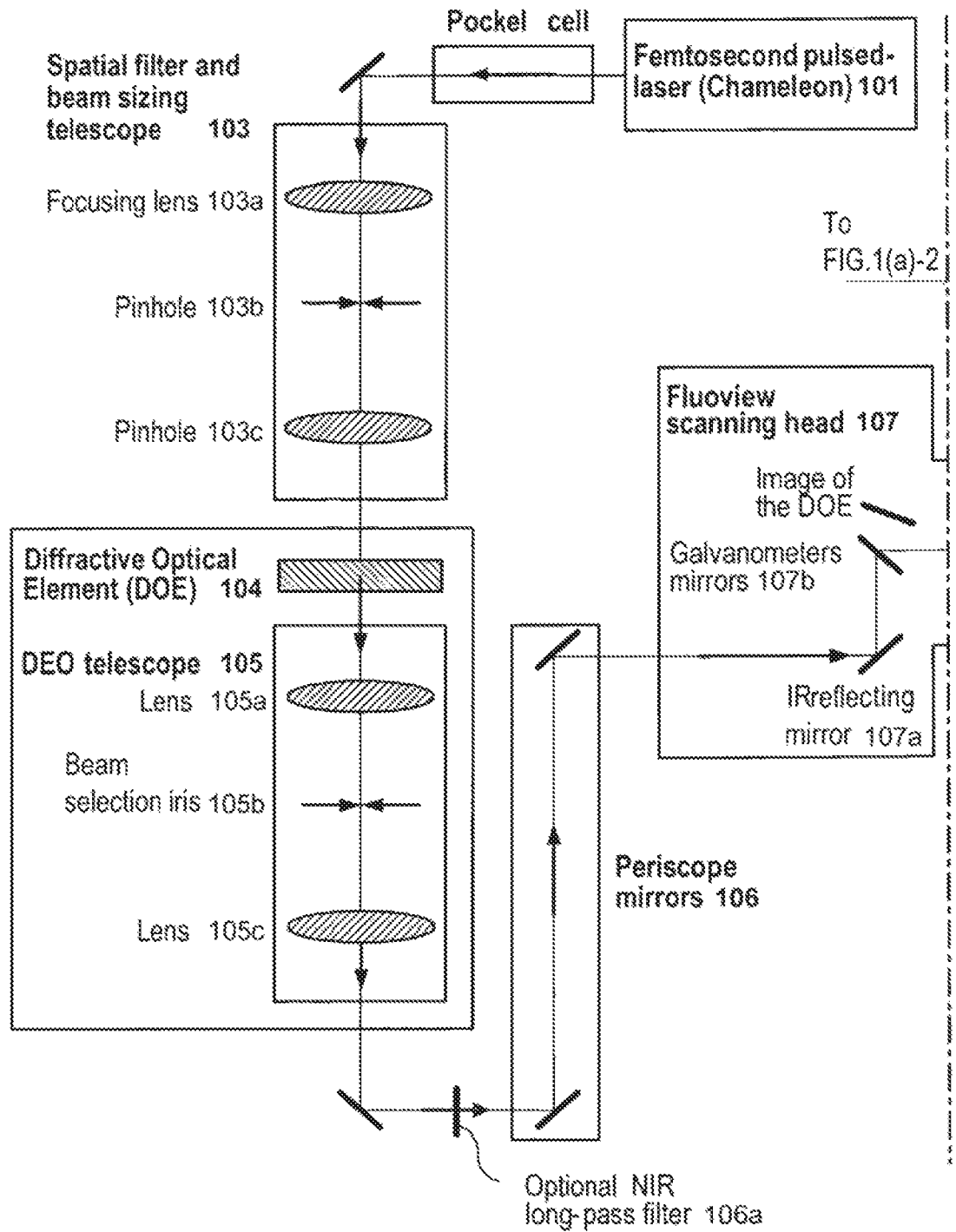
FIG. 1(a) is a diagram of an optical system and a microscope system/arrangement of a microscope according to an exemplary embodiment of the present disclosure.

FIG. 1(a) shows a diagram of an exemplary embodiment of an optical system and a microscope system of a microscope according to the present disclosure.

For example, according to certain exemplary embodiments, an exemplary microscope, as shown in FIG. 1(a), can include (but not limited to) the following exemplary components: a Ti:Sapphire laser 101, an electro-optical modulator (Pockels Cell) 102, beam-shaping optics (telescope/spatial filter) 103, diffractive optical element (DOE) optics including DOE 104 and DOE telescope 105, periscope mirrors 106, a scanner 107, an upright microscope 108, and a photomultiplier (PMT) based 2PF/SHG detection system including 2PF PMT 109, PMT signal amplifiers 110, a data acquisition module 111, and a lamp for brightfield illumination or a second PMT for 2PF/SHG 112. Exemplary beam-shaping optics 103 can include a focusing lens 103, a pinhole 103b and a lens 103c. Exemplary DOE telescope 105 can include a lens 105a, a beam selection iris 105b and another lens 105c. Exemplary scanner 107 can include an IR-reflecting mirror 107a, galvanometers mirrors 107b and a pupil-transfer lens 107c. An exemplary upright microscope 108 can include a short pass dichroic 108a, a tube lens 108b, an objective 108c and a condenser 108d. Exemplary 2PF PMT 109 can include an IR=blocking broad or band-bass filter 109a, a PMT lens 109b and a fast shutter 109c.

According to certain exemplary embodiments, one or more of the following components can be used: a tunable Ti:Sapphire (e.g., Chameleon; Coherent, Santa Clara, Calif.), a model 350-160 Pockels Cell driven by a model 275 linear amplifier (Conoptics, Inc Danbury, Conn.), intermediate dielectric mirrors (e.g., BB1-E02 from Thorlabs, Newton, N.J.) and a diffractive optical element (e.g., fused silica, SLH-505Xa-(0.23)-(780) Stocker Yale Canada Inc., Dollard-Des-Ormeaux, Quebec, Canada). Other elements of the optical path can be assembled from standard components (e.g., Thorlabs). The upright microscope (e.g., Olympus BX50WI) was equipped with water-immersion objectives (e.g., lenses from Olympus).

For example, a LUMPlanFl/IR 40×0.8NA lens (e.g., IR2 coating) can used for targeting cells in DIC for patch-clamping and high-resolution two-photon imaging and photostimulation of small number of neurons, whereas low-magnification objectives (e.g., UMPlanFI 20×0.5NA, XLUMPlanFI 20×0.95NA and UMPlanFI 10×0.3NA) can be used for imaging/photostimulation of neuronal populations. A short-pass dichroic mirror (e.g., 650DCSP; Chroma Technology, Rockingham, Vt.) can be placed inside the standard trinocular tube of the exemplary microscope. An IR-blocking filter (e.g., BG39 from Chroma Technology) can be placed in front of the PMT to filter out remaining infrared light scattered from the excitation path. As a detector, a cooled GaAs PMT (e.g., H7422P-40; Hamamtsu Corp., Japan) can be used with an additional amplifier (e.g., PE 5113; Signal Recovery AMETEK Advanced Measurement Technology, Wokingham U.K.). A fast mechanical shutter (e.g., LS6T2; driven by a VCM-DI; Vincent Associates, Rochester, N.Y.) can be used to protect the PMT from overloading in simultaneous imaging/uncaging examples.

PMT signals can be digitized by, e.g., the Fluoview board in raster mode or by an external A/D board in vector-mode (e.g., NI PCI-6052E National Instruments, Austin. Tex.). This board can also modulate laser intensity through the Pockels Cell, according to the analog output from custom software in accordance with some exemplary embodiments of the present disclosure. The same exemplary software can control the position of the scan mirrors through direct calls of functions in the original library files (e.g., gbx.dll; FV200 Olympus Fluoview Basic). (See V. Nikolenko, supra). Exemplary software according to the present disclosure can be executed by a processing arrangement (e.g., a processor, computer, etc.), which can be provided in, e.g., a LabView programming environment (National Instruments) and communicate with integrated software routines for computationally intensive procedures such as cell contours detection or traveling salesman path computation (e.g., MATLAB; The Mathworks, Natick, Mass.).

Figure 1B:
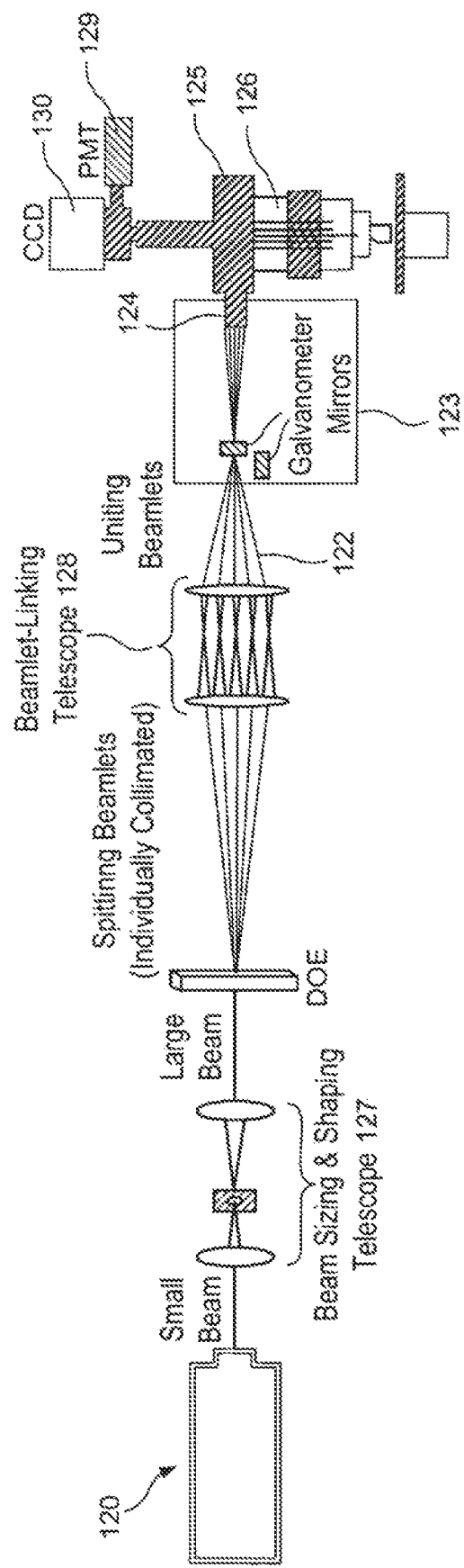
FIG. 1(b) is a diagram of an arrangement which includes an exemplary beam splitting configuration that can use a diffractive optical element according to an exemplary embodiment of the present disclosure.

FIG. 1(b) shows a diagram 120 demonstrating an implementation of the exemplary arrangement according to the present disclosure which facilitates beam splitting using a DOE 121 according to an exemplary embodiment of the present disclosure. The DOE 121 can be, e.g., a DOE 104 as shown and described above with reference to FIG. 1(a). Beams 122 can be brought together onto galvanometer mirrors 123, which can scan and transmit beams 124 for excitement of a sample. The exemplary telescope 125 can change the size of the outgoing beamlets 126 so a pre-sizing telescope 127 can be used before the DOE-telescope complex 128. Image collection can be performed using either a photomultiplier tube (PMT) 129 and/or a CCD camera 130, for example.

Figure 1C:
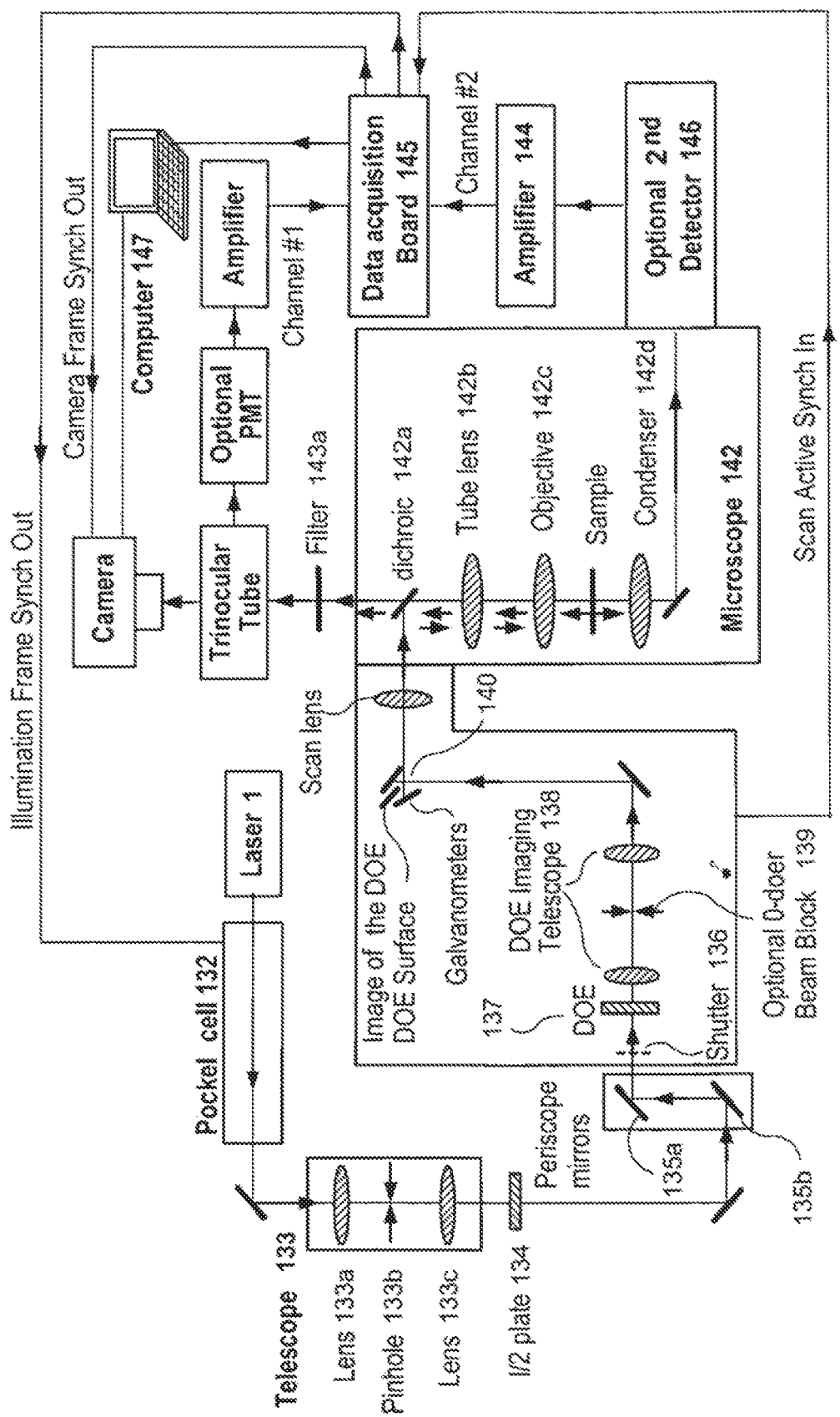
FIG. 1(c) is a diagram of another exemplary embodiment of the optical system and the microscope system/arrangement of the microscope according to the present disclosure.

FIG. 1(c) shows diagram of another exemplary embodiment of the optical system and the microscope system of a microscope according to the present disclosure. For example, such exemplary optical system and microscope system can include, e.g., a source (ultrafast laser) 131, Pockels cell 132, beam-sizing telescope 133, half-wave plate 134, periscope 135, slow mechanical safety shutter 136, DOE 137, DOE imaging telescope 138, an optional 0-order beam block 139, scanning mirrors 140, a scan (or "pupil-transfer") lens 141, an upright microscope 142, detection system 143, current to voltage converters/signal amplifiers for PMT detection, Data acquisition unit 145, Optional 2nd detector (Camera or PMT) 146, and a PC for data acquisition and equipment control 147.

According to certain exemplary embodiments of the present disclosure, the Pockels cell 132 can be controlled by a voltage input and regulate excitation laser intensity, and can work essentially as a fast "shutter". A beam-sizing telescope 133, in combination with the DOE 108, can provide a beam of a convenient size at the input port of the microscope to properly fill the back aperture of the microscope objective. Depending on type of DOE used, half-wave plate 134 can be used for changing diffraction efficiency and making intensity of a 0 diffraction order beamlet equal to other beamlets. A periscope 135 can include mirrors to deliver the laser beam to the input port of an upright microscope. A DOE imaging telescope 138 can relay the image of the DOE 137 surface to approximately the plane of the scanning mirrors 140. Instead of or in addition to, e.g., using the optional 0-order beam block 139, it is possible to use a thin metal rod for such exemplary purpose, which can be used with DOEs that are designed or structured to produce a pattern without a beamlet in the center location, and which produce an unintended zero-order beamlet.

The exemplary upright microscope 142 can include a standard dichroic 142a for two-photon fluorescence detection; a tube lens 142b, a microscope objective 142c and microscope bright field illumination condenser 142d. The detection system 143 can detect shorter-wavelength light, and include, e.g., a band-pass filter 143a to include only emission-wavelength light; a standard microscope trinocular tube 143b to switch between imaging ports (one port can be used for traditional whole-filed PMT detection, while another for fast imaging using the camera); a cooled CCD camera 143c, and an optional PMT for traditional slow scanning imaging 143d. The optional 2nd detector (e.g., camera or PMT) 146 can be used for gathering optical signals in a forward direction (e.g., two-photon excited fluorescence or second harmonics generation (SHG) signal).

A premise of using diffractive spatial light modulators can be that many complex optical systems (e.g., excitation optical path of laser-scanning microscopes, which can be used in biological imaging) can be considered as wavefront modulators implemented by combination of, e.g., lenses, scanning systems etc. for the purposes of many different imaging modalities. For example, for complex optical systems that are based on non-linear phenomena (e.g., two-photon fluorescent or second harmonic generation imaging, etc.), the excitation pathway can be what defines points of the sample that are excited if a traditional scanning approach is employed. A microscope objective can operate as a type of modulator, and transform a collimated beam from a laser source (e.g., a plane electromagnetic wave) into a spherical electromagnetic wave that converges into a focus point thus generating an optical signal from that point.

Figure 1D:
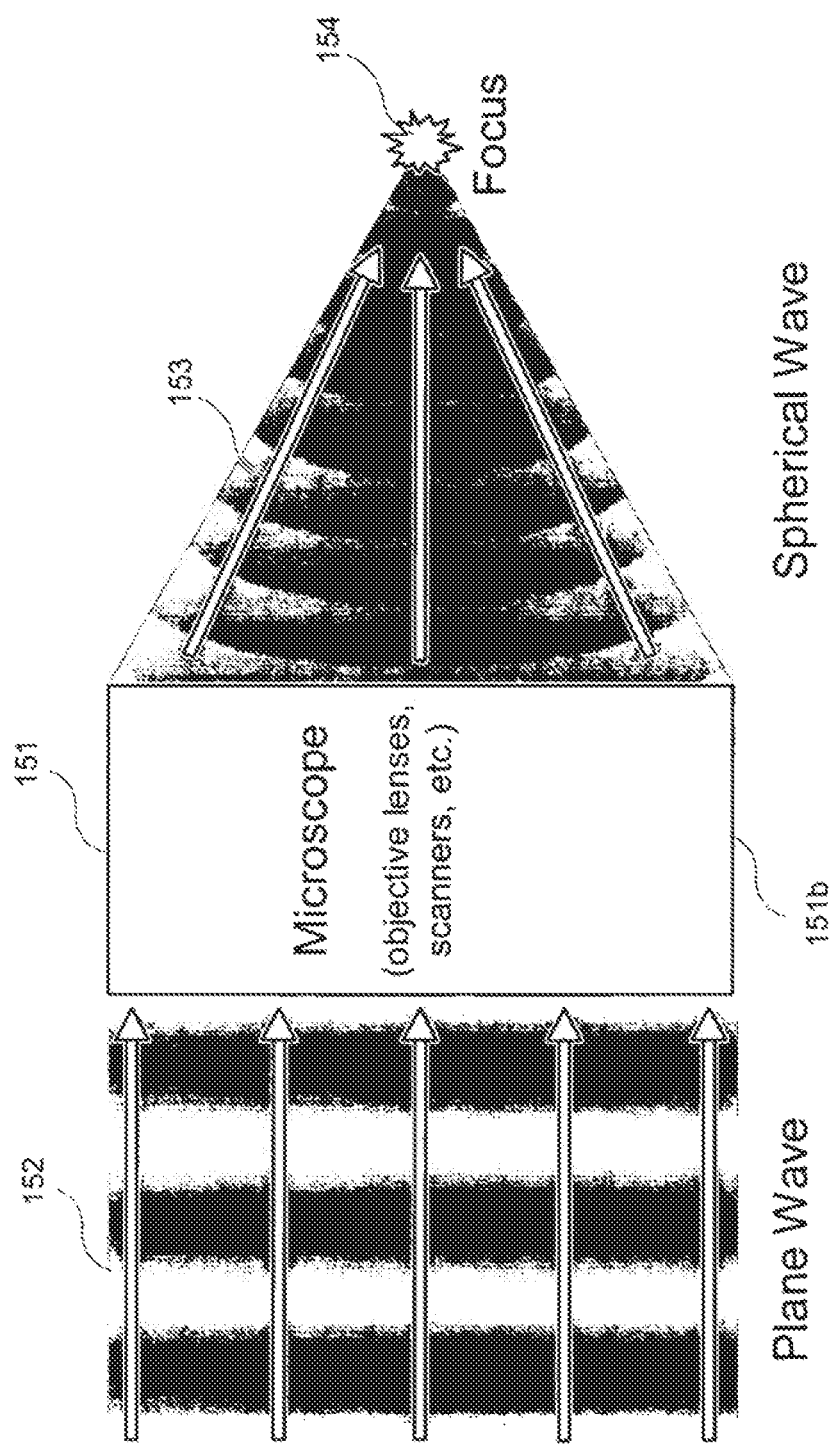
FIG. 1(d) is a diagram of a further exemplary embodiment of the optical system and the microscope system/arrangement according to the present disclosure that demonstrates how an excitation beam can be stirred to move a focus point on a sample.

FIG. 1(d) shows an exemplary embodiment of a microscope 151 according to the present disclosure that can include, e.g., a scanning system 151(a) (including, e.g., galvanometer mirrors) that can stir an excitation beam 152, 153 (e.g., change the direction of propagation of the plane wave 152) and thus move the focus point 154 on the sample plane to gather an optical signal from different points of the sample. Depending on the imaging modality that is used, an optical signal can also be an electromagnetic wave that can be detected by imaging optics such as, e.g., photomultipliers or a camera.

In addition to a basic optical transformation as described herein (e.g., of a plane wave 152 into a spherical wave 153 by an objective 151(b)), a lens can serve a more general function of an optical Fourier operator, performing transformation of spatial frequencies of electromagnetic waves produced by sources located at the planes far away from the lens (e.g., approximately plane waves) into positions of the virtual point sources located on the focal plane and that correspond to wavefronts after the lens (e.g., spherical waves). Additional information and examples of an optical Fourier transformation can be found in, e.g. Lehar, Steven, "An Intuitive Explanation of Fourier Theory," available at http://sharp.bu.edu/~slehar/fourier/fourier.html, last accessed Sep. 23, 2009.

Accordingly, a microscope can be a sophisticated optical modulator that can change a wavefront of light that comes from a source to a wavefront in a sample in different ways in order to perform imaging. Accordingly, in certain exemplary embodiments of the microscope arrangement according to the present disclosure, a whole excitation optical pathway (or at least the dynamic part thereof that can stir a beam), can be replaced by a single element diffractive optical modulator in order to implement new complicated imaging strategies, such as, e.g., to excite several points at the same time. Such exemplary modulators that are capable of, e.g., almost universal transformation of optical wavefronts can be called diffractive spatial light modulators (SLM).

An example of a SLM that can be used in accordance with certain exemplary embodiments of the present disclosure can be based on a two-dimensional matrix of nematic liquid crystals, in which each pixel can be used to locally retard the wavefront. One exemplary feature of an exemplary SLM can be that it may exclude moving parts. Thus, beam scanning, for example, can be performed by merely sending different patterns to the modulator. An exemplary SLM can also be suited for non-linear imaging because the dispersion of ultrafast pulses can be considered to be negligible.

Figure 1E:
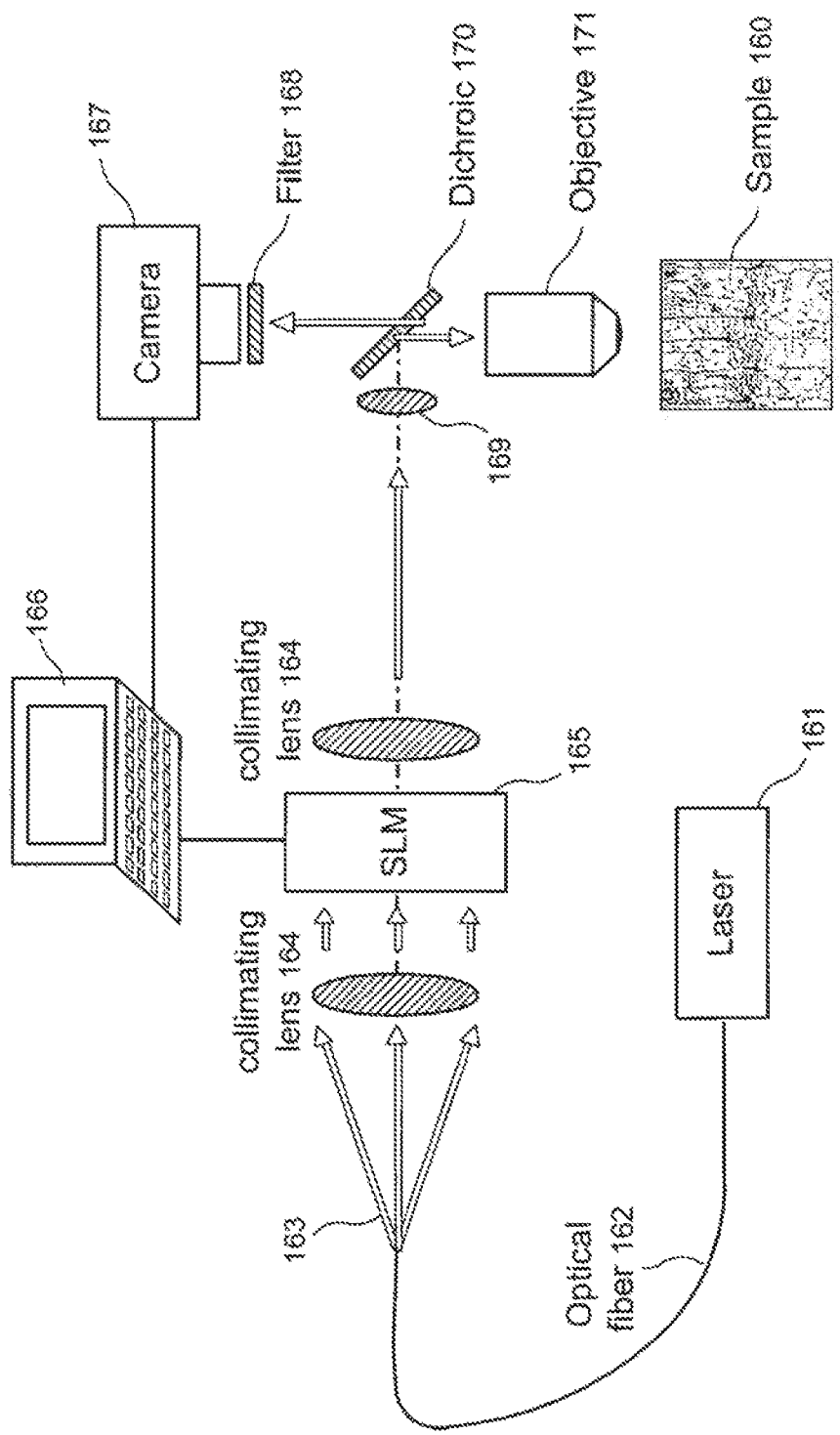
FIG. 1(e) is a diagram of still another exemplary embodiment of the optical system and the microscope system/arrangement of the microscope according to the present disclosure using an SLM.

FIG. 1(e) shows a diagram of another exemplary embodiment and design of the optical system and the microscope system/arrangement according to the present disclosure that uses the SLM. For example, this exemplary optical system and microscope system can include, e.g., a laser source 161, optical fiber 162, collimating lenses 164, an SLM 165, a computer 166, a camera, 167, a filter, 168, a lens 169, a dichroic 170 and an objective 171 under which a sample 160 can be placed.

As discussed herein, by shifting a complexity from hardware (e.g. optical scheme) to software (e.g., calculating phase masks), an exemplary SLM-based microscope in accordance with the present disclosure an be created, which can have a minimal number of traditional optical elements (e.g., lenses) and therefore be simple optically.

Figure 1F:
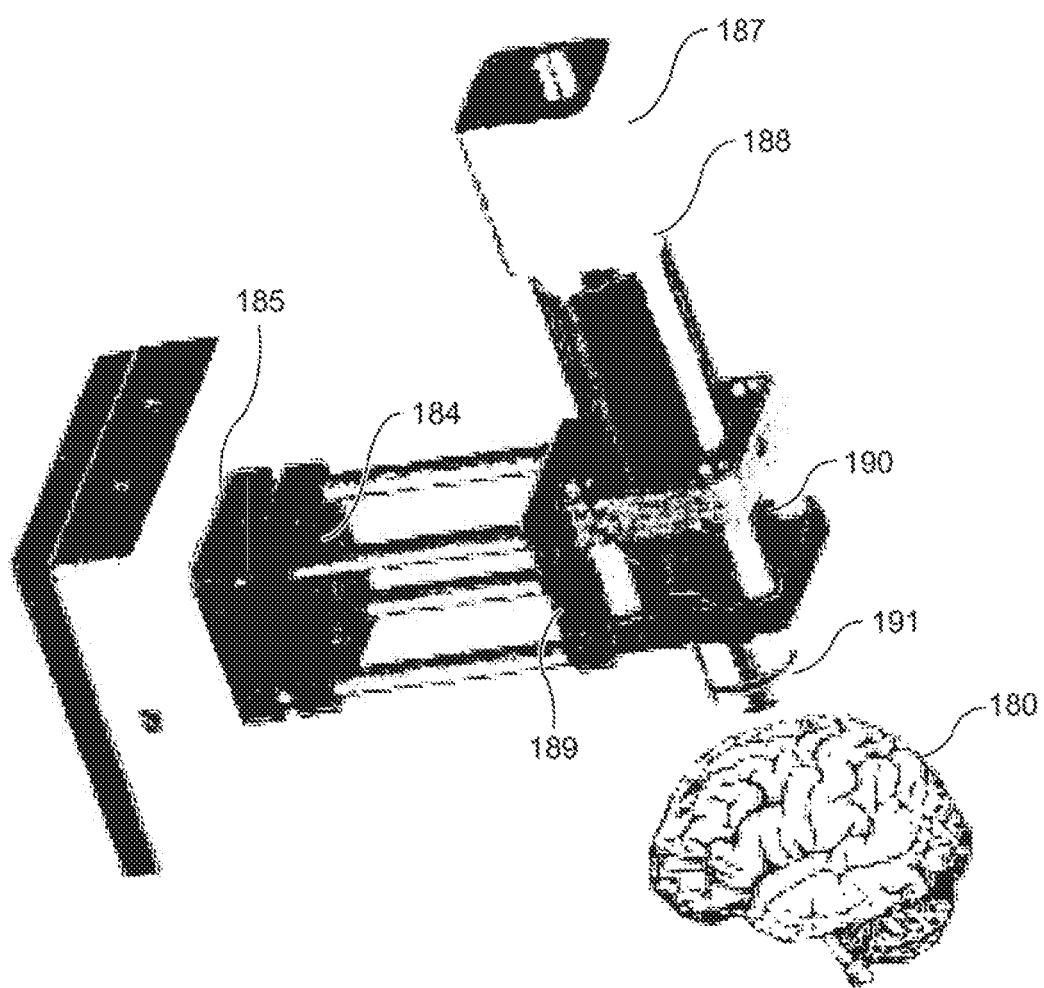
FIG. 1(f) is an illustration of a still further exemplary embodiment of the optical system and the microscope system/arrangement according to the present disclosure of a small, lightweight and portable microscope using an SLM.

FIG. 1(f) shows an illustration of an SLM-based microscope in accordance with certain exemplary embodiments of the present disclosure. For example, as shown in FIG. 1(f), the exemplary optical system and microscope system/arrangement can include, e.g., collimating lenses 184, an SLM 185, a camera, 187, a filter 188, a lens 189, a dichroic 190 and an objective 191 under which a sample 180 can be placed, for example. The exemplary microscope illustrated in FIG. 1(f) can be of the same as or of different from the exemplary arrangement of FIG. 1(e).

These exemplary microscopes can, e.g., improve power efficiency and be so small and lightweight that they can be handheld. They can also be relatively inexpensive so as to provide for greater usage in a wider variety of applications than can be possible with traditional microscopes as well as larger exemplary microscopes in accordance with the certain exemplary embodiments of the present disclosure. For example, usage and applications can include, e.g., SLM two-photon (2P) photostimulation and/or imaging (with e.g., less power constraints), one-photon (1P) photostimulation such as for in-vivo and/or other medical applications, drug discovery and/or delivery, and in-vivo 2P microscopy. It can also attract users who may otherwise not use 2P and imaging in general because of perceived technical complexity with heretofore existing technology.

It is possible to separate the issues of excitation and detection because the goals (e.g., of end-users) for optical performance can be different. For example, an excitation path can provide power delivery for purposes of, e.g., photostimulation (by e.g., photoactivatable compounds, genetically modified neurons, etc.) or for multi-spot imaging. Photoactivatable compounds can include, e.g., most any compound that can be activated by electromagnetic waves. In addition to activation, photostimulation (or photoactivation) can include, e.g., inhibition, deactivation and changing biological metabolic processes inside cells, etc.

According to certain exemplary embodiments of the present disclosure, the SLM itself can be structured or configured to perform the functionality of complex optics, as discussed above. For example, an exemplary virtual lens can be provided by an exemplary SLM with a numerical aperture of, e.g., approximately 0.1NA (e.g., for an exemplary SLM of a given aperture/size that has HDTV resolution). According to further certain exemplary embodiments of SLIM, a numerical aperture can be larger. Whether acceptable for 2P applications, the size of a numerical aperture can be less significant for 1P applications. For example, a larger numerical aperture can be beneficial for certain applications (such as, e.g., 1P in-vivo photostimulation, where a large working distance may be preferred.

Thus, for 1P applications (e.g., using Ru compounds) or when 2P-chromophores may not available (ChR-2), the microscope can be as simple as just a source 161 (e.g., blue laser or a regular visible-light fiber) and an exemplary SLM 165. In terms of optical components, for example, an excitation path can include an exemplary transmissive SLM 165 and a single-mode fiber 162. In certain examples, it can be preferred to maintain polarization for SLM 165. It can thus be possible to have no need to block 0-order since non-diffracted light spreading from the fiber can be off-focus (e.g., it can be considered as the analog of an off-center configuration but in an axial dimension). For 2P applications, a regular microscope objective can be used after the SLM 165 to obtain better focusing, for example.

For the sake of simplicity and making an exemplary microscope in accordance with the present disclosure be light weight and compact in size, photonic crystal band-gap fibers that can deliver ultrafast pulses can be used, which can help to provide a truly portable two-photon microscope. To make an exemplary microscope in accordance with the present disclosure be even more portable, the Chameleon can be replaced by something smaller, such as, e.g., a compact ultrafast fiber laser. For example, lasers from IMRA can be suitable for certain embodiments of the present disclosure as they can be considered to be very small, and are currently available in 780 nm and 800 nm models. Other factors that can be considered in selecting a compact ultrafast fiber laser can be, e.g., power, costs, etc.

Example of Emission Path (for imaging): Even for purely photostimulation applications, it can be useful to target areas of photostimulation (e.g., to locate cell bodies) first. While this type of targeting can be performed by a completely separate system (e.g., a compact LED-based wide field illuminator and a small camera), certain exemplary embodiments according to the present disclosure can use a SLM for this type of targeting in addition all of the other functionality the SLM can be used for, as discussed herein, for example. Speed may not be as important if the purpose may just be to acquire a calibration image since, generally, it can be done just once. For example, using a photo detector (e.g., a photomultiplier tube (PMT)), or a miniature avalanche photo diode), it is possible to scan the field using a SLM in accordance with certain exemplary embodiments of the present disclosure. While it can take longer to obtain a high-resolution 2D image than it would otherwise be possible, this example can be considered to be convenient to implement (e.g., software can be used to calculate phase patterns as opposed relying directly on complex math). A 2D detector can be used for faster imaging in certain exemplary embodiments of the present disclosure. A miniature camera coupled to microchannel plate image intensifier can also be used, for example.

Exemplary stages for implementing a 2D detector in accordance with certain exemplary embodiments of the present disclosure can include, e.g.:
1. obtaining transmissive SLM, build hand-held SLM-only 1P microscope, test for 1P stimulation application, without complex imaging;
2. testing imaging by SLM-only+point photodetector
3. adding objective lens—test 2P power delivery;
4. testing 2P imaging by photodetector;
5. adding 2D detector, develop fast imaging protocol:
6. introducing an ultrafast fiber to make 2P model portable; and
7. replacing Chameleon by a compact fiber laser.

Exemplary components that can be used in a 2D detector in accordance with certain exemplary embodiments of the present disclosure can include, e.g.:
1. a transmissive SLM;
2. a small breadboard to hold everything together;
3. holders/adaptors/lenses (e.g., from Thorlabs);
4. a detector avalanche photo diode/micro channel 2D detector (scientific-grade or from night goggles);
5. Fiber(s), e.g.,
    about 472 nm for 1P blue laser, and
    approximately 1-1.5 m of ultrafast fiber (e.g., from Crystal fibers) for 780 nm or 800 nm 2P;
6. a fiber alignment arrangement (e.g., from Thorlabs); and
7. an IMRA laser.

Additional exemplary benefits and/or advantages can include, e.g., the ability to build an add-on module to be able to upgrade 1P imaging setups to 1P uncaging (for example using the family of newly developed Rubi-caged compounds such as Rubi-glutmatae and Rubi-GABA) and/or photostimulation using genetically modified cells and 2P uncaging/space-selective imaging, providing a portable uncager that can be used for a wide variety of applications (e.g., Rubi-caged can be useful for, e.g., photodynamic therapy). Additional factors that may be considered can include, for example: temporal resolution for liquid-crystal SLM (can be considered to not be important for photostimulation and/or structural illumination imaging), power transmission (although power efficient lasers can offset power concerns), and use of a single computer to run fast imaging and calculate phase pattern.

Exemplary Multiplexed Laser Uncaging

It is possible to provide an optical method and system according to the exemplary embodiments of the present invention to facilitate neurons to fire reliably with a caged glutamate. The point spread function (PSF) of two-photon excitation can be too small to release enough free glutamate to effectively depolarize a neuron to action potential threshold. To make neurons fire action potentials reliably, it is possible to place several uncaging locations over the soma of the targeted cell for simultaneous photostimulation and calcium-imaging.

For example, FIGS. 2(*a*)-(*c*) show exemplary illustrations associated with exemplary two-photon photostimulation of MNI-glutamate with beam multiplexing.

In particular. FIG. 2(*a*) shows an illustration of exemplary results that are possible for uncaging with temporal beam multiplexing. In particular, image 210 provides an exemplary patched cell and the location of three sets of 12 uncaging targets 211 forming a circle, which can be sequentially stimulated (2.5 ms per point). Dots 212 provided in FIG. 2(*b*) represent imaging targets. The scale can be about 10 μm.

FIG. 2(b) shows a graph of exemplary results for a spatial resolution of uncaging. For example, top traces 221 represent exemplary electrophysiological recordings of the neuron during uncaging at positions shown in FIG. 2(a). As shown in this exemplary drawing, uncaging in position 1 can trigger a burst of action potentials. The holding potential can be, e.g., about −65 mV. The bottom trace 222 represents an exemplary laser pulse. As shown in exemplary positions 2 and 3 of FIG. 2(b), the action potential threshold may not always be reached.

Further, FIGS. 2(c)-(e) show exemplary results for uncaging with diffractive optical element (DOE) spatial beam multiplexing. In particular, FIG. 2(c) shows an illustration of exemplary results that can be obtained with an exemplary neuron stimulated by a linear DOE pattern. Dots 231 represent uncaging targets and dot 232 represents the imaging target. The scale can be about 10 μm.

FIG. 2(d) shows a diagram of an example in which a DOE 240 splits a laser beam 241 spatially, creating a pattern 242 that can illuminating five spots simultaneously, thus shortening the uncaging time required to reach action potential threshold. For example, DOE 240 and sequential multiplexing can be combined, as shown by the example of FIG. 2(c), so a total of twenty spots 242 are illuminated, five at a time. FIG. 2(e) shows graphs of an example of DOE photostimulation, illustrating the quicker uncaging time, as shown by line 251, to generate spiking, as illustrated by spikes 252. Exemplary panels associated with the example of FIG. 2(e) can be similar to those associated with FIG. 2(b).

FIG. 2(f) shows a graph of exemplary results of a depth resolution of beam multiplexing two-photon uncaging. For example, curve 254 represents the number of action potentials that can be induced by uncaging pulses at different depths, normalized to the maximum number of action potentials that can be induced. Curve 255 represents two-photon fluorescence of each focal plane, normalized to the maximum fluorescence of the corresponding soma. As shown, there can be a close correspondence between these curves 254, 255. Thus, the axial resolution of two-photon photostimulation can closely follow 3D sectioning properties of two-photon fluorescence imaging. Exemplary uncaging can be performed with, e.g., an exemplary 4×3 ms, 5-beamlet DOE protocol with a 20×0.5 NA objective. Error bars 256 can be standard error of the mean (SEM).

Turning back to the exemplary illustration of FIG. 2(a), exemplary "complex" stimulation targets (see S. Shoham, supra) 211 can have a diameter similar to that of the exemplary stimulated neuron 210 and the spatial resolution of their uncaging response can also be comparable to the average diameter of a cell body. For simultaneous imaging and uncaging, it is possible to position a single imaging target in the center of the stimulation targets, as shown by exemplary imaging target 212 being in a center of exemplary stimulation targets 211.

To improve the temporal resolution of uncaging (e.g., to reduce the time necessary for reaching the action potential firing threshold) and more effectively utilize the available laser power, it is possible to optically split the laser beam 241 into several closely spaced beamlets 243 for simultaneous uncaging of several different spatial locations around cell somata. As shown in the exemplary graph of FIG. 2(d), this can be performed by using exemplary DOE (see Froner E Sacconi L, Antolini R, Taghizadeh M R, Choudhury A, Pavone F S., Opt Lett. 28 (20), 1918 (2003)) 240, which can be, e.g., an efficient single-element beam-splitter suitable for a non-linear microscopy. Such exemplary DOE 240 can produce an exemplary symmetrical linear 5-spot pattern 242 in the far field (e.g., $1^{st}$ diffraction order). The exemplary DOE 240 can be placed on an optical table at the plane optically conjugated to the plane of scanning mirrors, as is described herein below with reference to FIGS. 7(a)-7(c), for example. The magnification of the intermediate telescope can be adjusted according to the objective lens of the microscope in order to produce a pattern of, e.g., 5 beamlets 243 covering approximately the size of a neuronal soma 244, for example.

The use of exemplary DOE 240 in combination with complex targets 231 can facilitate the use of shorter uncaging pulses. Most neurons can be stimulated with 10-13 ms uncaging pulses to produce a short burst of about 3-7 action potentials, and it is possible to induce individual action potentials with uncaging pulses as short as 5 ms, as shown by exemplary pulse 253 as shown in FIG. 2(e). Exemplary DOE 240 likely not only increase the efficiency of uncaging, but also improve the signal-to-noise ratio of point measurements for vector-mode imaging, because the PMT can sample, e.g., five spatially different somatic locations 210 illuminated simultaneously by separate beamlets 243.

It is possible to measure the axial resolution of these exemplary beam-multiplexed uncaging methods by monitoring both the two-photon fluorescence and the action potential responses of a neuron, while systematically changing the focal plane of the uncaging laser. For example, an axial displacement of about 30 μm can effectively prevent the response of the neuron to the uncaging pulse, as shown by an exemplary trace 254 of the exemplary graph shown in FIG. 2(f). The two-photon fluorescence profile can also be dependent on the focal plane, represented by exemplary trace 255 shown in FIG. 2(f). These exemplary results demonstrate the optical sectioning capabilities of exemplary uncaging methods in accordance with the present disclosure, an inherent property of two-photon excitation, for example.

Two-Photon Imaging with Diffractive Optical Elements

FIGS. 2(g) and (h) show schematic representations of exemplary implementations of a diffractive optical element (DOE) to enhance two-photon imaging in a horizontal DOE mode according to certain exemplary embodiments of the present disclosure.

For example, FIG. 2(g) shows that traditional raster scan imaging can require time for a mirror system to scan an excitation beam across a field of view and can have a certain ceiling as to a quantity of excitation that can be possible before photodamage can occur. FIG. 2(h) illustrates that using a diffractive optical element (DOE) 260, it can be possible to split a beam 261 into an number of beamlets 262. Using beamlets 262 spread horizontally, it can be possible to image in a way that can allow for summation of the signals excited by a sample at each pixel to yield a greater signal and increased signal to noise ratio. An exemplary embodiment in accordance with the present disclosure of a horizontal DOE mode or "excitation boost" can be used for, e.g., line scans or full-field frame scans, which could be at the expense of some spatial resolution, for example.

FIGS. 2(i) and 2(j) illustrate schematic representations for utilizing a diffractive optical element (DOE) to enhance two-photon imaging in a vertical DOE mode according to certain exemplary embodiments of the present disclosure.

An exemplary embodiment in accordance with the present disclosure of a Vertical DOE mode or "speed boost" can achieve greater speed of scanning than traditional raster scanning. By spacing DOE-created beamlets widely over the vertical aspect of the field of view and scanning each beamlet simultaneously horizontally across a narrow strip of the field of view, it can be possible to excite the full field of view in 1/(number of beamlets) in about the same amount of time required for a single beam. For example, as indicated by arrows 263 and 264 to the left of each representation of a field of view 265 and 266, respectively, in the standard raster scan mode, a single beam must make horizontal line scans along the entire height of the field (e.g., arrow 263). In contrast, in an exemplary speed boost mode, each beamlet can simultaneously scan a fraction of the vertical aspect of the field (e.g., arrows 264). A camera or other similar wide-field light (or electromagnetic) collection device (such as, e.g., a photodiode array or multianode photomultiplier tube) with a resolution equal to at least the number of beamlets can be used with this exemplary method since more than one area can be excited simultaneously.

FIGS. 2(k)-2(o) show exemplary results for line scanning with a horizontal diffractive optical element (DOE) mode according to certain exemplary embodiments of the present disclosure.

FIG. 2(k) illustrates exemplary full-frame raster scan images 271 and 272 of a neuron 270 filled with Fura 2 pentapotassium salt acquired using traditional single beam excitation (image 271) and an exemplary five beamlet excitation (image 272). As shown, with multiple beamlets, there can be slight blurring of the image of the neuron, however the narrow spacing can minimize this blurring to the extent that the cell is clearly distinguishable. These images can be used to select a level for line scanning (e.g., the white horizontal line 273 and 274 in each image).

FIG. 2(f) shows exemplary results of line scans acquired at 80 scans per second using single beam (image 275) and multibeam (image 276) excitation. As shown, time can be represented in the horizontal axis, with each vertical column representing one scan. An exemplary limited spatial extent of the line scan which includes the cell soma is shown for display purposes. The neuron was patch clamped and driven to fire action potentials during the optical recording.

FIG. 2(m) shows exemplary graphs of intensity versus time profiles of the exemplary linescans shown in FIG. 2(l). As shown, the raw brightness intensity can scale about the same in each of the graphs in varying brightness units. Calcium transients can be visible corresponding to times of action potential firing indicated in the whole cell patch clamp current clamp trace, as shown in FIG. 2(o), for example. In this experiment, the cell was induced to fire an increasing number of action potentials, starting with 1 and ending with 5. Calcium transients grew monotonically in correspondence to the number of action potentials in both imaging regimes but can be seen more clearly in the five beamlet exemplary embodiment. The results shown in FIG. 2(n) are from the same data as from the experiment of FIG. 2(m), but re-plotted such that the percent change from baseline (DF/F) is equivalent for both traces 277 and 278. As can be seen, the calcium transients induced by a given number of spikes are about the same amplitude in both conditions, although noise is decreased in the five beamlet experiment, showing that there can be a greater signal to noise ratio with DOE imaging. In this experiment, the signal to noise ratio was improved by about 1.91±0.24 fold (n=5 signals) in the exemplary excitation boost DOE imaging results shown versus the single beam imaging in this experiment.

FIGS. 2(p) and (q) show exemplary results for an enhanced frame scan with a diffractive optical element (DOE) according to certain exemplary embodiments of the present disclosure.

FIG. 2(p) shows full-frame raster scan images of a population of neurons bulk loaded with Fura 2-AM calcium indicator dye acquired using traditional single beam excitation (image 279) and five beamlet excitation (image 280). The experiment showed that horizontal DOE mode can slightly decrease spatial resolution but not to an extent that resolution of single cells generally would be considered to be problematic. Images 279 and 280 are the product of average pixel-wise projection of a movie. FIG. 2(q) shows intensity versus time profiles of time-lapse movies of the shown field of view for the cell 281 indicated by arrow 282 in FIG. 2(p). The scales were the same in graphs 283 and 284, with the vertical axis in brightness units and the horizontal axis in seconds. The neuron of interest 281 was patch clamped and driven to fire sets of three action potentials during the optical recording. Calcium transients are visible corresponding to the times of the action potential firing (indicated by arrows 285 and vertical lines 286). The signal to noise ratio was improved in this experiment by an average of 1.95±0.72 fold in the excitation boost multibeam excitation boost frame scan mode relative to single beam imaging.

FIGS. 2(r)-2(t) show exemplary results for scanning with a vertical diffractive optical element (DOE) mode according to certain exemplary embodiments of the present disclosure.

FIG. 2(r) shows results from a progressive full-field scanning of a paper sample using many beams spread vertically over the field of view and captured with a CCD camera. Image 287a is a "line scan" which creates a number of lines of excitation equal to the number of beamlets. Moving right from image 287a to images 287b-d, it is possible to see the results of a demonstration of scanning that was performed by this system. The beamlets were allowed to scan for a longer time with each image 287a-d, eventually covering the entire field of view with each frame capture by the camera.

FIG. 2(s) shows results from full-frame scanning of a patch clamped neuron using a traditional single beam with PMT detection. The experimental movie was acquired at one frame per second. The graphs show the intensity versus time profile and patch clamp recording for cell 288 indicated by arrow 288a, which was driven to bursts of an increasing number of action potentials (e.g., the number of action potentials per burst is indicated below the trace 289, and the timing is indicated in the imaging trace with dotted vertical lines 289a). The vertical axis of brightness trace is in brightness units, and the horizontal axis in seconds.

FIG. 2(t) shows exemplary results of vertical DOE scanning of a population of neurons using 11 beamlet excitation and imaging with a CCD camera. The experimental movie was collected at 10 frames per second. As shown by spike 290a in trace 290, the calcium transients corresponding to times of bursts of two or three action potentials can be more easily visible in the calcium indicator tracing produced by DOE-based imaging than with single beam raster scan, for example. Furthermore, while calcium transients produced by 9 to 11 action potentials per burst can be easily distinguishable in both cases (e.g., by spike 290b), they were found to have about a 2.15-fold greater signal-to-noise ratio in this exemplary experiment of speed boost imaging.

FIGS. 2(u) and (v) show exemplary results for imaging of sub-micron beads using a diffractive optical element (DOE) according to certain exemplary embodiments of the present disclosure. In this experiment, 0.5 μm fluorescent beads were imaged using a single beam 292 (image 291, FIG. 2(u)) and a five-beamlet 294 DOE in frame scan mode (image 293, FIG. 2(v)). The beads were imaged at about 800 nm with about 30 mW of total power on the sample. About 5-7 mW per beam was used with a 20×0.95NA objective with a 10× zoom factor in imaging software. In this experiment, there was 0.2 μm per pixel with interbeamlet distance of 1.5 μm and a total five-beam spread of 7.5 μm.

Figure 2X:
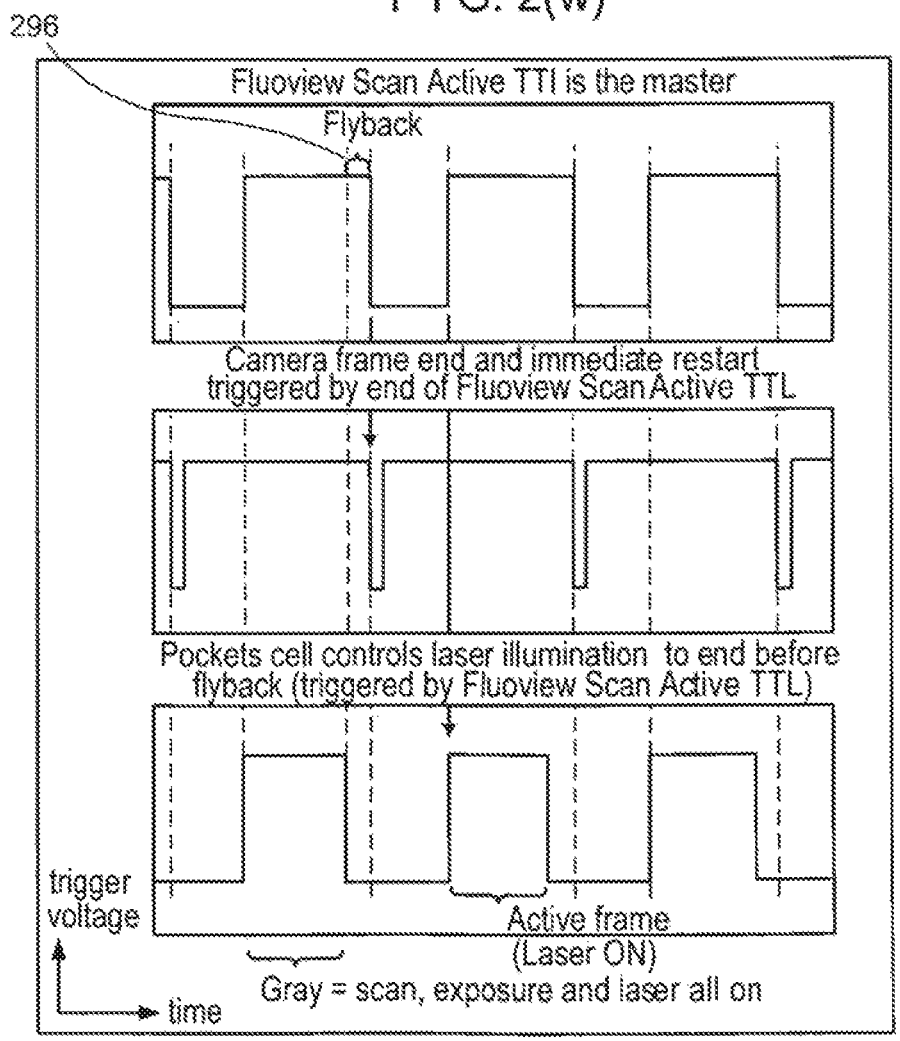

FIGS. 2(w) and 2(x) show exemplary results for scanning in speed boost vertical diffractive optical element (DOE) scanning mode according to certain exemplary embodiments of the present disclosure and speed boost mode equipment synchronization.

In this experiment, to address the timing and coordination of scanning, camera exposure and laser intensity during speedboost mode vertical DOE scanning mode, the CCD-camera exposure and acquisition with galvanometer mirror-based scan times were synchronized. As demonstrated in FIG. 2(w), when simply exposing the CCD chip for as long as the exemplary scanning software sent outputs indicating active scanning, an artifact of diagonal lines 296 (pointed out by diagonal arrows 296a) appeared. When the duration of time of full strength laser pulse was specifically controlled and the laser power was turned down to 0, it was possible to eliminate this artifact, as can be seen in image 295b.

This effect can be due to a "flyback" (see, e.g., flyback 296 in FIG. 2(x)) or movement of the galvanometer mirrors from their final position to their original position in preparation for the next scan. In this experiment, it was found that allowing the galvanometer scanning system to run independently and forcing the camera frame timing and laser intensity to follow the timing of that system worked better than the inverse, given the respective response times of the specific imaging and scanning systems that were used in this experiment. The voltage pulse controlling laser power was set via a Pockels cell to last a particular number of milliseconds depending on the details of the scan. Further, the exemplary camera exposure control was stopped by the end of the frame scan output and was immediately re-begun to not miss the beginning of the following scan.

For additional examples and experiments of two-photon imaging with diffractive optical elements, see Watson, Brendon O., Nikolenko, Volodymyr, and Yuste, Rafael, *Two-photon imaging with diffractive optical elements*, Frontiers in Neural Circuits, 3, 1 (2009).

Exemplary Two-Photon Mapping of Synaptic Inputs with Single Cell Resolution

FIGS. 3(a)-(f) show illustrations of the exemplary results of the present disclosure for two-photon input mapping with single cell resolution according to an exemplary embodiment of the present disclosure.

In particular, FIG. 3(a) shows an illustration of an exemplary input map for a layer 5 pyramidal neuron and super-imposed morphological reconstruction of its dendritic tree 311. In this example, as shown in top panel 310 of FIG. 3(a), areas 312 can outline stimulated neurons. Other areas can be outlines of all "true positive" cells 313, which can be coded according to peak EPSP amplitude, for example. The scale can be about 100 μm. Dotted outline 314 represents an exemplary patched pipette. The lower panel 315 shows exemplary voltage recordings 316 (upper traces) from a patched cell during uncaging, with exemplary corresponding laser pulses 317 (lower traces) in locations labeled by arrows 318. The holding potential can be, e.g., about −65 mV.

FIG. 3(b) shows illustrations of an exemplary map 320 of false positive signals 321 for the same neuron. As shown in this example, the morphology of the exemplary dendritic tree 311 can be tracked. Lower panel 325 shows recordings of false positive signals 326 and 327 during uncaging in corresponding locations labeled as arrows 328 and 329, respectively. As shown in this exemplary illustration, the difference in kinetics and amplitude between true and false positive signals can be provided.

FIG. 3(c) shows an illustration of exemplary results providing that true-positive signals can be monosynaptic connections. An exemplary post-synaptic neuron 331, indicated by arrow 332, can be patched and all neurons labeled by dots 333 can be sequentially stimulated. As shown by this example, the neuron labeled by dot 334 can give a true-positive signal and be subsequently patch-clamped. As shown, there can be a significant distance between both neurons 331 and 334. The scale can be about 50 μm.

FIG. 3(d) shows graphs of exemplary dual recordings from the two neurons 331, 334, which can reveal a monosynaptic connection. As shown in FIG. 3(d), action potentials can be induced by current injection in the putative presynaptic neuron 334, which can be represented by trace 341, and can cause time-locked EPSPs in the postsynaptic cell 331, as represented by trace 342. As shown in an exploded view 343 of FIG. 3(d), correspondence between onset of action potentials and EPSPs can be provided. Both neurons can be held at, e.g., −63 mV.

FIGS. 3(e) and (f) show graphs of exemplary embodiments according to the present disclosure of monosynaptically connected true-positive cells of two further examples.

For example, mapping of synaptic inputs to different neurons can be performed by performing electrophysiological recordings in current clamp from selected neurons and photostimulating most, or all, labeled neurons in the surrounding area in slices from mouse somatosensory and visual cortex (e.g., FIG. 3(a), with n=169 maps), and as also described herein. It is possible to use AM-dye loading to label cortical neurons, in contrast to other methods for identification of neurons/layers/cortical areas that may have been used in the past for one-photon uncaging mapping, such as, e.g., infrared-guided microscopy. (See H. U. Dodt, supra). In a typical exemplary embodiment, with a 10× objective and 1.5× scanning zoom, an exemplary procedure can detect, e.g., about 700-1,000 loaded cells in a single focal plane, as described in more detail herein below with reference to FIG. 8. These parameters can be convenient, e.g., for visualizing all cortical layers in a single field of view. Although it can be possible to stimulate every single cell, to complete the protocol in a reasonable time, the number of neurons stimulated can be restricted to, e.g., about 500, targeting neurons in any particular or a pseudo-random fashion. As a control, patched cells can be stimulated by uncaging at the end of the photostimulation protocol, for example.

In the exemplary mapping procedures and results described herein, two distinct classes of postsynaptic responses can be encountered, e.g., time-locked to the uncaging pulses, 317, 327, as shown by the examples of FIGS. 3(a), (b), respectively (see also, e.g., Table 361 in FIG. 3(g)). These exemplary events can closely resemble the two types of events described during one-photon glutamate uncaging (see R. Kotter, supra): compound monosynaptic EPSPs can be induced by short bursts of action potentials in presynaptic photostimulated cells (e.g., "true positives" 313, as shown the exemplary illustration of FIG. 3(a)), and larger, slower depolarizations with shorter latencies, which may be caused by direct uncaging onto distal dendrites of the patch-clamped cells (e.g., "false positives" 321, as shown in FIG. 3(b)). Although dendrites may not be visible with the exemplary loading conditions, and only cell bodies may be targeted by the stimulation protocol, it is still possible that dendrites can cross near the stimulated area, and thus become stimulated directly. It is possible to distinguish between true and false positives based on their different onset kinetics and latencies to the uncaging pulse, and there can be statistically significant differences across these measured variables (see, e.g., Table 361). In addition, overlaying the morphological reconstruction of dendrites of patch-clamped neurons with input maps can show that the false-positive signals can trace the dendritic tree 311 of the postsynaptic cell, as shown in FIG. 3(b), whereas the true-positive signals 313 likely may not, as shown in FIG. 3(a).

Sorting of true and false positive responses can be confirmed by applying the sodium channel blocker TTX (1 μM) to block action potential generation in the slice and thus prevent all evoked synaptic release. By performing mapping examples in TTX, it is thus possible to obtain the maps of false positive signals and compare them with results of manual sorting of false positives in the absence of TTX. These exemplary control examples can provide that the probability to incorrectly count false positive signals as true positives will likely be small (e.g., 0.45% on average, n=17 maps). In contrast, using manual sorting criteria, it can be stricter than the TTX definition of a false positive. For example, whereas 99.3% of the TTX false positives can also be identified as such manually, only 84% of manually labeled false positives may later be confirmed by mapping in TTX.

Further, using dual whole-cell recordings, it is possible to confirm that neurons that generate true-positive signals after being stimulated by uncaging are indeed monosynaptically connected to the patch-clamped postsynaptic neuron (see, e.g., FIG. 3(c)), because the EPSPs can be generated after action potentials are triggered in the putative presynaptic neuron, which can have short synaptic delays (e.g., 0.79±0.04 ms; peak EPSP amplitudes: 1.68±0.11 mV; 3/3 pair recordings).

Exemplary Functional Maps of Synaptic Properties

Exemplary embodiments of method and device according to the present disclosure can facilitate an identification of not only putative presynaptic neurons, but also a measurement of their synaptic properties, such as amplitude or onset/offtet kinetics of unitary synaptic EPSPs, and can generate exemplary maps of their distribution according to the position of the somata of the pre- and post-synaptic neurons (for exemplary amplitude maps, see, e.g., FIGS. 3(a) and 9(a)-9(d)). Because uncaging generated several short bursts of action potentials in the stimulated cells, it can also be possible to, e.g., measure, for each input cell, more complex synaptic properties such as rate of facilitation/depression, total amplitude of compound EPSP, accommodation after several photostimulation pulses, etc.

Exemplary Input Maps in Three Dimensions

To demonstrate the optical sectioning capabilities of the uncaging and the accuracy of exemplary input maps, exemplary mapping in two different focal planes separated by 45 μm can be performed, as illustrated. e.g., in the illustrations shown in FIGS. 4(a)-4(f), which illustrates exemplary mapping inputs in three dimensions.

In particular, FIG. 4(a) shows an illustration of an exemplary map 410 of all mag-Indo-1AM loaded cells 411 (n=635) that can be detected at a superficial focal plane of the exemplary slice 412 (labeled 0 μm). 300 positions out of these 635 can be stimulated to test for potential connectivity. An exemplary patch pipette 413 is shown in outline in this figure. The exemplary scale can be about 100 μm. FIG. 4(b) shows an exemplary map 420 of loaded cells 421 (n=546) that can be 45 μm below the exemplary map shown in FIG. 4(a). An exemplary difference between cell positions at these two exemplary focal planes is shown by the overlay of the exemplary map 430 of FIG. 4(c). FIG. 4(d) shows an exemplary map 440 in which positions 441 (n=20) can produce true-positive responses in the patched cell while stimulated at focal plane of the exemplary map 410 of FIG. 4(a). FIG. 4(e) shows an illustration of an exemplary map 450. As shown in FIG. 4(e), exemplary positions 451 (n=17) can generate true-positive responses at the focal plane of the exemplary map 420 of FIG. 4(b). The 300 coordinates that can be tested can be identical to those used in Figure(d). FIG. 4(f) illustrates an exemplary map 460 for utilizing overlay of inputs maps. As shown in the example of FIG. 4(c), an overlap at only two positions 461 is possible, demonstrating the ability of selectively mapping inputs at two adjacent focal planes.

Such exemplary separation can be performed in order to facilitate that neurons in neighboring focal planes are not stimulated. As shown, negligible overlap between connectivity maps in two different focal planes can be obtained. For example, only 2 out of 300 target coordinates can be selected at one focal plane to yield true positive responses in both focal planes. This is possible because of the optical sectioning ability of this exemplary two-photon uncaging protocol in accordance with the present disclosure. Thus, independent inputs maps can be built with a depth resolution comparable to the average size of a neuronal cell body, for example.

Experimental Input Maps from Adjacent Cells

FIGS. 4(g)-(l) provide exemplary illustrations of simultaneously acquired input maps 471-476 from, e.g., four neurons A 476, B 477, C 478 and D 479. As shown, exemplary mapping can be performed by simultaneous recordings from several neurons to improve the efficiency of some of the exemplary protocols or procedures in accordance with the present disclosure. As indicated in this example, such improvement in efficiency can be effectuated because several input maps can be obtained during a single run of this exemplary protocol.

For example, according to one experiment, 26 single cell maps, 16 simultaneous maps of pairs of neurons, 25 of triplets and 9 of quadruplets can be recorded, for a total of 169 maps. An interesting result can be that even very closely positioned neurons of the same class (e.g., large layer 5 pyramids, for example) can have very different input maps, as shown the exemplary illustration provided in FIGS. 4(g)-4(l), indicating that functional independent networks of cortical neurons can be superimposed in the same cortical territories (see Y. Yoshimura, J. L. Dantzker, and E. M. Callaway. Nature 433 (7028), 868 (2005)), for example.

Exemplary Repeatability of Input Maps

It is also possible to verify the stability of exemplary input maps and the repeatability of an exemplary stimulating protocol and analysis in accordance with the present disclosure by using, e.g., a shortened version thereof, with, e.g., about 5-8 minute intervals between each input map being obtained.

FIGS. 5(a)-(h) are exemplary images for reproducibility of exemplary input maps, in which n=7 postsynaptic neurons resulting from an implementation of an exemplary embodiment of the present disclosure.

For example, FIGS. 5(a)-(g) show illustrations of consecutive exemplary input maps 501-507 from the same neuron 500 (marked by tip of exemplary pipette outline 509), that can be obtained sequentially over approximately one hour. Lighter areas outline all stimulated cells 510 and darker areas those cells 511 generating true positives. Lower panels 512-518 of FIGS. 5(a)-5(g) show exemplary EPSPs, indicated by upper traces 519-525, respectively. Exemplary EPSPs can be generated by uncaging (lower traces 526-532;

laser pulses 533) the black cell 534 identified by the arrow 535 with an exemplary holding potential of about −65 mV. FIG. 5(h) shows an exemplary image illustrating exemplary locations that can produce a true-positive response in every exemplary map. The scale can be about 100 μm, for example.

These exemplary maps 501-508 of FIGS. 5(a)-5(h) demonstrate, e.g., that the repeatability and shapes of EPSPs from selected cells can be similar from trial to trial. For example, 77.1±12% of all true positive cells 511 can score as true positive in every map, (mean±SD; n=7 cells, >7 maps each). This example demonstrates that an exemplary protocol in accordance with the present disclosure can produce reliable maps. In addition, this example demonstrates that such exemplary uncaging method and/or procedure may not compromise the health of stimulated neurons.

Further, a small degree of variability in input maps, as shown by a comparison of exemplary maps 501-507, can be obtained. This small degree of variability can be due, e.g., to an inconsistency in number of action potentials generated by the uncaging pulses (see, e.g., illustrations of FIGS. 2(b) and 6(a)). This small degree of variability can also reflect spontaneous fluctuation of synaptic weights or synaptic rewiring. (See J V. Le Be and H. Markram, Proc Natl Acad Sci USA. 103, 13214 (2006)). Thus, an exemplary method and device according to certain exemplary embodiments of the present disclosure can be used, e.g., to determine a cortical plasticity in long-term examples exemplary embodiments.

Exemplary Simultaneous Two-Photon Stimulation and Imaging

Further, a combination of the exemplary embodiment of the photostimulation method and device with calcium imaging of circuits can be implemented. (See Rafael Yuste and Lawrence C. Katz, Neuron 6, 333 (1991)). As shown in FIG. 1(c) and described herein above, for example, single spikes can be detected with vector-mode calcium imaging when action potentials are induced by injection of a current pulse to an exemplary patch-clamped neuron. A similar sensitivity can be determined when action potentials are triggered by two-photon uncaging of MNI-glutamate. By comparing the amplitude of calcium transients exhibited by photostimulated cells loaded with Indo-1AM, but not patchedit, it is possible to estimate that the uncaging event induced a similar number of action potentials in neurons that were not patched.

For example, when uncaging in some neurons, in addition to calcium transients similar to those generated by action potentials in the photostimulated cells, similar optical signals in cells can be detected that were not photostimulated.

FIGS. 6(a)-(c) show an exemplary illustration of certain exemplary results for all-optical stimulation and imaging of network activity.

In particular, FIG. 6(a) shows illustrations and graphs an exemplary embodiment of an optical detection of uncaging responses in accordance with the present disclosure. The top panel 601 of FIG. 6(a) shows exemplary darker neurons 602 can be photostimulated sequentially while being simultaneously imaged in vector-mode. The lower panels 603 show electrophysiological recordings 604 (upper trace of FIG. 6(a)) of exemplary neuron 1 605 and fluorescence calcium measurements 608-610 from neuron 1 605, neuron 2 606 and neuron 3 607 (middle traces, ΔF/F) during uncaging on their cell bodies (lower trace 611 shows laser pulses 612). Inset 613 shows how uncaging can trigger action potentials in neuron 1 605 (loaded with Indo-1-K 50 μM through a patch-pipette), producing easily detectable calcium signals.

Uncaging on neurons 2 606 and 3 607 (not patched and loaded by Indo-1AM) can generate calcium signals of similar amplitude to those in neuron 1 605, which can be due to action potential activity, for example. Imaging and uncaging can be performed with exemplary complex DOE targets, e.g., imaging: 5 ms/neuron; uncaging: 4×2.5 msec/neuron) The scale can be about 50 μm, for example.

FIG. 6(b) shows illustrations and graphs of an exemplary embodiment of a sequential stimulation with a simultaneous imaging. As shown in the top panel 621, e.g., 50 exemplary neurons 622 (indicated by their darker shade), can be continually imaged while being sequentially photostimulated. Middle panel 623 displays the exemplary protocol of the exemplary process, in which every neuron can be imaged (horizontal lines 624) while neurons marked with vertical bars 625 are being stimulated. Shown in lower panels 626 is an example of activation of one neuron by the stimulation of another neuron. Upper traces 627 are exemplary fluorescence measurements and lower traces 628 represent exemplary laser pulses. As shown in this example, uncaging pulses 629 on neuron 1 605 can generate calcium signals 630, which can be due to action potentials, in neuron 1 605; whereas, uncaging over neuron 2 606 can generate calcium signals, not only in exemplary neuron 606 (e.g., spikes 632), but also in exemplary neuron 1 606 (e.g., spikes 631). According to this example, exemplary joint loading of mag-Indo-1AM and Indo-1 AM can be used. The scale can be about 50 μm, for example.

FIG. 6(c) shows illustrations and graphs of an exemplary embodiment of simultaneous stimulation and imaging. Top panel 641 reflects a similar example as the example shown in FIG. 6(b). However, in FIG. 6(c), different sets of 5 neurons 642 (indicated by arrows 643) can be stimulated simultaneously, while all 50 neurons 622 are being imaged, for example. Middle panel 642 shows how the exemplary protocol of this example can display the sequential activation of exemplary sets of five neurons 642, as indicated by vertical lines 645, during the imaging of all other ones, as indicated by the horizontal lines 646 without respective intersection with vertical lines 645. The bottom panel 647 represents an exemplary analysis of this example. For each exemplary cell displayed on the y-axis, darker tick marks 648 represent exemplary detected calcium transients and dots 649 represent exemplary stimulated neurons. As shown, the synchronous stimulation can reliably trigger calcium transients in the exemplary stimulated cells, but, interestingly, can also generate network activity (e.g., vertical arrays of black lines 650), in some cases leading to a synchronized activation of most of the imaged cells, indicated by star 651. The exemplary maps of this example can be reprinted in higher resolution and used as shown and described above with reference to FIGS. 5(a)-(h). According to this example, exemplary joint loading of mag-Indo-1AM and Indo-1AM in accordance with the present disclosure can be used. The scale can be about 100 μm, for example.

The calcium transients can be time-locked to the uncaging pulses 629 shown in FIG. 6(b). For example, the neurons that exhibit calcium transients can be located far from the stimulated cells, implying that the action potentials that trigger the optical signals may not be a consequence of unspecific direct stimulation of the dendrites of the postsynaptic neurons. Thus, such functional signals in distant cells can be attributed to action potentials induced by strong excitatory connections from photostimulated neurons. Indeed, strongly facilitating monosynaptic connections that can fire a postsynaptic cell, for example, between pyramidal excitatory cells and low-threshold spiking intemrneurons have been shown. (See Y. Kawaguchi, J Neurosci 15 (4), 2638 (1995); J. Kozloski, F. Hamzei-Sichani, and R. Yuste, Science 293 (5531), 868 (2001); Y. Wang, M. Toledo-Rodriguez, A. Gupta et al., J Physiol 561 (Pt 1), 65 (2004)).

Further, it is possible to utilize the exemplary embodiments of the present disclosure to the quasi-simultaneous stimulation of several cells (e.g., five neurons, 60-90 ms total uncaging time), while simultaneously monitoring network response (see, e.g., FIG. 6(c) top panel and FIG. 6(c) middle panel). In further examples, it is possible to trigger a simultaneous calcium transient in many neurons, time-locked to the uncaging pulse, by the stimulation of certain combinations of neurons (see FIG. 6(c) bottom panel). These global activations can be similar to those that may be observed under some types of epileptiform events. (See T. Badea, J. Goldberg, B. Q. Mao et al., J. Neurobiol. 48, 215 (2001); A. J. Trevelyan, D. Sussillo, B. O. Watson et al., The Journal of neuroscience: the official journal of the Society for Neuroscience 26 (48), 12447 (2006)). Accordingly, it is possible for paroxysmal depolarization shifts to be observed by simultaneous electrophysiological recordings. Similar epileptiform events can occur spontaneously in exemplary slices perfused with MNI-glutamate since such events can be time-locked to the photostimulation of a specific set of exemplary neurons. Accordingly, the stimulation of very few neurons can be sufficient to trigger an epileptiform event in a slice in some exemplary embodiments according to the present disclosure.

Further Discussion of the Exemplary Embodiments

As described herein, the two-photon photostimulation of neuronal circuits can be provided in combination with calcium imaging, in accordance with certain exemplary embodiments of the present disclosure. By taking advantage of the exquisite spatial resolution of two-photon uncaging and using beam multiplexing optics, such exemplary technique and device can overcome certain previous problems of one-photon photostimulation, e.g., the lack of single-cell resolution in the mapping of synaptic inputs. By systematically uncaging glutamate on the somata of hundreds of neurons while recording the intracellular activity of a cell of interest, it is possible to obtain single-cell resolution maps of excitatory connections in the slice.

For example, the neurons can be detected automatically and using an exemplary mapping procedure that is under computer control, and thus it is possible to sample relatively quickly (e.g., approximately 30 minutes) a large number of neurons (e.g., up to 1,000) and test whether or not they are connected to the recorded cell. Indeed, using dual whole-cell recordings, putative input cells can be monosynaptically connected to the recorded neuron. It is possible to interpret the map of true positive inputs as the map of neurons presynaptic to the recorded cell. In addition, such exemplary maps can be obtained in three dimensions, so one could in principle sample all the cells in the tissue and test whether they are presynaptic to any given cell, getting closer to Crick's dream of revealing all the connections onto a given cell. (See FH. Crick, supra)[2].

Figures 4G, 4H, 4I, 4J, 4K, 4L:
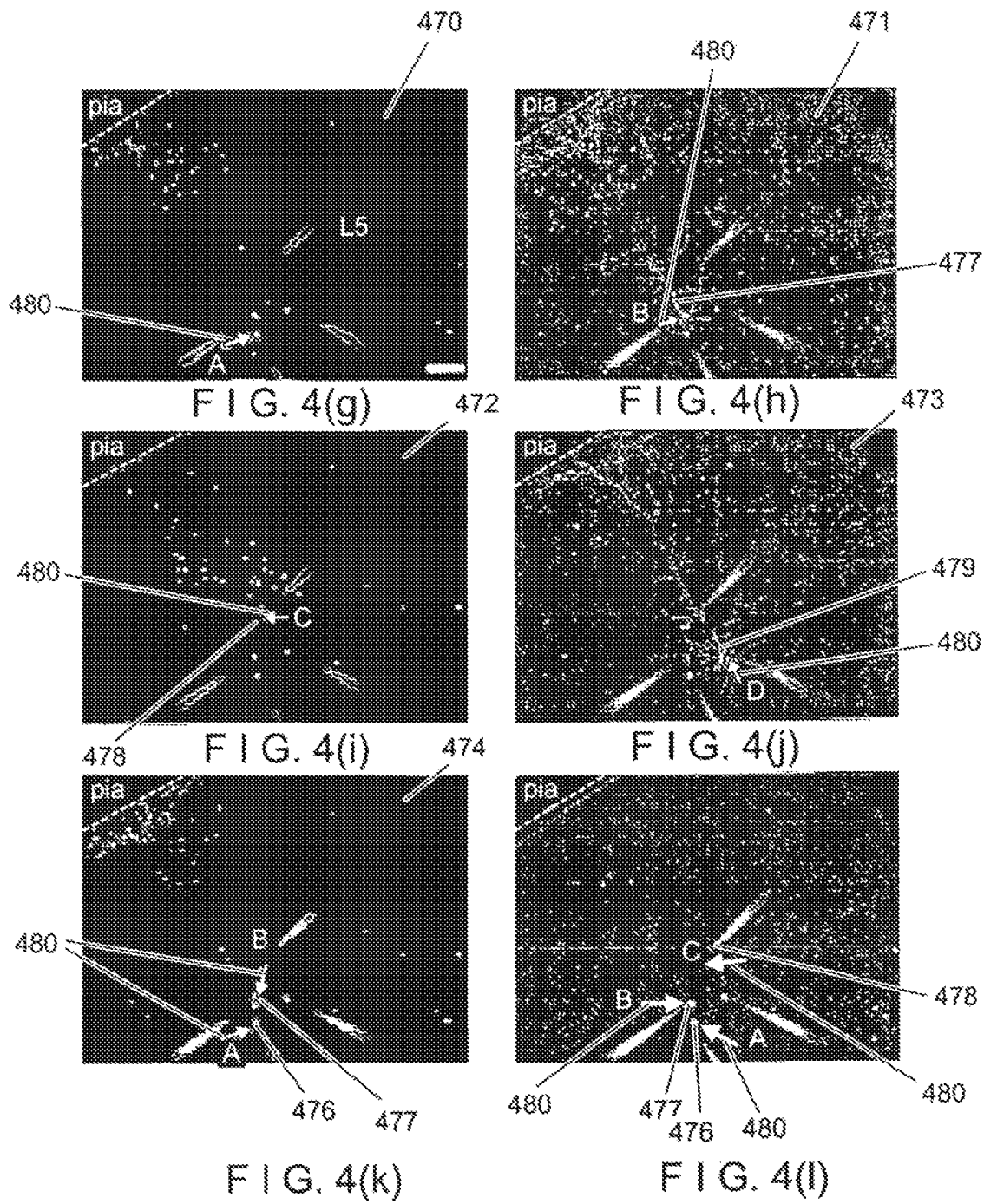

In addition to its use for anatomical mapping, certain exemplary embodiments of method, system, arrangement, computer-accessible medium and device according to the present disclosure can be used to map functional synaptic properties. The number of synaptic contacts can be estimated or determined from the amplitude of the synaptic response, and other properties such as the failures or synaptic dynamics may be obtained by further analysis. In addition, similar exemplary maps to the ones presented herein can be obtained in voltage clamp mode, thus enabling a biophysical analysis of synaptic connections from different presynaptic neurons, for example. Furthermore, since several neurons can be patched at the same time, simultaneous functional maps can be obtained and compared (see, e.g., FIG. 4(g)-(l)). In addition, because these input maps can be obtained quickly and reproducibly, as shown in FIG. 4 and described in the corresponding description herein, this exemplary technique and device can be used, e.g., to monitor changes in synaptic connectivity. (See JV. Le Be, supra). Further, it is possible to detect inhibitory responses, and thus, exemplary embodiments of a technique and device in accordance with the present disclosure can be extended to map inhibitory connections and could, e.g., reveal the matrix of synaptic weights of a neuron. (See J. J. Hopfield, Proc. Natl. Acad. Sci. USA 79, 2554 (1982)).

Since it is possible to analyze and visualize exemplary input maps online via, e.g., the Internet, intranet, extranet, virtual private network, direct connection, etc., it is possible to facilitate the use of some exemplary embodiments of the exemplary method, system, arrangement, computer-accessible medium and device in other applications. For example, after detecting true positives, it is possible to target and record electrophysiologically from the presynaptic neurons and to characterize them anatomically and physiologically. Input maps from a given presynaptic cell can then subsequently be obtained, so this method could be used sequentially to, e.g., optically trace circuits, particularly if the speed of the exemplary method and device is optimized with faster scanning in accordance with certain exemplary embodiments of the present disclosure.

Exemplary embodiments of the beam-multiplexing method and device according to the present disclosure can also be used to photorclease other neuroactive compounds with single-cell precision, for example. Also, it is possible to combine some exemplary embodiments with channelrhodopsin approaches (see E. S. Boyden, F. Zhang, E. Bamberg et al., Nature neuroscience 8 (9), 1263 (2005); F. Zhang, L. P. Wang, M. Brauner et al., Nature 446 (7136), 633 (2007)), in order to extend the method for in vivo applications, while still preserving single-cell resolution, for example.

Further, as shown in FIGS. 6(a)-6(c) and described herein above, some exemplary embodiments of a technique and device according to the present disclosure can be combined with two-photon calcium imaging. Therefore, some exemplary embodiments of a technique and device according to the present disclosure can be used as an all-optical stimulation and recording method and device to quickly examine the connectivity of a circuit and the functional regimes in which different groups of neurons can be activated, for example. Such exemplary approach can be used to, e.g., determine the role of individual neurons in biological circuits, reverse-engineer and decipher their transfer function, etc.

Exemplary Cell Detection, Fast Scanning and Detection of Action Potential with Calcium Imaging, and Labeling of Neurons FIG. 7(a) shows exemplary illustrations of exemplary results for an exemplary cell detection procedure and scanning path optimization. The original two-photon image 710 (left panel of FIG. 7(a)) can be analyzed online, which as shown in image 710, shows cells 711. Cell contours 713 can be automatically detected, as shown in image 712 (middle panel of FIG. 7(a)), for example. An exemplary convex-hull traveling-salesman algorithm can compute the shortest scanning path 715 between all cells 711, as shown in image 714

(right panel of FIG. 7(a)), for example. A exemplary P13 neocortical slice can be loaded with Indo-1AM and imaged with 730 nm excitation and a 40×0.8NA objective. The scale can be about 50 μm.

FIG. 7(b) shows an illustration of exemplary results for calcium imaging of targeted neurons. As shown in this exemplary illustration, an exemplary P14 neocortical slice can be loaded with Indo-1AM and a group of neurons 721 can be selected for vector mode imaging. A patch-clamped cell 722, indicated by arrow 723, can be filled with 50 μM Indo-1-K. The fluorescent level in loaded cells can be similar to the fluorescence of a patch-clamped cell 722. As shown by this example, the exemplary image can be taken at 735 nm excitation, with 40×0.8NA objective. The scale can be about 50 μm.

FIG. 7(c) shows exemplary schematics and exemplary graph results for a single action potential sensitivity of calcium imaging. As shown in such illustrations, referring to the exemplary graph 730 in FIG. 7(c), action potentials 732, with corresponding voltage recordings 733 and a holding potential of −65 mV, can be induced by an injection of current pulses 734, as illustrated in FIG. 7(c) by traces 735 in insets 731 and corresponding calcium signals 736, depicted by lower optical traces 737 (ΔF/F), from patched neuron showed clear responses to one or more spikes 738. The number 739 of action potentials 732 is indicated below the optical traces 737.

When slices are loaded and an imaged is acquired, it is possible to detect a position of, e.g., 500-4,000 neurons automatically. It is possible to utilize a procedure (see R. Cossart, D. Aronov, and R. Yuste, Nature 423, 283 (2003)) to detect the center of mass coordinates of all visible neurons from two-photon fluorescence images, as shown in, e.g., FIG. 7(a), image 712. Then, with the exemplary software (see V. Nikolenko, B. Nemet, and R. Yuste, Methods 30, 3 (2003)), it is possible to implement a predetermined scanning regime, e.g., "vector mode" regime, to perform simultaneous imaging and photoactivation. In contrast to raster scanning, in vector mode, the laser sequentially visits a user-selected set of points-of-interest ("targets", in this case, neuronal cell bodies) to perform point-measurements of fluorescence and/or photoactivate light-sensitive compounds, at a pre-defined duration and laser intensity. In order to optimize the scanning pattern, reduce delays between scanning points and minimize the wear of galvanometer scan mirrors, the sequence of targets can be re-ordered by using a fast algorithm that can find a near-optimal solution to the traveling salesman problem (e.g., a "convex-hull" procedure).

Using an exemplary vector mode, it is possible to measure the calcium signals generated by action potentials, induced by current injection. For example, it is possible to inject neurons with 50 μM Indo-1-K salt via a patch-clamp pipette. This intracellular concentration approximately corresponds to the intracellular concentration of the indicator obtained AM-dye loading (see Z. A. Peterlin, J. Kozloski, B. Mao et al., Proc. Natl. Acad. Sci. USA 97 (7), 3619 (2000)), as shown by the example of FIG. 7(b). Under these exemplary conditions, it is possible to detect calcium signals caused by individual action potentials, with an acceptable signal-to-noise ratio (e.g., 5 ms laser exposure per cell), as shown in FIG. 7(c), for example.

To visualize cell bodies of neurons and detect their coordinates, it is possible to load acute neocortical slices with membrane-permeant AM-ester calcium indicators. Because 700-735 nm light can be required for two-photon uncaging of MNI-caged L-glutamate, Indo-1AM can be used as the calcium indicator. Indo-1AM has shown to be good for loading of neurons (see R. Yuste and J. MacLean, in Imaging Neurons: a laboratory manual, edited by R. Yuste, F. Lanni, and A Konnerth (Cold Spring Harbor Press, Cold Spring Harbor, 2005)), and can have an appropriate calcium sensitivity in response to action potentials, as shown in the examples of FIGS. 7(a)-7(c). In addition, a low-affinity calcium indicator mag-Indo-1AM can load neocortical slices more efficiently than Indo-1AM. Even though mag-Indo-1AM may not be suitable for optical monitoring of action potentials (due to its low affinity for calcium), it can be very useful for fluorescent labeling of neuronal somata. Mag-Indo-1AM loading can be used to identify neurons for exemplary embodiments that do not require calcium imaging (e.g., for exemplary in input mapping). For combined exemplary imaging and/or uncaging, it is possible to jointly label with both Indo-1 indicators to obtain robust labeling of the neurons by mag-Indo-1AM, while still benefiting from the functional calcium sensitivity of Indo-1AM.

Indo-1AM and mag-Indo-1AM can provide, e.g., most neurons and may not significantly stain glia, as determined by dual labeling with Sulforhodamine 701. (See A. Nimmerjahn, F. Kirchhoff, J. N. Kerr et al., Nat Methods 1 (1), 31 (2004)). For example, 5.7±1.56% (145/2555; n=4 slices) of mag-Indo-1AM loaded cells can also be loaded with sulforhodamine, and only 8.1 t 2.59% (145/1786, n=4 slices) of sulforhodamine-loaded cells can also be loaded with mag-Indo-1AM.

Exemplary Slice Preparation and Loading

Coronal neocortical slices can be prepared from, e.g., P12-15 C57/BL6 mice or somatostatin-GFP mice (see A. A. Oliva, Jr., M. Jiang, T. Lam et al., J Neurosci 20 (9), 3354 (2000)) (e.g., Jackson Laboratory, Bar Harbor, Me.) with a vibratome (e.g., VT1000S; Leica, Nussloch, Germany). 300 μm thick slices can be cut in ice-cold oxygenated modified ACSF that can include 1 mM CaCl2 and 3 mM MgSO4, in which NaCl can be replaced by an equimolar concentration of sucrose (in mM): 27 NaHCO3, 1.5 NaH2PO4, 222 Sucrose, 2.6 KCl. Slices can then be placed in oxygenated standard ACSF at 37° C. for 30 min. For AM-loading, slices can be deposited onto the bottom of a small Petri dish (35×10 mm) filled with 2 ml of ACSF, ventilated with 95% O2/5% CO2 and placed in a slide warmer at 37° C. (Fisher Scientific, Waltham Mass.). An aliquot of 50 μg Indo-1AM or mag-Indo-1AM (Molecular Probes, Eugene, Oreg.) can be prepared in 10 μl DMSO and 2 μl of Pluronic F-127 (Molecular Probes). For combined loading, it is possible to use 50 μg Indo-1AM and 2 μg mag-Indo-1AM. The dye aliquot can then be placed into a Petri dish and slices can be incubated in the dark, and maintained at approximately 35-37° C. for up to, e.g., about 60 min. For double-labeling with, e.g., a mag-Indo-1AM and SR101, SR101 (20 μM) can be used for the last 15 minutes or so. Slices can then be kept at room temperature for at least about, e.g., 30 minutes before transferring them to a recording chamber. A standard ACSF, continuously aerated with 95% $O_2$, 5% $CO_2$, containing (in mM): 123 NaCl, 3 KCl, 26 $NaHCO_2$, 1 NaH2PO2, 10 dextrose, 1 $CaCl_2$ & 3 $MgSO_2$ can be used for mapping examples and loading, or 3 $CaCl_2$ and 1 $MgSO_2$ otherwise, for example.

Exemplary Two-Photon Uncaging of Glutamate

MNI-caged glutamate (2.5 mM; Tocris Cookson, UK) can be bath-applied and a Lambda (Bioptechs, Butler, Pa.) or Dynamax RP-1 (Rainin Instrument, Oakland, Calif.) peristaltic micropump can be used to control bath perfusion and minimize total bath volume, for example. Electrophysiological recordings can be analyzed (to detect, e.g., EPSP-like events time-locked to uncaging laser pulses) with custom software written in Matlab (e.g., The Mathworks, Natick, Mass.). For effective uncaging with shorter laser pulses, it is possible to use, e.g., up to 25 separate beamlets. It is also possible to provide larger multiplexing of the beam in accordance with some exemplary embodiments of the present disclosure.

Certain exemplary embodiments according to the present disclosure can use RuBi-Glutamate, a caged-glutamate compound based on ruthenium photochemistry. RuBi-Glutamate can be excited with visible wavelengths and releases glutamate after one- or two-photon excitation. It can be considered as having a high quantum efficiency and can be used at low concentrations, partly avoiding the blockade of GABAergic transmission that can be present with other caged compounds, for example. Two-photon uncaging of RuBi-Glutamate can have a high spatial resolution and generate excitatory responses in individual dendritic spines with physiological kinetics. With laser beam multiplexing, two-photon RuBi-Glutamate uncaging can also be used to, e.g., depolarize and fire pyramidal neurons with single-cell resolution. RuBi-Glutamate therefore can enable the photoactivation of neuronal dendrites and circuits with visible or two-photon light sources, achieving single cell, or even single spine, precision. For more information on RuBi-Glutamate and related example uses, see Fino, Elodie, Araya, Roberto, Peterka, Darcy S., Salierno, Marcelo, Etchenique, Roberto and Yuste, Rafael, *RuBi-Gltoamatle: two-photon and visible-light photoactivation of neurons and dendritic spines*, Frontiers in Neural Circuits, 3, 1 (2009). See also Rial Verde E M, Zayat L, Etchenique R, Yuste R. *Photorelease of GABA with Visible Light Using an Inorganic Caging Group*. Front Neural Circuits. 2008; 2:2. Epub 2008 Aug. 13, as an example of using in a similar fashion another compound (Rubi-GABA) based on ruthenium caging chemistry, in which it selectively photo-inhibits neurons.

Exemplary Complex Target Uncaging Techniques/Procedures

Glutamate Uncaging in Complex Targets Triggers Action Potentials

In previous uncaging experiments on dendritic spines, the effective radius of glutamate photorelease triggered by two-photon excitation was very small (approximately 2-3 µm in all dimensions (see Matsuzaki, M., et al. Dendritic spine geometry is critical for AMPA receptor expression in hippocampal CA1 pyramidal neurons. Nat Neurosci 4, 1086-1092. (2001); and Araya, R., Jiang, J., Eisenthal, K. B. & Yuste, R. The spine neck filters membrane potentials. Proc. Natl. Acad. Sci. USA 103, 17961-17966 (2006))), thus it became difficult to activate enough glutamate receptors to bring a neuron to action potential threshold. Indeed, upon two-photon uncaging of individual spines, the average size of recorded somatic events was less than 2 mV (e.g., for 2-10 ms pulses). The size of these events can depend on many factors: e.g., the duration of the uncaging pulse, the concentration of the MNI-glutamate, the laser intensity, the local density of glutamate receptors, etc. The laser intensity can be limited by a photodamage threshold (e.g., but preferably no more than about 25-35 mW on a sample with 0.8-0.95NA objectives, in exemplary experiments).

The laser intensity can also be limited by the concentration of a caged neurotransmitter, which can be limited by the solubility of the compound in the water (e.g., 10-50 mM of MNI-glutamate in case of local application ("puffing") as well as by the chemical purity. Caged glutamate typically has trace amounts of free glutamate and it is generally not practical to use more than 5 mM of MNI-glutamate in the case of a bath application. Thus, the rate and amplitude of depolarization can be effectively controlled by diffusion of the photoreleased free glutamate towards glutamate receptors, and, since the chemical reaction of uncaging itself can be very fast (see Canepari, M., Nelson, L., Papageorgiou, G., Corrie, J. E. & Ogden, D. Photochemical and pharmacological evaluation of 7-nitroindolinyl- and 4-methoxy-7-nitroindolinyl-amino acids as novel, fast caged neurotransmitters. J Neurosci Methods 112, 29-42 (2001), by the diffusion of MNI-glutamate into the illuminated area.

By targeting neuronal somata instead of spines, it is possible to use two-photon uncaging of MNI-caged glutamate to trigger action potentials in cortical neurons. (See Nikolenko. V., Ellis-Davies, G. C. R. & Yuste, R. Simultaneous optical stimulation and two-photon imaging of neocortical circuits, in Society for Neuroscience Annual Meeting (Society for Neuroscience, New Orleans, 2003). Using long laser pulses (e.g., about 10-50 ms) in positions close to the cell soma, it is possible to depolarize cells by approximately 5-10 mV, and it may not be simple to reach the action potential threshold. In addition, long uncaging durations can be capable of inducing photodamage and also may compromise the spatial resolution; by generating spill-over effects at these durations, for example.

To make neurons fire more reliably, it is possible to, e.g., use several uncaging locations and photorelease a larger amount of glutamate over a larger area. Thus, "complex targets" (see, e.g., illustration of FIG. 2(*a*)) can be provided for simultaneous photostimulation and calcium-imaging. A complex target can include several uncaging "stimulation sub-targets" and one "imaging sub-target" centered on the detected center of mass of a neuron. The beam can be sequentially placed at each stimulation location, at high laser intensity. Then, for imaging, the laser intensity can be reduced to a lower level and the laser beam positioned onto the imaging target. For efficient uncaging with high NA objectives, laser power levels of, e.g., approximately 30 mW can be used on a sample. For example, approximately 5 mW on the sample can be sufficient for point-measurements of fluorescence signals, with a good signal-to-noise ratio and without any detectable uncaging.

Exemplary Spatial Resolution of Complex Target Uncaging

In the case of a circular arrangement of stimulation targets, as shown in the illustration of FIG. 2(*a*) and described herein above, the diameter of the stimulation targets pattern can correspond approximately to the size of a typical neuronal soma. This exemplary arrangement can provide a repeatable triggering of action potentials in practically all stimulated neurons with, e.g., about 30-50 ms uncaging pulses (the total duration of all stimulation sub-targets), and can provide a good spatial resolution of photostimulation (see, e.g., illustration shown in FIGS. 2(*a*) and 2(*b*), and corresponding description herein). The actual exemplary parameters of the complex targets (e.g., number of stimulation sub-targets, circular pattern diameter, duration for each sub-target, uncaging power, etc.) can be adjusted individually for, e.g., different types of specific uses, applications, objective lens magnification, NA, etc. in accordance with some exemplary embodiments of the present disclosure.

Exemplary Input Mapping Protocols

After providing an exemplary embodiment of a two-photon uncaging technique and device which can be configured to stimulate individual neurons, it is possible to utilize such exemplary method, procedure and/or device for mapping input connections onto a neuron, as has been performed with one-photon glutamate uncaging photostimulation. (See I. C. Farber, supra; E. M. Callaway, supra; M. B. Dalva, supra; G. M. Shepherd, supra; C. Boucsein, supra; R. Kotter, supra; Hl. U. Dodt, supra; S. Shoham, supra; M. Canepari, supra). One exemplary limitation of one-photon uncaging can be the lack of spatial resolution in the lateral, and especially in the axial, direction. Although a certain level of spatial resolution can be achievable with high-NA objective lenses (see R. Kotter, supra), the cylindrical profile of an uncaging UV beam (see M. B. Dalva, supra; G. M. Shepherd, supra; C. Boucsein, supra) can be used to generate two-dimensional maps. Thus, in general, the maps that can be generated as such do not have single cell resolution, but rather reflect the activation of small territories.

The nonlinear nature of exemplary two-photon uncaging in accordance with certain exemplary embodiments of the present disclosure can be used overcome at least these limitations and perform mapping with single-cell precision.

An exemplary Photostimulation method and/or procedure in accordance with some exemplary embodiments of the present disclosure can include the following:
1. Loading acute slices with AM-dye (e.g., mag-Indo1AM);
2. Identifying the area and/or region of interest;
3. Patch-clamping of one or more neurons in a whole-cell mode (e.g., in current clamp);
4. Switching an objective lens to a lower magnification (e.g., to visualize all cortical layers in a single field of view);
5. Acquiring a 2D raster-mode image;
6. Analyzing the image, detecting individual neurons and determining center of mass coordinates;
7. Loading into processing arrangement including, e.g., a software program for sequential photostimulation (the loading can be performed, e.g., in a pseudo-random order);
8. Starting the photostimulation protocol, stimulating each neuron by, e.g., about 3-6 laser pulses with approximately 0.5 sec interval between pulses (the total duration of an exemplary protocol can be, e.g., approximately 25 min when stimulating about 500 neurons);
9. Identifying electrophysiological recordings;
10. Analyzing the electrophysiological recordings, identifying events resembling synaptic EPSP from a photostimulated cell (e.g., time-locked to uncaging pulses); and
11. Generating maps of input connections based on information associated with the identifying and analyzing of the electrophysiological recordings.

Exemplary Electrophysiological Methods and/or Procedures

According to certain exemplary embodiments of the present disclosure, neurons can be patch-clamped and the intracellular potential can be monitored simultaneously during imaging and/or uncaging. Whole-cell current-clamp recordings can be made using, e.g., a BVC-700 (Dagan Corp., Minneapolis, Minn.) or Axoclamp 700B (Axon Instruments, Foster City, Calif.) amplifiers. 6-10MΩ micropipettes can be filled with (in mM), e.g.: 130K-methylsulfate, 10 KCl, 10 Na-IIEPES, 2.5ATP-Mg, and 0.3GTP-Na and 0.35% biocytin, pH 7.4 (294-6 mOsm), and about 50 µM fluorescent dyes Indo-1-K pentapotassium salt (for calibration examples) or Alexa-594 (e.g., for mapping to visualize the dendritic tree by using about an additional 600 nm long-pass filter in front of the PMT: both dyes can be from Molecular Probes, OR). For example, neurons can be filled with biocytin during recording and be processed, e.g., for morphological identification.

Exemplary methods and/or procedures that utilize simultaneous photostimulation and calcium imaging can be performed in a physiological temperature in order to study network activity in a system that is as close as possible to the physiological state. To improve the duration of the whole-cell recordings, it is possible, e.g., to perform exemplary mapping at room temperature.

Exemplary Histological Methods

Slices can be fixed using, e.g., a 4% paraformaldehyde solution in 0.12 M phosphate buffer (PB). Following imaging/uncaging examples, slices can be submerged in room temperature fixative and allowed to fix overnight at about 4'C. Slices can then be, e.g., rinsed in 0.12M PB 3 times, cryoprotected in about 20% sucrose in 0.12M PB for about 12-168 hours and frozen on dry ice in tissue freezing medium (H-TFM, Triangle Biomedical Sciences, Durham, N.C.). Upon defrosting, slices can be rinsed in 0.12M PB three times and pretreated with 1% hydrogen peroxide in 0.12M PB for about 30 minutes under agitation at room temperature, for example. The tissue can then be rinsed in 0.02M potassium phosphate saline (KPBS) and incubated in avidin-biotin-peroxidase complex (catalog number PK-6100, Vector Laboratories, Inc., Burlingame, Calif.) overnight under agitation at room temperature (10 µl solution A and 10 µl solution B per 1 ml of 0.02M KPBS and 0.3% Triton-X). Slices can be rinsed in 0.02M KPBS about 3 times and incubated in about 0.7 mg/ml 3,3'-diaminobenzidine, 0.2 mg/ml urea hydrogen peroxide, 0.06M Tris buffer (D-4293, Sigma-Aldrich, St. Louis, Mo.) in 0.02M KPBS for about 5-15 minutes. Upon completing 3,3'-diaminobenzidine reaction, slices can be rinsed in 0.02M KPBS and mounted in Vectashield mounting medium (H-1000, Vector Laboratories, Inc.). Stained cells can be visualized with DIC optics using an Olympus upright microscope (BX51), and 71 neurons can be reconstructed in 3 dimensions using, e.g., the Neurolucida workstation (e.g., MicroBrightField Inc., Williston, Vt.). All reconstructions can be done under a 100×, 1.40 NA objective, for example.

Referring back to FIGS. 7(a)-(c), which show an exemplary embodiment of a system according to the present disclosure, as described herein above, various modifications can be made to the exemplary previously described custom two-photon fluorescence (2PF) and second harmonic generation (SHG) microscope. (See Shoham, S., O'Connor, D. H., Sarkisov, D. V. & Wang, S. S. Rapid neurotransmitter uncaging in spatially defined patterns. Nature methods 2, 837-843 (2005); and Majewska, A., Yiu, G. & Yuste, R. A custom-made two-photon microscope and deconvolution system. Pflitgers Archiv—Eur. J. Physiol. 441, 398-409 (2000)). For example, the intensity of the beam from a NIR pulsed mode-locked Ti:Sapphire laser 701 can be controlled by Pockels cell 702. The collimated beam can then be focused by a piano-convex lens 703a onto the pinhole 703b that can serve as a spatial filter, and later re-collimated by the second lens 703c. The DOE 4 can split the laser beam onto a number of, e.g., five, individual beamlets (as shown in the illustration of FIG. 2(b)) that can spread at about 0.23° inter-beamlet angle.

Turning to FIG. 7(a), this angle can be decreased by a second telescope (two piano-convex lenses 705a and 705c that can also image the DOE onto the optical plane of scan mirrors 707b while keeping individual beamlets collimated. An iris 705b can be placed in between the lenses 705a and 705c to switch between single-beam raster-mode imaging (when it is closed can facilitate for the central beamlet to pass) and five-beamlet DOE vector mode imaging/photostimulation (when the iris 705b is completely opened). For example, an approximately 700 nm long-pass filter 706a can remove residual visible-light radiation from the laser and periscope mirrors 706 can deliver the beam from the optical table plane to the scanning unit 707 that can include a holder for IR-reflecting mirror or dichroic 707a and galvanometer scan mirrors 707b.

Scan lens (or "pupil-transfer" lens) 707c shown in FIG. 7(a) can mechanically couple the scanning unit 707 to the upright microscope 708 and form a telescope with a tube lens of the microscope 708b to deliver the collimated beam to the back aperture of the objective 708c. It also and optically can conjugate the scan mirrors and the objective. The two-photon fluorescence (2PF) signal can be collected by the same objective and separated from the excitation light by a short-pass dichroic 708a, and be detected by the PMT 709 after being filtered through additional color filter(s) 709a and focused onto a small active area of the PMT 709 by an additional lens 709b. The fast shutter 709c can protect the PMT 709 from overloading during uncaging pulses. Alternatively, 2PF or second-harmonic generation (SHG) signals can be collected via the microscope condenser 708d, and detected by a second PMT assembly 712. The electrical signal from the PMTs 709, 712 can be amplified by pre-amplifier(s) 710 and digitized by a data acquisition board 711.

Turning to FIG. 8, an example of two-photon fluorescence image 801 is shown which is provided from a P13 somatosensory (SI) neocortical slice 802, loaded with mag-Indo-1AM. The image can be acquired in raster mode (725 nm excitation) with a 10×0.3NA objective, and a single optical section in axial (Z) direction is shown, with no additional scanning zoom. The scale in this example is 200 µm. The pial surface 803 is shown as being on the top, and all cortical layers are visible.

Figure 9A:
Figure 9B:
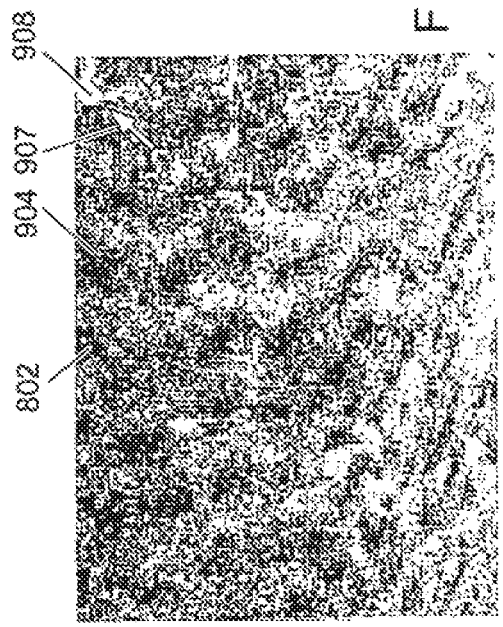

FIGS. 9(a) and 9(b) show exemplary images of the same exemplary slice 802 of FIG. 8 taken at 10× (0.3 NA) of mag-indol-AM (e.g., 725 nm excitation, 480/540 nm filter) and SR101 (e.g., as shown in FIG. 9(b)—850 nm excitation, 595/615 nm filter) across all cortical layers. The exemplary scale in this example is about 100 µm.

Figure 9C:
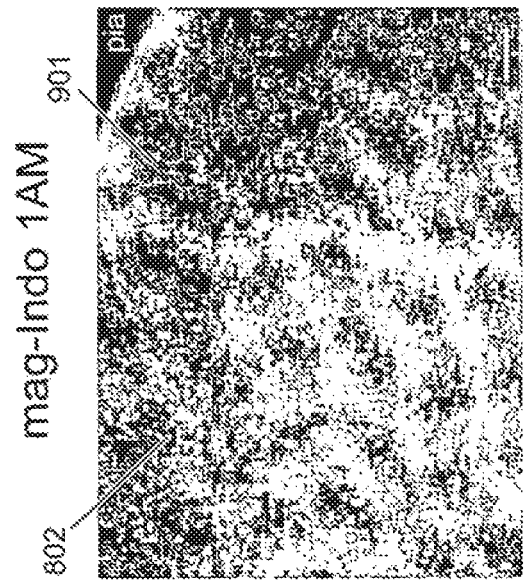
Figure 9D:
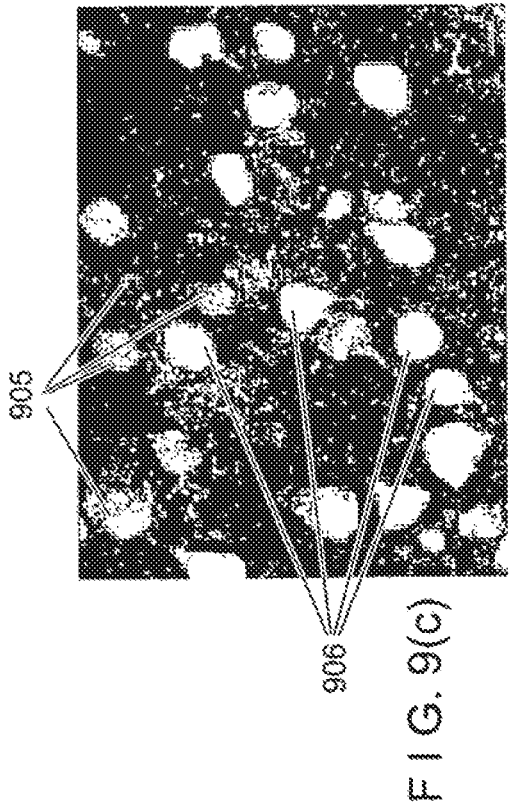

FIGS. 9(c) and 9(d) show exemplary images 903 and 904, respectively, that illustrate exemplary cells 905 from the exemplary slice 802 at higher magnification (60×, 0.9 NA). A higher density of mag-Indo1-AM-positive cells 906 is provided in FIG. 9(c) than SR101-positive cells of FIG. 9(d), and overall low degree of overlap. An arrow 907 in FIG. 9(d) indicates a SR101 labeled cell 908 (e.g., an astrocyte) also loaded with mag-Indo1-AM. The scale in these exemplary figures is about 10 µm.

Referring back to the images shown in FIGS. 4(g)-4(l) which are described herein above, these exemplary images 470-475 are exemplary illustrations of examples of mapping synaptic inputs by using quadruple recording from adjacent neurons. For example, similarly as shown in FIG. 9(a), four layer 5 pyramidal cells can be patched (white arrows 480 point to locations of corresponding cell bodies 476-479) and four corresponding input maps can be acquired during a single run of an exemplary stimulation protocol. The morphological reconstructions of dendritic trees for neurons A 476, B 477 and D 479 can be superimposed. The exemplary scale in this example is about 100 µm. In particular, as shown in FIGS. 4(g)-4(j), input coded maps can be provided, e.g., for all four neurons. An exemplary coding scheme could be, e.g., a color coded scheme proportional to amplitude of EPSP, for example, but reversed relative to FIG. 9(a), in order to enhance visibility on the dark background so that, e.g., lighter shades correspond to larger peak amplitude.

FIGS. 4(k) and 4(l) illustrate images of exemplary representative maps of $2^{nd}$ and $3^{rd}$ order overlap between neurons A 476 and B 477, and neurons A 476, B 477 and C 478, respectively.

FIG. 10 shows an exemplary flow diagram of a Photostimulation procedure or method in accordance with certain exemplary embodiments of the present disclosure which can be executed by a processing arrangement (e.g., a computer processor or a collection of processors). As shown in FIG. 10, the exemplary procedure can be executed on and/or by the processing arrangement 1000 (e.g., one or more microprocessor or a collection thereof). Starting at 1001, the exemplary procedure can load acute slices with AM-dye (e.g., mag-Indo1AM). In 1002, the exemplary procedure can identify the area and/or region of interest. In 1003, the exemplary procedure can patch-clamp one or more neurons in a whole-cell mode (e.g., in current clamp). In 1004, the exemplary procedure can switch an objective lens to a lower magnification (e.g., to visualize all cortical layers in a single field of view). In 1005, the exemplary procedure can acquire a 2D raster-mode image; analyzing the image, then detect individual neurons and determine center of mass coordinates—1006.

In 1007, the exemplary procedure can load into processing arrangement including, e.g., a software program for sequential photostimulation (the loading can be performed, e.g., in a pseudo-random order); then start the photostimulation protocol, stimulating each neuron by, e.g., about 3-6 laser pulses with approximately 0.5 sec interval between pulses (the total duration of an exemplary protocol can be, e.g., approximately 25 min when stimulating about 500 neurons)—1008; In 1009, the exemplary procedure can identify electrophysiological recordings; and then, in 1010, analyze the electrophysiological recordings, identifying events resembling synaptic EPSP from a photostimulated cell (e.g., time-locked to uncaging pulses). In 1011, the exemplary procedure can generate maps of input connections based on information associated with the identifying and analyzing of the electrophysiological recordings.

Exemplary Methods for Laser Multiplexing with SLM and Results

FIG. 11 shows a flow diagram of an exemplary embodiment of a method or procedure for SLM phase mask formation in accordance with the present disclosure.

The exemplary SLM procedure is able to generate arbitrary patterns because of a fundamental property in optics: that of the optical Fourier Transform. For a transparent object placed exactly one focal length in front of a thin lens, the Fourier Transform of that object can be formed one focal length behind the lens. Thus, if the incoming field at focal$_{front}$ is represented by the complex amplitude $E_k$, the field at focal$_{back}$ is $F_k$, where $E_k$ and $F_k$ are Fourier transform pairs. In an exemplary microscope, though the optical path is made more complex by a system of relay lenses, the SLM can be located at focus$_{front}$ and sample plane at focal$_{back}$. A phase only SLM can act only on the phase of the field, not the amplitude. Once acted upon by the SLM, the electric field is $E_k=A_0 \exp(i \cdot \Phi_k)$, where $\exp(i \cdot \Phi_k)$ is the original amplitude, and $\Phi_k$ the phase instilled by the SLM. The phase, $\Phi_k$, is computed such that the desired intensity pattern is produced in the far field (sample plane). The phase mask can be computed or determined using, e.g., software from Holoeye, as well as from custom-developed software based on standard iterative-adaptive procedures.

As shown in FIG. 11, the exemplary procedure/method starts with the known intensity distribution of the laser in 1101, and then adds a random phase (speeds convergence) in 1102, generating $E_k=A_0 \exp(i \cdot \Phi_k)$ in 1103. In 1104, the exemplary procedure/method then computes or determines the FFT, $F_k=B_k \exp(i \cdot \Theta_k)$ and compares the computed image to the desired image in step 1105. If the error exceeds a threshold, then, in 1106, the amplitude, but not the phase, is modified to better match the desired image. In 1107, an inverse transform is performed, and in 1108, constraints applied, such as phase quantization, giving rise to a new input field in 1109, and the cycle begins again. If the error does not exceed a threshold in step 1105, then, the exemplary procedure proceeds to 1110, wherein a phase mask is set.

FIGS. 12(a)-12(d) show exemplary SLM light patterning and depth focusing images and sequences for obtaining thereof result from exemplary experiments in accordance with the present disclosure. For example, imaging of samples of an agarose gel saturated with Alexa 488 fluorescence indicator for testing the efficiency of two-photon excitation. The exemplary images were acquired using 60×0.9NA objective. Scale of about 20 μm. FIG. 12(a) shows a simple exemplary Binary bitmap pattern (e.g., illustrated as text "COLUMBIA") that was uploaded into the exemplary SLM software, as shown in the first panel 1201. An obtained phase mask is shown in the second panel 1202. Grayscale corresponds to phase shift from 0 to 2π. The resulting two-photon fluorescence image acquired with microscope CCD camera from the sample (recording chamber) is shown in the right panel 1203. As shown in the figures, there is a good correspondence between the calculated pattern and the obtained image. This data also demonstrates that liquid-crystal based diffractive SLM can withstand illumination by a powerful pulsed mode-locked ultrafast laser and be effectively used for structured non-linear illumination.

FIG. 12(b) shows exemplary complex gray-scale patterns can be used to program SLM. It is possible to use used a stylized picture of Santiago Ramón y Cajal, based on a historical photograph. The exemplary panels 1204-1205 in this experiment are similar to the panels 1201-1204 of FIG. 12(a).

FIG. 12(c) shows exemplary focusing with an SLM. As shown, an exemplary embodiment of the SLM software can facilitate the application of additional optical functions on top of the phase mask. In this example, it is possible to use a lens function to shift the focus of excitation in axial dimension. The exemplary panels 1207-1211 show the original image and exemplary panels 1212-1216 show the corresponding phase mask, as well as the exemplary lens phase function alone and added to original phase mask. The −10, −100, +10 and +100 are exemplary units used by the exemplary software to indicate correspondingly negative/positive lens and relative optical strength.

FIG. 12(d) shows two-photon fluorescence image in an exemplary left panel 1217 of a test pattern acquired with the CCD camera. As shown by panels 1218-1225, the virtual focus plane is moved away in both directions from the original plane using a lens function of corresponding strength. A 40×0.8 NA objective was used. Scale is about 50 μm. This exemplary data illustrates that SLM can be used as a "universal scanners" that do not require physically moving parts.

FIG. 13 is a block diagram of a system or an arrangement configured in accordance with certain exemplary embodiments of the present disclosure, which can be programmed or configured to execute any of the exemplary procedures, methods and processes.

As shown in FIG. 13, e.g., a computer-accessible medium 1303 (e.g., as described herein above, storage device such as hard disk, floppy disk, memory stick, CD-ROM, RAM, ROM, etc., or a collection thereof) can be provided (in communication with the processing arrangement 1301). The computer-accessible medium 1303 can contain executable instructions 1305 thereon. In addition or alternatively, a storage arrangement 1307 can be provided separately from the computer-accessible medium 1303, which can provide the instructions to the processing arrangement 1301 so as to configure the processing arrangement to execute certain exemplary procedures, processes and methods, as described herein above.

The exemplary techniques described herein can be performed using a processor or a group of processors. In addition, the exemplary procedures described herein can be implemented using a computer software which can be stored on a computer-accessible medium (e.g., at least one hard drive, floppy disk, memory stick or card, RAM, ROM, or any other computer storage device).

The foregoing merely illustrates the principles of the exemplary embodiments of the present disclosure. Various modifications and alterations to the described embodiments will be apparent to those skilled in the art in view of the teachings herein. It will thus be appreciated that those skilled in the art will be able to devise numerous systems, arrangements and methods which, although not explicitly shown or described herein, embody the principles of the invention and are thus within the spirit and scope of the present invention. In addition, to the extent that the prior art knowledge has not been explicitly incorporated by reference herein above, it is explicitly being incorporated herein in its entirety. All publications referenced herein above are incorporated herein by reference in their entireties, as applicable. In the event of a conflict between the teachings of the present disclosure and those of the incorporated document, the teachings of the present disclosure.

What is claimed is:

1. A device for affecting at least one radiation and imaging neuronal circuits, comprising:
   at least one spatial light modulator (SLM) which is structured or configured to:
      affect a user-specified three-dimensional spatial profile of the at least one radiation;
      split the at least one radiation into multiple beamlets;
      combine the beamlets using at least one galvanometer mirror: and
      trigger at least one of a photo activation, a photo-inactivation or a photo-chemical effect of at least one portion of at least one sample by exciting the at least one portion in a non-linear manner using the beamiets.

2. The device according to any of claim 1, wherein the at least one sample is at least one of a biological sample, a chemical composition, a semiconductor arrangement r r a drug-delivery arrangement.

3. The device according to claim 1, wherein the at least one SLM includes at least one diffractive optical arrangement.

4. The device according to claim 1, wherein the at least one SLM includes a diffractive optical element (DOE).

5. The device according to claim 1, wherein the at least one SLM affects the at least one radiation using a phase only modulation.

6. The device according to claim 1, wherein a signal-to-noise ratio of the at least one radiation is greater than about 1.94 fold over a signal from a single radiation system.

7. The device, according to claim 1, further comprising at least one computer hardware arrangement which is configured, to receive data associated with the at least one affected radiation and generate at least one image of the at least one portion of the at least one sample as a function of the data, wherein the at least one image is generated at a duration of the imaging cycle that is less than about 100 ms.

8. The device according to claim 1, wherein the at least one SLM is configured or structured to at least one of:
   (i) provide the at least one affected radiation to a biological sample to provide a photodynamic effect thereto, wherein the at least one affected radiation has an average power that is higher than 100 milliwatts net on the at least one sample,
   (ii) illuminate microscopic structures within the at least one sample using the at least one radiation, or
   (iii) adjust a phase of the at least one radiation to impact the at least one sample and obtain at least one depth information therefor.

9. The device according to claim 1, wherein at least a portion of the at least one SLM is provided in an endoscopic arrangement.

10. The device according to claim 1, wherein the SLM arrangement is configured or structured to at least one of:
   (i) illuminate microscopic structures within the at least one sample using the at least one radiation,
   (ii) adjust a phase of the at least one radiation to impact the at least one sample and obtain at least one depth information therefor,
   (iii) control a delivery of the at least one radiation in a targeted manner by controlling an intensity of the at least one radiation to a particular location on or in the at least one sample, or
   (iv) provide a specified spatial profile of the at least one radiation on an image plane of the at least one sample.

11. The device according to claim 1, wherein the at least one SLM is included in at least one scanless SLM-based microscope arrangement which affects a coherent light of the at least one radiation.

12. The device according to claim 1, further comprising at least one computer hardware arrangement which is configured to receive data associated with the at least one affected radiation and generate at least one image of at least one portion of the at least one sample as a function of the data, wherein the at least one SLM is configured or structured to at least one of (i) correct for at least one aberration associated with the at least one sample for the at least one image, or (ii) modify at least one of a shape, a size or a flow direction of beams of the at least one radiation to effectuate a two-photon absorption within the at least one sample.

13. The device according to claim 1, wherein the at least one radiation includes at least one light radiation, wherein the at least one SLM is configured or structured to provide the at least one light radiation to the at least one portion of the at least one sample at a depth that is greater than about 1 mm, and wherein the at least one light radiation is provided at the depth within the at least one portion that is based on at least one wavelength of the at least one light radiation.

14. The device according to claim 13, wherein the at least one light radiation is provided to a specific target at the depth within the at least one portion with an intensity that is greater than that described by $I = I_0 \exp(\sigma_{wi} Z)$, wherein $I_0$ is an original intensity at a surface of the at least one sample, $z$ a depth of a penetration of the at least one radiation, and $\sigma_{wi}$ is an effective attenuation constant which is a sum of a wavelength dependent average absorption and a wavelength scattering coefficient of a bulk material.

15. The device according to claim 1, further comprising at least one computer hardware arrangement which is configured to receive data associated with the at least one affected radiation and generate at least one image of at least one portion of the at least one sample as a function of the data and based on at least one multi-mode procedure, wherein the at least one SLM is further structured or configured to generate a set of angled intersecting beamlets from the at least one radiation.

16. The device according to claim 1, wherein the at least one SLM arrangement is structured or configured to affect the at least one radiation to effectuate at least one of (i) a two-photon absorption within the at least one sample, (ii) a three-photon absorption within the at least one sample, or (iii) a Second Harmonics Generation (SHG) associated with the at least one radiation.

17. The device according to claim 1, further comprising at least one computer hardware arrangement which is configured to receive data associated with the at least one affected radiation and generate at least one image of the at least one portion of the at least one sample as a function of the data, wherein the at least one SLM arrangement is structured or configured to affect the at least one radiation to effectuate at least one of (i) a coherent anti-Stokes Raman spectroscopic imaging (CARS) procedure so that the at least one computer hardware arrangement generates the at least one image, or (ii) a Four-wave mixing imaging (FWM) procedure so that the at least one computer hardware arrangement generates the at least one image.

18. The device according to claim 1, wherein the at least one SLM is a phase-only SLM which prevents a substantial reduction of intensity of the at least one radiation.

19. The device according to claim 1, wherein the at least one SLM includes a single optical component which is solely configured or structured to (i) transmit or reflect and further modify the at least one radiation, (ii) reduce an intensity of the at least one radiation, or (iii) at least partially block the at least one radiation.

20. The device according to claim 1, further comprising at least one computer hardware arrangement which is configured to receive data associated with the at least one affected radiation and generate at least one three-dimensional image of the at least one portion of the at least one sample as a function of the data, the at least one computer hardware arrangement is further configured or structured to store further data associated with the three-dimensional image as three-dimensional data.

21. The device according to claim 1, wherein the at least one SLM is configured or structured to trigger the photo activation of the at least one portion concurrently at multiple specified locations.

22. The device according to claim 1, wherein the at least one light radiation is provided to a specific target at the depth within the at least one portion with a modulated intensity which is different from an expected result under predetermined illumination conditions.

23. The device according to claim 1, wherein the photochemical effect comprises a photorelease.

24. A method for affecting at least one radiation and imaging neuronal circuits, comprising:
   affecting a user-specified three-dimensional spatial profile of the at least one radiation;
   splitting the at least one radiation into multiple beamlets;
   combining the beamlets using at least one galvanometer mirror; and
   triggering at least one of a photo activation, a photo-inactivation or a photo-chemical effect of at least one sample by exciting the at least one sample in a non-linear manner using the beamlets.

25. A device for affecting at least one radiation, comprising:
   at least one spatial light modulator (SLM) which is structured or configured to affect a user-specified three-dimensional spatial profile of the at least one radiation to trigger at least one of a photo activation, a photo-inactivation or a photo-chemical effect of at least one portion of at least one sample by exciting the at least one portion in a non-linear manner using the at least one radiation.

* * * * *